United States Patent
Yamano et al.

(10) Patent No.: US 9,815,938 B2
(45) Date of Patent: Nov. 14, 2017

(54) PRODUCTION METHOD FOR POLY(AMINO ACID)

(71) Applicant: TAKEDA PHARMACEUTICAL COMPANY LIMITED, Osaka-shi, Osaka (JP)

(72) Inventors: Mitsuhisa Yamano, Nishinomiya (JP); Toshiaki Nagata, Ibaraki (JP); Hideki Saitoh, Osaka (JP)

(73) Assignee: TAKEDA PHARMACEUTICAL COMPANY LIMITED, Osaka-Shi, Osaka (JP)

( * ) Notice: Subject to any disclaimer, the term of this patent is extended or adjusted under 35 U.S.C. 154(b) by 0 days.

(21) Appl. No.: 14/392,185

(22) PCT Filed: Jun. 25, 2014

(86) PCT No.: PCT/JP2014/066870
§ 371 (c)(1),
(2) Date: Dec. 23, 2015

(87) PCT Pub. No.: WO2014/208611
PCT Pub. Date: Dec. 31, 2014

(65) Prior Publication Data
US 2016/0177032 A1    Jun. 23, 2016

(30) Foreign Application Priority Data

Jun. 26, 2013 (JP) .................... 2013-133917

(51) Int. Cl.
| | |
|---|---|
| A61K 47/34 | (2017.01) |
| C08G 69/08 | (2006.01) |
| C08G 69/10 | (2006.01) |
| C08G 69/48 | (2006.01) |
| A61K 39/39 | (2006.01) |
| C08L 77/04 | (2006.01) |
| A61K 39/00 | (2006.01) |

(52) U.S. Cl.
CPC .............. C08G 69/48 (2013.01); A61K 39/39 (2013.01); A61K 47/34 (2013.01); C08G 69/08 (2013.01); C08G 69/10 (2013.01); C08L 77/04 (2013.01); *A61K 2039/55555* (2013.01); *A61K 2039/6093* (2013.01)

(58) Field of Classification Search
CPC .... A61K 9/5107; A61K 9/5169; A61K 47/42; A61K 2039/6093; A61K 2039/55555; C08G 69/08; C08G 69/10; C08G 69/48
See application file for complete search history.

(56) References Cited

U.S. PATENT DOCUMENTS

| | | | |
|---|---|---|---|
| 6,630,171 B1 | 10/2003 | Huille et al. | |
| 7,785,612 B2* | 8/2010 | Akashi | A61K 39/21 424/280.1 |
| 2007/0178126 A1* | 8/2007 | Angot | A61K 8/88 424/401 |
| 2009/0156480 A1* | 6/2009 | Akashi | A61K 9/5146 514/1.1 |
| 2011/0150837 A1 | 6/2011 | Chan et al. | |

FOREIGN PATENT DOCUMENTS

| | | |
|---|---|---|
| JP | 6-92870 A | 4/1994 |
| JP | 6-256220 A | 9/1994 |
| JP | 2002-519457 A | 7/2002 |
| JP | 2006-510792 A | 3/2006 |
| JP | 2007-297559 A | 11/2007 |
| WO | 2006/112477 A1 | 10/2006 |
| WO | 2009/133968 A1 | 11/2009 |

OTHER PUBLICATIONS

Akagi et al. Preparation and characterization of biodegradable nanoparticles based on poly(glamma-glutamic acid) . . . Journal of Controlled Release. 2005, vol. 108, pp. 226-236.*
Akagi et al. Hydrolytic and Enzymatic Degradation of Nanoparticles Based on Amphiphilic Poly(gamma-glutamic acid)-graft-L-phenylalanine Copolymers. Biomacromolecules. 2006, vol. 7, No. 1, pp. 297-303.*
ISR issued in international application No. PCT/JP2014/066870 dated Sep. 22, 2014.
IPRP issued in International application No. PCT/JP2014/066870 dated Dec. 29, 2015.
European Search Report dated Feb. 23, 2017 in corresponding European Application No. 14818491.4.

* cited by examiner

*Primary Examiner* — Jeffrey E Russel
(74) *Attorney, Agent, or Firm* — Nath, Goldberg & Meyer; Joshua B. Goldberg; Scott H. Blackman

(57) ABSTRACT

The present invention relates to a graft copolymer of a poly(amino acid) or a salt thereof and a hydrophobic primary amine compound or a salt thereof (e.g., a graft copolymer (γ-PGA-PAE) of poly(γ-glutamic acid) (γ-PGA) and phenylalanine ethyl ester (PAE)), an ionized graft copolymer of a poly(amino acid) or a salt thereof and a hydrophobic primary amine compound or a salt thereof, nanoparticles containing the ionized graft copolymer, and a production method thereof. The nanoparticles acquired in this way are useful as an adjuvant for producing a vaccine.

7 Claims, 1 Drawing Sheet

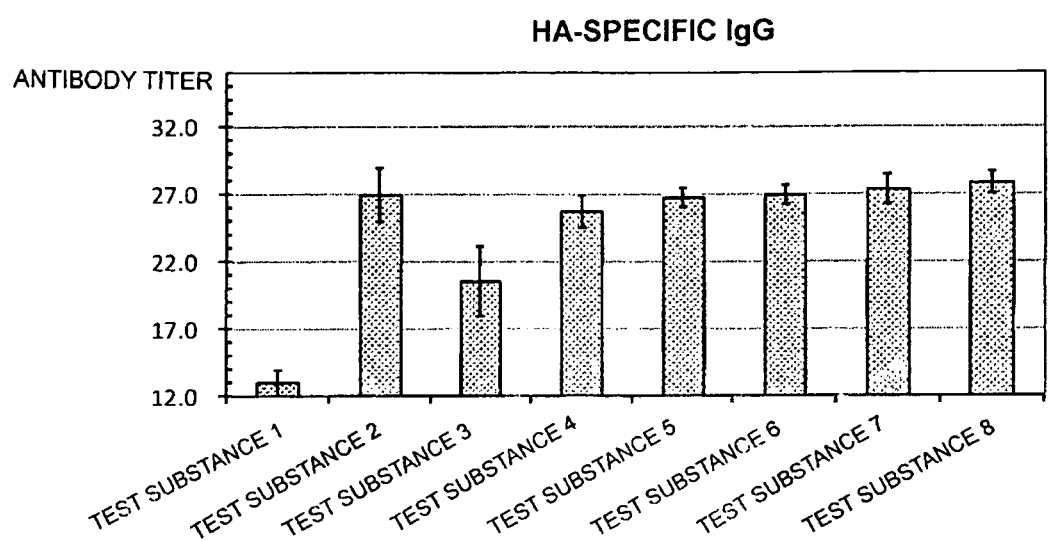

PRODUCTION METHOD FOR POLY(AMINO ACID)

This is a National Phase Application filed under 35 U.S.C. 371 as a national stage of PCT/JP2014/066870, filed Jun. 25, 2014, an application claiming the benefit of Japanese Application No. 2013-133917, filed Jun. 26, 2013.

TECHNICAL FIELD

The present invention relates to a graft copolymer of a poly(amino acid) or a salt thereof and a hydrophobic primary amine compound or a salt thereof [e.g., a graft copolymer (γ-PGA-PAE) of poly(γ-glutamic acid) (γ-PGA) and phenylalanine ethyl ester (PAE)], which is useful as an adjuvant for producing a vaccine, an ionized graft copolymer of a poly(amino acid) or a salt thereof and a hydrophobic primary amine compound or a salt thereof, nanoparticles containing the ionized graft copolymer, and a production method thereof.

BACKGROUND ART

Studies are recently conducted for utilizing nanoparticles as a drug carrier (see Patent Documents 1 and 2).

Patent Document 3 discloses that a poly(amino acid) (e.g., γ-PGA) or a graft copolymer of a poly(amino acid) and a hydrophobic primary amine compound or a salt thereof (e.g., γ-PGA-PAE) promotes differentiation and maturity of dendritic cells, i.e., acts as an adjuvant and that the adjuvant action is enhanced by formation of nanoparticles of the graft copolymer.

Patent Document 3 discloses in Example 1 a production method of γ-PGA-PAE using a salting-out method for desalting after reaction of γ-PGA with carbodiimide hydrochloride and PAE, and a method of producing nanoparticles from γ-PGA-PAE.

PRIOR ART DOCUMENT

Patent Documents

Patent Document 1: Japanese Laid-Open Patent Publication No. 6-92870
Patent Document 2: Japanese Laid-Open Patent Publication No. 6-256220
Patent Document 3: WO 2006/112477

SUMMARY OF THE INVENTION

Problem to be Solved by the Invention

What is required is a method of producing a graft copolymer of a poly(amino acid) or a salt thereof and a hydrophobic primary amine compound or a salt thereof useful as an adjuvant for a vaccine in a large amount in a short time.

Means for Solving Problem

As a result of intensive studies for solving the problem, the inventors have found a method of producing a free form of a graft copolymer of a poly(amino acid) or a salt thereof and a hydrophobic primary amine compound or a salt thereof in a short period of time at a high yield by using a method of precipitation by acid addition for isolation of the graft copolymer.

The inventors also have found a method of acquiring nanoparticles with higher efficiency and higher reproducibility than those of the conventional methods by partially or entirely ionizing the free form of the graft copolymer of a poly(amino acid) or a salt thereof and a hydrophobic primary amine compound or a salt thereof. This method also enables a scale-down of manufacturing equipment and a reduction of the waste. Additionally, even when it is conventionally difficult to form nanoparticles from the free form of the graft copolymer of a poly(amino acid) or a salt thereof and a hydrophobic primary amine compound or a salt thereof, the partial or entire ionization facilitates the formation of nanoparticles.

Therefore, the present invention relates to:

[1] a production method of a graft copolymer of a poly(amino acid) selected from the group consisting of poly(γ-glutamic acid), poly(α-glutamic acid), and poly(aspartic acid) or a salt thereof and a hydrophobic primary amine compound represented by Formula (I): $A-NH_2$ [wherein A denotes a hydrophobic moiety] or a salt thereof, the method comprising the steps of:

(1) acquiring a graft copolymer by condensation of the poly(amino acid) or a salt thereof with the hydrophobic primary amine compound represented by Formula (I) or a salt thereof; and (2) isolating the graft copolymer by allowing an acid to act on the graft copolymer acquired at step (1);

[2] the production method according to [1], wherein at step (2), the acid is allowed to act on the graft copolymer at a temperature of 0 to 80° C.;

[3] the production method according to [1], wherein the poly(amino acid) is poly(γ-glutamic acid);

[4] the production method according to [1], wherein the hydrophobic primary amine compound is an α-amino acid derivative;

[5] the production method according to [4], wherein the α-amino acid derivative is a phenylalanine derivative;

[6] the production method according to [5], wherein the phenylalanine derivative is phenylalanine ethyl ester;

[7] a graft copolymer of a poly(amino acid) selected from the group consisting of poly(γ-glutamic acid), poly(α-glutamic acid), and poly(aspartic acid) or a salt thereof and a hydrophobic primary amine compound represented by Formula (I): $A-NH_2$ [wherein A denotes a hydrophobic moiety] or a salt thereof, the graft copolymer being produced with the method according to [1];

[8] a production method of an ionized graft copolymer of a poly(amino acid) selected from the group consisting of poly(γ-glutamic acid), poly(α-glutamic acid), and poly(aspartic acid) or a salt thereof and a hydrophobic primary amine compound represented by Formula (I): $A-NH_2$ [wherein A denotes a hydrophobic moiety] or a salt thereof, the method comprising the step of:

ionizing the graft copolymer by allowing a hydroxide of alkali metal, a carbonate of alkali metal, a hydrogencarbonate of alkali metal, a phosphate of alkali metal, a monohydrogen phosphate of alkali metal, a dihydrogen phosphate of alkali metal, an organic acid salt of alkali metal, or an acidic amino-acid salt of alkali metal to act on the graft copolymer of the poly(amino acid) or a salt thereof and the hydrophobic primary amine compound or a salt thereof;

[9] An ionized graft copolymer represented by Formula (II):

[Chem. 1]

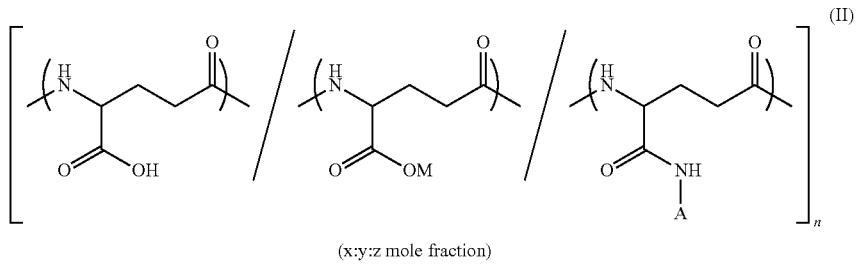

(x:y:z mole fraction)

[wherein M is alkali metal, A is a hydrophobic moiety, and n is an integer from 10 to 100,000; diagonal lines intervening three monomer units represent that the monomer units are arranged in irregular order; and x is a mole fraction of the monomer unit represented by Formula (III):

[Chem. 2]

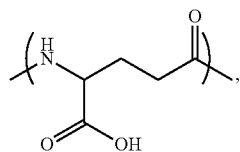

y is a mole fraction of the monomer unit represented by Formula (IV):

[Chem. 3]

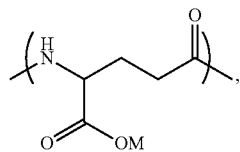

z is a mole fraction of the monomer unit represented by Formula (V):

[Chem. 4]

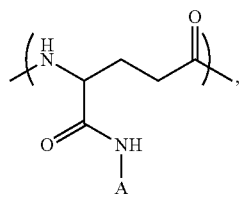

and
x, y, and z satisfy the following equations:

$0 \leq x < 1$;

$0 < y < 1$;

$0 < z < 1$; and $x + y + z = 1$;                                                         [Math. 1]

[10] the ionized graft copolymer according to [9], wherein the mole fraction x of the monomer unit represented by Formula (III) is 0;

[11] the ionized graft copolymer according to [9], wherein n is 50 to 10,000;

[12] the ionized graft copolymer according to [9], wherein the ionized graft copolymer has a hydrophobic parameter K of −15,000 to 0;

[13] a production method of nanoparticles containing an ionized graft copolymer of a poly(amino acid) selected from the group consisting of poly(γ-glutamic acid), poly(α-glutamic acid), and poly(aspartic acid) or a salt thereof and a hydrophobic primary amine compound represented by Formula (I): A-NH$_2$ [wherein A denotes a hydrophobic moiety] or a salt thereof, the method comprising the step of forming nanoparticles of the ionized graft copolymer produced with the production method according to [8];

[14] the production method of nanoparticles according to [13], comprising the steps of (1) condensing a poly(amino acid) selected from the group consisting of poly(γ-glutamic acid), poly(α-glutamic acid), and poly(aspartic acid) or a salt thereof and a hydrophobic primary amine compound represented by Formula (I): A-NH$_2$ [wherein A denotes a hydrophobic moiety] or a salt thereof;

(2) isolating a graft copolymer by allowing an acid to act on a condensate acquired at step (1);

(3) ionizing the graft copolymer by allowing a hydroxide of alkali metal, a carbonate of alkali metal, a hydrogencarbonate of alkali metal, a phosphate of alkali metal, a monohydrogen phosphate of alkali metal, a dihydrogen phosphate of alkali metal, an organic acid salt of alkali metal, or an acidic amino-acid salt of alkali metal to act on the graft copolymer isolated at step (2); and (4) forming nanoparticles of the ionized graft copolymer acquired at step (3);

[15] nanoparticles produced by the method according to [13], the nanoparticles containing an ionized graft copolymer of a poly(amino acid) selected from the group consisting of poly(γ-glutamic acid), poly(α-glutamic acid), and poly(aspartic acid) or a salt thereof and a hydrophobic primary amine compound represented by Formula (I): A-NH$_2$ [wherein A denotes a hydrophobic moiety] or a salt thereof;

[16] the nanoparticles according to [15], wherein the nanoparticles are used as an adjuvant; and

[17] a vaccine containing the nanoparticles according to [15].

Effect of the Invention

According to the present invention, a graft copolymer of a poly(amino acid) or a salt thereof and a hydrophobic primary amine compound or a salt thereof may be acquired in a shorter time at a higher yield than those of the conventional methods.

According to the present invention, nanoparticles containing the graft copolymer of a poly(amino acid) or a salt thereof and a hydrophobic primary amine compound or a salt thereof may be acquired with high efficiency and good reproducibility.

BRIEF DESCRIPTION OF DRAWINGS

FIG. 1 is a graph showing that nanoparticles of γ-PGA-PAE according to the present invention have excellent performance as an adjuvant for a vaccine.

MODES FOR CARRYING OUT THE INVENTION

A first aspect of the present invention relates to a graft copolymer of a poly(amino acid) selected from the group consisting of poly(γ-glutamic acid), poly(α-glutamic acid), and poly(aspartic acid) or a salt thereof and a hydrophobic primary amine compound represented by Formula (I): A-NH$_2$ [wherein A denotes a hydrophobic moiety] or a salt thereof, and a production method thereof.

The production method of the graft copolymer according to the first aspect of the present invention comprises the steps of:

(1) acquiring a graft copolymer by condensation of the poly(amino acid) or a salt thereof with the hydrophobic primary amine compound represented by Formula (I) or a salt thereof; and (2) isolating the graft copolymer by allowing an acid to act on the graft copolymer acquired at step (1).

In this description, a "poly(amino acid)" means an amino acid chain made up of a plurality of bonded amino acids.

Examples of amino acids making up a poly(amino acid) include glutamic acid (e.g., α-glutamic acid, γ-glutamic acid), aspartic acid, lysine, asparagine, arginine, and the like.

The constituent amino acids in the poly(amino acid) may be the L-isomers, the D-isomers, or the mixture thereof.

A bond between the constituent amino acids in the poly (amino acid) may be a peptide bond, a bond other than a peptide bond, such as an ester bond and an ether bond, or a bond via a linker such as glutaraldehyde and diisocyanate, and is typically a peptide bond.

In a preferred embodiment, the poly(amino acid) has a number average molecular weight of 1 to 20,000 kDa, preferably 20 kDa to 3,000 kDa. In this description, a molecular weight may be a relative molecular weight or an absolute molecular weight. For example, the relative molecular weight is a numerical value determined by a molecular weight measurement method using the following SEC-HPLC measurement: TSKgel α-M 300×7.8 mm I.D. (dual), 5 mM NaNO$_3$ DMSO:H$_2$O (9:1), 0.8 mL/minute, 40° C., RI detector, standard: pullulan (Shodex). The absolute molecular weight is a numerical value determined by a molecular weight measurement method using the following SEC-HPLC conditions: TSKgel GMPWXL, 300×7.8 mm I.D. (dual), 0.1 M NaNO$_3$, 0.8 mL/minute, 40° C., simultaneous detection by RI detector, viscometer, DLS detector, and SLS detector.

Specific examples of the poly(amino acid) include poly (γ-glutamic acid), poly(α-aspartic acid), poly(ε-lysine), poly (α-glutamic acid), and poly(α-lysine) and, among them, poly(γ-glutamic acid), poly(α-glutamic acid), and poly(α-aspartic acid) are preferable. Most preferably, the poly (amino acid) is poly(γ-glutamic acid).

Examples of the salt of the poly(amino acid) used in the present invention include, for example, a metal salt, an ammonium salt, a salt with an organic base, inorganic acid a salt with, a salt with an organic acid, a salt with a basic or acidic amino acid, and the like. Preferred examples of the metal salt include, for example, alkali metal salts such as a sodium salt and a potassium salt; alkaline earth metal salts such as a calcium salt, a magnesium salt, and a barium salt; aluminum salts, and the like. Preferred examples of the salt with an organic base include, for example, salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, N-methylmorpholine, N,N-diisopropylethylamine, 1,8-diazabicyclo[5.4.0]undec-7-ene (DBU), and the like. Preferred examples of the salt with an inorganic acid include, for example, salts with hydrochloric acid, hydrobromic acid, nitric acid, sulfuric acid, phosphoric acid, and the like. Preferred examples of the salt with an organic acid include, for example, salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, lactic acid, benzoic acid, and the like. Preferred examples of the salt with a basic amino acid include, for example, salts with arginine, lysine, ornithine, and the like, and preferred examples of the salt with an acidic amino acid include, for example, salts with aspartic acid, glutamic acid, and the like. Among them, preferable salts are pharmaceutically acceptable salts including a sodium salt, a potassium salt, and a lithium salt, and the sodium salt is particularly preferably.

In this description, in the hydrophobic primary amine compound represented by Formula (I): A-NH$_2$ [wherein A denotes a hydrophobic moiety], A- denoting the "hydrophobic moiety" means a derivative having an aromatic ring group such as a benzene ring, a derivative having a C$_{3-8}$ carbon chain, a derivative having a C$_{8-22}$ linear fatty chain, a derivative represented by R$^1$—(CHR$^2$)—, and a derivative represented by R$^3$—(CR$^4$R$^5$)—(CR$^6$R$^7$)—.

Examples of the "derivative having an aromatic ring group" represented by the A- include, for example, C$_{6-14}$ aryl groups that may have a substituent (e.g., phenyl, 1-naphthyl, 2-naphthyl, 1-anthryl, 2-anthryl, 9-anthryl), C$_{7-16}$ aralkyl groups that may have a substituent (e.g., benzyl, phenethyl, naphthylmethyl, phenylpropyl), and aromatic heterocyclic groups that may have a substituent, and the like.

Examples of the aromatic heterocyclic groups of the "aromatic heterocyclic groups that may have a substituent" include, for example, 5- to 14-membered (preferably, 5- to 10-membered) aromatic heterocyclic groups containing 1 to 4 heteroatoms as annular atoms selected from nitrogen atoms, sulfur atoms, and oxygen atoms in addition to carbon atoms.

Preferred examples of the "aromatic heterocyclic groups" include:

5- to 6-membered monocyclic aromatic heterocyclic groups such as thienyl, furyl, pyrrolyl, imidazolyl, pyrazolyl, thiazolyl, isothiazolyl, oxazolyl, isooxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, and triazinyl; and 8- to 14-membered condensed polycyclic (preferably, bicyclic or tricyclic) aromatic heterocyclic groups such as benzothiophenyl, benzofuranyl, benzoimidazolyl, benzooxazolyl, benzoisooxazolyl, benzothiazolyl, benzoisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, and phenoxazinyl.

The number of substituents at substitutable positions of the "$C_{6-14}$ aryl group that may have a substituent" represented by the A- is, for example, 1 to 5, preferably 1 to 3. If the number of substituents is not less than 2, the substituents may be the same or different.

The substituents may be selected from $C_{1-6}$ alkyl groups that may be halogenated (e.g., methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl), $C_{6-14}$ aryl groups (e.g., phenyl, 1-naphthyl, 2-naphthyl, 1-anthryl, 2-anthryl, 9-anthryl), $C_{7-16}$ aralkyl groups (e.g., benzyl, phenethyl, naphthylmethyl, phenylpropyl), and the following Substituent Group a.

[Substituent Group a]
(1) halogen atoms (e.g., fluorine, chlorine, bromine, iodine),
(2) nitro groups,
(3) cyano groups,
(4) hydroxy groups,
(5) $C_{1-6}$ alkoxy groups that may be halogenated (e.g., methoxy, ethoxy, propoxy, isopropoxy, butoxy, isobutoxy, sec-butoxy, tert-butoxy, pentyloxy, hexyloxy),
(6) $C_{6-14}$ aryloxy groups (e.g., phenoxy, naphthoxy),
(7) $C_{7-16}$ aralkyloxy groups (e.g., benzyloxy),
(8) 5- to 14-membered aromatic heterocyclic oxy groups (e.g., pyridyloxy),
(9) 3- to 14-membered non-aromatic heterocyclic oxy groups (e.g., morpholinyloxy, piperidinyloxy),
(10) $C_{1-6}$ alkyl-carbonyloxy groups (e.g., acetoxy, propanoyloxy),
(11) $C_{6-14}$ aryl-carbonyloxy groups (e.g., benzoyloxy, 1-naphthoyloxy, 2-naphthoyloxy),
(12) $C_{1-6}$ alkoxy-carbonyloxy groups (e.g., methoxycarbonyloxy, ethoxycarbonyloxy, propoxycarbonyloxy, butoxycarbonyloxy),
(13) mono- or di-$C_{1-6}$ alkyl-carbamoyloxy groups (e.g., methylcarbamoyloxy, ethylcarbamoyloxy, dimethylcarbamoyloxy, diethylcarbamoyloxy),
(14) $C_{6-14}$ aryl-carbamoyloxy groups (e.g., phenylcarbamoyloxy, naphthylcarbamoyloxy),
(15) 5- to 14-membered aromatic heterocyclic carbonyloxy groups (e.g., nicotinoyloxy),
(16) 3- to 14-membered non-aromatic heterocyclic carbonyloxy groups (e.g., morpholinylcarbonyloxy, piperidinylcarbonyloxy),
(17) $C_{1-6}$ alkylsulfonyloxy groups that may be halogenated (e.g., methylsulfonyloxy, trifluoromethylsulfonyloxy),
(18) $C_{6-14}$ arylsulfonyloxy groups that may be substituted with $C_{1-6}$ alkyl groups (e.g., phenylsulfonyloxy, toluenesulfonyloxy),
(19) $C_{1-6}$ alkylthio groups that may be halogenated (e.g., methylthio, ethylthio, propylthio, isopropylthio, butylthio, sec-butylthio, tert-butylthio, pentylthio, hexylthio),
(20) 5- to 14-membered aromatic heterocyclic groups (including, e.g., 5- to 6-membered monocyclic aromatic heterocyclic groups such as thienyl, furyl, pyrrolyl, imidazolyl, pyrazolyl, thiazolyl, isothiazolyl, oxazolyl, isooxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, and triazinyl; and 8- to 14-membered condensed polycyclic (preferably, bicyclic or tricyclic) aromatic heterocyclic groups such as benzothiophenyl, benzofuranyl, benzoimidazolyl, benzooxazolyl, benzoisooxazolyl, benzothiazolyl, benzoisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, and phenoxazinyl),

(21) 3- to 14-membered non-aromatic heterocyclic groups (including, e.g., 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, and diazocanyl; and 9- to 14-membered condensed polycyclic (preferably, bicyclic or tricyclic) non-aromatic heterocyclic groups such as dihydrobenzofuranyl, dihydrobenzoimidazolyl, dihydrobenzooxazolyl, dihydrobenzothiazolyl, dihydrobenzoisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzoazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacridinyl, tetrahydrophenazinyl, tetrahydrothioxanthenyl, and octahydroisoquinolyl),

(22) $C_{1-6}$ alkyl-carbonyl groups that may be halogenated (e.g., acetyl, chloroacetyl, trifluoroacetyl, trichloroacetyl, propanoyl, butanoyl, pentanoyl, hexanoyl),
(23) $C_{6-14}$ aryl-carbonyl groups (e.g., benzoyl, 1-naphthoyl, 2-naphthoyl),
(24) 5- to 14-membered aromatic heterocyclic carbonyl groups (e.g., nicotinoyl, isonicotinoyl, thenoyl, furoyl),
(25) 3- to 14-membered non-aromatic heterocyclic carbonyl groups (e.g., morpholinylcarbonyl, piperidinylcarbonyl, pyrrolidinylcarbonyl),
(26) $C_{1-6}$ alkoxy-carbonyl groups (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl),
(27) $C_{6-14}$ aryloxy-carbonyl groups (e.g., phenyloxycarbonyl, 1-naphthyloxycarbonyl, 2-naphthyloxycarbonyl),

(28) $C_{7-16}$ aralkyloxy-carbonyl groups (e.g., benzyloxycarbonyl, phenethyloxycarbonyl),
(29) carboxy groups,
(30) carbamoyl groups,
(31) mono- or di-$C_{1-6}$ alkyl-carbamoyl groups (e.g., methylcarbamoyl, ethylcarbamoyl, dimethylcarbamoyl, diethylcarbamoyl, N-ethyl-N-methylcarbamoyl),
(32) $C_{6-14}$ aryl-carbamoyl groups (e.g., phenylcarbamoyl),
(33) 5- to 14-membered aromatic heterocyclic carbamoyl groups (e.g., pyridylcarbamoyl, thienylcarbamoyl),
(34) 3- to 14-membered non-aromatic heterocyclic carbamoyl groups (e.g., morpholinylcarbamoyl, piperidinylcarbamoyl),
(35) $C_{1-6}$ alkylsulfonyl groups that may be halogenated (methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl, hexylsulfonyl),
(36) $C_{6-14}$ arylsulfonyl groups (e.g., phenylsulfonyl, 1-naphthylsulfonyl, 2-naphthylsulfonyl),
(37) 5- to 14-membered aromatic heterocyclic sulfonyl groups (e.g., pyridylsulfonyl, thienylsulfonyl),
(38) $C_{1-6}$ alkylsulfinyl groups that may be halogenated (e.g., methylsulfinyl, ethylsulfinyl),
(39) $C_{6-14}$ arylsulfinyl groups (e.g., phenylsulfinyl, 1-naphthylsulfinyl, 2-naphthylsulfinyl),
(40) 5- to 14-membered aromatic heterocyclic sulfinyl groups (e.g., pyridylsulfinyl, thienylsulfinyl),
(41) mono- or di-$C_{1-6}$ alkylamino groups (e.g., methylamino, ethylamino, propylamino, isopropylamino, butylamino, dimethylamino, diethylamino, dipropylamino, dibutylamino, N-ethyl-N-methylamino),
(42) mono- or di-$C_{6-14}$ arylamino groups (e.g., phenylamino),
(43) 5- to 14-membered aromatic heterocyclic amino groups (e.g., pyridylamino),
(44) $C_{7-16}$ aralkylamino groups (e.g., benzylamino),
(45) formylamino groups,
(46) $C_{1-6}$ alkyl-carbonylamino groups (e.g., acetylamino, propanoylamino, butanoylamino),
(47) ($C_{1-6}$ alkyl)($C_{1-6}$ alkyl-carbonyl) amino groups (e.g., N-acetyl-N-methylamino),
(48) $C_{6-14}$ aryl-carbonylamino groups (e.g., phenylcarbonylamino, naphthylcarbonylamino),
(49) $C_{1-6}$ alkoxy-carbonylamino groups (e.g., methoxycarbonylamino, ethoxycarbonylamino, propoxycarbonylamino, butoxycarbonylamino, tert-butoxycarbonylamino),
(50) $C_{7-16}$ aralkyloxy-carbonylamino groups (e.g., benzyloxycarbonylamino),
(51) $C_{1-6}$ alkylsulfonylamino groups (e.g., methylsulfonylamino, ethylsulfonylamino),
(52) $C_{6-14}$ arylsulfonylamino groups that may be substituted with $C_{1-6}$ alkyl groups (e.g., phenylsulfonylamino, toluenesulfonylamino),
(53) amino groups,
(54) $C_{2-6}$ alkenyl groups (e.g., ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl),
(55) $C_{2-6}$ alkynyl groups (e.g., ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 4-methyl-2-pentynyl),
(56) $C_{3-10}$ cycloalkyl group (e.g., cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, adamantyl),
(57) $C_{3-10}$ cycloalkenyl groups (e.g., cyclopropenyl, cyclobutenyl, cyclopentenyl, cyclohexenyl, cycloheptenyl, cyclooctenyl),
(58) $C_{1-6}$ cycloalkoxy-carbonyl groups (e.g., cyclopentoxy)
(59) $C_{7-16}$ aralkylthio groups (e.g., S-benzylthio)
(60) mercapto groups,
(61) sulfo groups, and
(62) guanidino groups.

The number of substituents at substitutable positions of the "$C_{7-16}$ aralkyl group that may have a substituent" represented by the A- is, for example, 1 to 5, preferably 1 to 3. If the number of substituents is not less than 2, the substituents may be the same or different.

The substituents may be selected from the Substituent Group a.

The number of substituents at substitutable positions of the "aromatic heterocycle group that may have a substituent" represented by the A- is, for example, 1 to 5, preferably 1 to 3. If the number of substituents is not less than 2, the substituents may be the same or different.

The substituents may be selected from $C_{1-6}$ alkyl groups that may be halogenated (e.g., methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl), $C_{6-14}$ aryl groups (e.g., phenyl, 1-naphthyl, 2-naphthyl, 1-anthryl, 2-anthryl, 9-anthryl), $C_{7-16}$ aralkyl groups (e.g., benzyl, phenethyl, naphthylmethyl, phenylpropyl), and the Substituent Group a.

Examples of the "derivative having a $C_{3-6}$ carbon chain" represented by the A- include, for example, $C_{34}$ alkyl groups that may have a substituent (e.g., propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl), $C_{3-10}$ cycloalkyl groups (e.g., cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, adamantyl), and the like.

Examples of the "$C_{3-8}$ alkyl groups" of the "$C_{3-8}$ alkyl groups that may have a substituent" represented by the A- are preferably propyl, isopropyl, butyl, isobutyl, sec-butyl, tert-butyl, pentyl, and isopentyl.

The number of substituents at substitutable positions of the "$C_{3-8}$ alkyl group that may have a substituent" represented by the A- is, for example, 1 to 5, preferably 1 to 3. If the number of substituents is not less than 2, the substituents may be the same or different.

The substituents may be selected from $C_{6-14}$ aryl groups (e.g., phenyl, 1-naphthyl, 2-naphthyl, 1-anthryl, 2-anthryl, 9-anthryl), and the Substituent Group a.

Examples of the substituent of the "$C_{3-8}$ alkyl groups that may have a substituent" represented by the A- are, preferably hydroxy groups, mercapto groups, amino groups, $C_{6-14}$ aryl groups, $C_{7-16}$ aralkylthio groups, guanidino groups, $C_{1-6}$ alkylthio groups that may be halogenated, $C_{1-6}$ alkoxy-carbonyl groups, $C_{1-6}$ cycloalkoxy-carbonyl groups, $C_{7-16}$ aralkyloxy-carbonyl groups, carboxy groups, and carbamoyl groups.

Examples of the "derivative having a $C_{8-22}$ linear fatty chain" represented by the A- include, for example, linear $C_{8-22}$ alkyl groups (e.g., octyl, nonyl, decyl, undecyl, dodecyl, tridecyl, tetradecyl, pentadecyl, hexadecyl, heptadecyl, octadecyl, nonadecyl, eicosyl, heneicosylidene, docosyl) and the like.

$R^1$ of the "derivative represented by $R^1$—(CHR$^2$)—" may be selected from a hydrogen atom or may be selected from the following Substituent Group b.

[Substituent Group b]
(1) halogen atoms,
(2) cyano groups,
(3) hydroxy groups,
(4) $C_{1-6}$ alkoxy groups that may have a substituent (e.g., methoxy, ethoxy, propoxy, isopropoxy, butoxy, isobutoxy, sec-butoxy, tert-butoxy, pentyloxy, hexyloxy),
(5) $C_{6-14}$ aryloxy groups that may have a substituent (e.g., phenoxy, naphthoxy),
(6) $C_{7-16}$ aralkyloxy groups that may have a substituent (e.g., benzyloxy),
(7) $C_{1-6}$ alkyl-carbonyloxy groups that may have a substituent (e.g., acetoxy, propanoyloxy),
(8) $C_{1-6}$ alkyl-carbonyl groups that may have a substituent (e.g., acetyl, chloroacetyl, trifluoroacetyl, trichloroacetyl, propanoyl, butanoyl, pentanoyl, hexanoyl),
(9) $C_{6-14}$ aryl-carbonyl groups that may have a substituent (e.g., benzoyl, 1-naphthoyl, 2-naphthoyl),
(10) 5- to 14-membered aromatic heterocyclic carbonyl groups that may have a substituent (e.g., nicotinoyl, isonicotinoyl, thenoyl, furoyl),
(11) 3- to 14-membered non-aromatic heterocyclic carbonyl groups that may have a substituent (e.g., morpholinylcarbonyl, piperidinylcarbonyl, pyrrolidinylcarbonyl),
(12) $C_{1-6}$ alkoxy-carbonyl groups that may have a substituent (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl),
(13) $C_{6-14}$ aryloxy-carbonyl groups that may have a substituent (e.g., phenyloxycarbonyl, 1-naphthyloxycarbonyl, 2-naphthyloxycarbonyl),
(14) $C_{7-16}$ aralkyloxy-carbonyl groups that may have a substituent (e.g., benzyloxycarbonyl, phenethyloxycarbonyl),
(15) carboxy groups,
(16) carbamoyl groups,
(17) mono- or di-$C_{1-6}$ alkyl-carbamoyl groups that may have a substituent (e.g., methylcarbamoyl, ethylcarbamoyl, dimethylcarbamoyl, diethylcarbamoyl, N-ethyl-N-methylcarbamoyl),
(18) $C_{6-14}$ aryl-carbamoyl groups that may have a substituent (e.g., phenylcarbamoyl),
(19) $C_{1-6}$ alkylthio groups that may have a substituent (e.g., methylthio, ethylthio, propylthio, isopropylthio, butylthio, sec-butylthio, tert-butylthio, pentylthio, hexylthio),
(20) $C_{1-6}$ alkylsulfonyl groups that may have a substituent (methylsulfonyl, ethylsulfonyl, propylsulfonyl, isopropylsulfonyl, butylsulfonyl, pentylsulfonyl, hexylsulfonyl),
(21) $C_{1-6}$ alkylsulfinyl groups that may have a substituent (e.g., methylsulfinyl, ethylsulfinyl),
(22) mono- or di-$C_{1-6}$ alkylamino groups that may have a substituent (e.g., methylamino, ethylamino, propylamino, isopropylamino, butylamino, dimethylamino, diethylamino, dipropylamino, dibutylamino, N-ethyl-N-methylamino),
(23) mono- or di-$C_{6-14}$ arylamino groups that may have a substituent (e.g., phenylamino),
(24) $C_{1-6}$ alkyl-carbonylamino groups that may have a substituent (e.g., acetylamino, propanoylamino, butanoylamino),
(25) $C_{6-14}$ aryl-carbonylamino groups that may have a substituent (e.g., phenylcarbonylamino, naphthylcarbonylamino),
(26) $C_{1-6}$ alkoxy-carbonylamino groups that may have a substituent (e.g., methoxycarbonylamino, ethoxycarbonylamino, propoxycarbonylamino, butoxycarbonylamino, tert-butoxycarbonylamino),
(27) $C_{7-16}$ aralkyloxy-carbonylamino groups that may have a substituent (e.g., benzyloxycarbonylamino),
(28) 5 to 14-membered aromatic heterocyclic groups that may have a substituent (including, e.g., 5- to 6-membered monocyclic aromatic heterocyclic groups such as thienyl, furyl, pyrrolyl, imidazolyl, pyrazolyl, thiazolyl, isothiazolyl, oxazolyl, isooxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, and triazinyl; and 8- to 14-membered condensed polycyclic (preferably, bicyclic or tricyclic) aromatic heterocyclic groups such as benzothiophenyl, benzofuranyl, benzoimidazolyl, benzooxazolyl, benzoisooxazolyl, benzothiazolyl, benzoisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, and phenoxazinyl),
(29) $C_{6-14}$ aryl groups that may have a substituent (e.g., phenyl, 1-naphthyl, 2-naphthyl, 1-anthryl, 2-anthryl, 9-anthryl),
(30) $C_{7-16}$ aralkylthio groups (e.g., S-benzylthio),
(31) sulfo groups, and
(32) mercapto groups.

A substituent may be selected from the Substituent Group a for each of the respective substituents of the $C_{1-6}$ alkoxy groups that may have a substituent, the $C_{6-14}$ aryloxy groups that may have a substituent, the $C_{7-16}$ aralkyloxy groups that may have a substituent, the $C_{1-6}$ alkyl-carbonyloxy groups that may have a substituent, the $C_{1-6}$ alkyl-carbonyl groups that may have a substituent, the $C_{6-14}$ aryl-carbonyl groups that may have a substituent, the 5- to 14-membered aromatic heterocyclic carbonyl groups that may have a substituent, the 3- to 14-membered non-aromatic heterocyclic carbonyl groups that may have a substituent, the $C_{1-6}$ alkoxy-carbonyl groups that may have a substituent, the $C_{6-14}$ aryloxy-carbonyl groups that may have a substituent, the $C_{7-16}$ aralkyloxy-carbonyl groups that may have a substituent, the mono- or di-$C_{1-6}$ alkyl-carbamoyl groups that may have a substituent, the $C_{6-14}$ aryl-carbamoyl groups that may have a substituent, the $C_{1-6}$ alkylthio groups that may have a substituent, the $C_{1-6}$ alkylsulfonyl groups that may have a substituent, the $C_{1-6}$ alkylsulfinyl groups that may have a substituent, the mono- or di-$C_{1-6}$ alkylamino groups that may have a substituent, the mono- or di-$C_{6-14}$ arylamino groups that may have a substituent, the $C_{1-6}$ alkyl-carbonylamino groups that may have a substituent, the $C_{6-14}$ aryl-carbonylamino groups that may have a substituent, the $C_{1-6}$ alkoxy-carbonylamino groups that may have a substituent, the $C_{7-16}$ aralkyloxy-carbonylamino groups that may have a substituent, the 5 to 14-membered aromatic heterocyclic groups that may have a substituent, and $C_{6-14}$ aryl groups that may have a substituent in the [Substituent Group b].

$R^1$ of the "derivative represented by $R^1$—(CHR$^2$)—" is preferably a hydrogen atom and a $C_{6-14}$ aryl group that may have a substituent, more preferably phenyl.

$R^2$ of the "derivative represented by $R^1$—(CHR$^2$)—" may be selected from the following Substituent Group c.

[Substituent Group c]
(1) $C_{1-6}$ alkoxy-carbonyl groups (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl),
(2) $C_{1-6}$ cycloalkoxy-carbonyl groups (e.g., cyclopentoxy)
(3) $C_{6-14}$ aryloxy-carbonyl groups (e.g., phenyloxycarbonyl, 1-naphthyloxycarbonyl, 2-naphthyloxycarbonyl),
(4) $C_{7-16}$ aralkyloxy-carbonyl groups (e.g., benzyloxycarbonyl, phenethyloxycarbonyl),
(5) carboxy groups,
(6) carbamoyl groups,
(7) mono- or di-$C_{1-6}$ alkyl-carbamoyl groups (e.g., methylcarbamoyl, ethylcarbamoyl, dimethylcarbamoyl, diethylcarbamoyl, N-ethyl-N-methylcarbamoyl), and
(8) $C_{6-14}$ aryl-carbamoyl groups (e.g., phenylcarbamoyl).

$R^2$ of the "derivative represented by $R^1$—(CHR$^2$)—" is preferably a $C_{1-6}$ alkoxy-carbonyl group, a $C_{1-6}$ cycloalkoxy-carbonyl group, a $C_{7-16}$ aralkyloxy-carbonyl group, a carboxy group, a carbamoyl group, more preferably a $C_{1-6}$ alkoxy-carbonyl group, and most preferably ethoxycarbonyl.

$R^3$ of the "derivative represented by $R^3$—(CR$^4$R$^5$)—(CR$^6$R$^7$)—" may be selected from a hydrogen atom or the Substituent Group b.

$R^3$ of the "derivative represented by $R^3$—(CR$^4$R$^5$)—(CR$^6$R$^7$)—" is preferably a hydrogen atom, a hydroxy group, a mercapto group, an amino group, a 5- to 14-membered aromatic heterocyclic group that may have a substituent, a $C_{7-16}$ aralkylthio group, and a $C_{6-14}$ aryl group that may have a substituent, more preferably, a hydrogen atom, a hydroxy group, a mercapto group, an amino group, imidazolyl that may have a substituent, indolyl that may have a substituent, S-benzylthio, and phenyl that may have a substituent, particularly preferably indolyl, S-benzylthio, and phenyl that may have a substituent. Phenyl is most preferable.

$R^4$ and $R^5$ of the "derivative represented by $R^3$—(CR$^4$R$^5$)—(CR$^6$R$^7$)—" may independently be selected from a hydrogen atom or the Substituent Group a.

$R^4$ and $R^5$ of the "derivative represented by $R^3$—(CR$^4$R$^5$)—(CR$^6$R$^7$)—" are preferably hydrogen atoms.

$R^6$ of the "derivative represented by $R^3$—(CR$^4$R$^5$)—(CR$^6$R$^7$)—" may be selected from a hydrogen atom or the following Substituent Group d.

[Substituent Group d]
(1) hydroxy groups,
(2) $C_{1-6}$ alkyl groups that may be halogenated (e.g., methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl),
(3) $C_{3-10}$ cycloalkyl groups (e.g., cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, adamantyl), (4) 5- to 14-membered aromatic heterocyclic groups that may have a substituent (including, e.g., 5- to 6-membered monocyclic aromatic heterocyclic groups such as thienyl, furyl, pyrrolyl, imidazolyl, pyrazolyl, thiazolyl, isothiazolyl, oxazolyl, isooxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, and triazinyl; and 8- to 14-membered condensed polycyclic (preferably, bicyclic or tricyclic) aromatic heterocyclic groups such as benzothiophenyl, benzofuranyl, benzoimidazolyl, benzooxazolyl, benzoisooxazolyl, benzothiazolyl, benzoisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, and phenoxazinyl), and (5) $C_{6-14}$ aryl groups that may have a substituent (e.g., phenyl, 1-naphthyl, 2-naphthyl, 1-anthryl, 2-anthryl, 9-anthryl).

A substituent may be selected from the Substituent Group a for each of the respective substituents of the 5- to 14-membered aromatic heterocyclic groups that may have a substituent, and the $C_{6-14}$ aryl groups that may have a substituent in the [Substituent Group d].

$R^6$ of the "derivative represented by $R^3$—(CR$^4$R$^5$)—(CR$^6$R$^7$)—" is preferably a hydrogen atom and methyl, and most preferably a hydrogen atom.

$R^7$ of the "derivative represented by $R^3$—(CR$^4$R$^5$)—(CR$^6$R$^7$)—" may be selected from the Substituent Group c.

$R^7$ of the "derivative represented by $R^3$—(CR$^4$R$^5$)—(CR$^6$R$^7$)—" is preferably a $C_{1-6}$ alkoxy-carbonyl group, a $C_{1-6}$ cycloalkoxy-carbonyl group, a $C_{7-16}$ aralkyloxy-carbonyl group, a carboxy group, a carbamoyl group, more preferably a $C_{1-6}$ alkoxy-carbonyl group, most preferably ethoxycarbonyl.

The "A-" is preferably the derivative having a $C_{3-8}$ carbon chain, the derivative represented by $R^1$—(CHR$^2$)—, and the derivative represented by $R^3$—(CR$^4$R$^5$)—(CR$^6$R$^7$)—, and more preferably, the derivative represented by $R^3$—(CR$^4$R$^5$)—(CR$^6$R$^7$)—.

A hydrophobic primary amine compound represented by Formula (I): A-NH$_2$ [wherein A denotes a hydrophobic moiety] is preferably an α-amino acid derivative that may have a substituent. The amino acid may be the L-isomer, the D-isomer, or the mixture thereof.

Examples of the "α-amino acid" of the "α-amino acid that may have a substituent" used in the present invention include, for example, alanine, arginine, asparagine, aspartic acid, cysteine, glutamine, glutamic acid, 2-aminomalonic acid, 2-aminoadipic acid, glycine, histidine, isoleucine, leucine, lysine, ornithine, 2,4-diaminobutyric acid, methionine, phenylalanine, serine, threonine, tryptophan, 5-methyltryptophan, tyrosine, valine, alloisoleucine, norvaline, norleucine, tert-leucine, γ-methylleucine, phenylglycine, 2-aminobutyric acid, cysteic acid, homocysteic acid, 1-naphthylalanine, 2-naphthylalanine, 2-thienylglycine, 3-thienylglycine, 3-benzothienylalanine, 4-biphenylalanine, pentamethylphenylalanine, 1-aminocyclopropane-1-carboxylic acid, 1-aminocyclobutane-1-carboxylic acid, 1-aminocyclopentane-1-carboxylic acid, 1-aminocyclohexane-1- carboxylic acid, 1-aminocycloheptane-1-carboxylic acid, and the like. The "α-amino acid" is preferably phenylalanine, phenylglycine, isoleucine, leucine, tyrosine, tryptophan, cysteine, serine, and threonine. Phenylalanine is particularly preferable.

The "α-amino acid" used in the present invention may have 1 to 3 substituents at substitutable positions. Examples of the substituents include halogen atoms, nitro groups, $C_{1-6}$ alkyl groups that may be substituted with 1 to 3 halogen atoms, $C_{7-13}$ aralkyl groups that may be substituted with 1 to 3 halogen atoms (e.g., benzyl), $C_{1-6}$ alkoxy groups, and the like.

In this description, a "derivative" means a compound and a characteristic group generated by changing a small part in a molecule of a certain compound by introduction of a function group, oxidation, reduction, substitution of atoms, and specific examples include, for example, carboxylic acid, $C_{1-18}$ alkyl ester, $C_{6-18}$ aromatic ester, $C_{3-18}$ cycloalkyl ester, $C_{1-18}$ alkyl monosubstituted amide, $C_{1-18}$ alkyl disubstituted amide, unsubstituted amide, and the like of a certain compound. Examples of the $C_{1-18}$ alkyl substituents include methyl, ethyl, n-propyl, i-propyl, cyclopropyl, n-butyl, sec-butyl, t-butyl, cyclopropylmethyl, cyclobutyl, n-pentyl, 1-methylbutyl, 2-methylbutyl, 3-methylbutyl, 2,2-dimethylpropyl, 2,3-dimethylpropyl, 3,3-dimethylpropyl, cyclopropylethyl, cyclobutylmethyl, cyclopropyl, n-hexyl, n-heptyl, n-octyl, n-nonanyl, n-decanyl, n-hexadecanyl, n-octadecanyl, and the like.

The "derivative" may include substitution with halogen atoms such as fluorine, chlorine, bromine, and iodine, or nitro groups and the like.

The "derivative" used in the present invention is preferably $C_{1-18}$ alkyl ester.

The α-amino acid derivative is preferably a phenylalanine derivative and is preferably phenylalanine alkyl ester, particularly, phenylalanine ethyl ester. The amino acid derivative may be the L-isomers, the D-isomers, or the mixture thereof.

Examples of the salt of the hydrophobic primary amine compound represented by Formula (I) include the same salts as those illustrated as the salt of the poly(amino acid).

In this description, the "graft copolymer" refers to a graft copolymer represented by Formula (VI):

[Chem. 5]

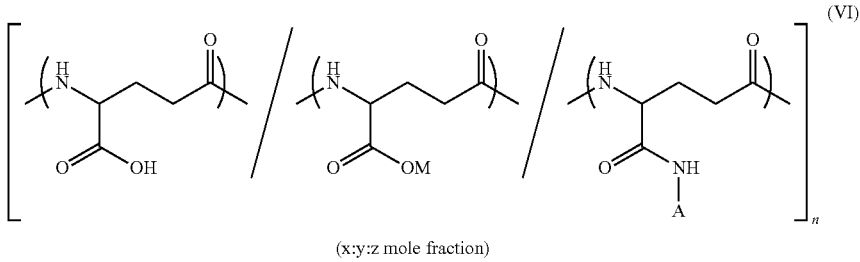

(x:y:z mole fraction)

[wherein M is alkali metal, A is a hydrophobic moiety, and n is an integer from 10 to 100,000, diagonal lines intervening three monomer units represent that the monomer units are arranged in irregular order; and x is a mole fraction of the monomer unit represented by Formula (III):

[Chem. 6]

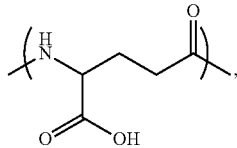

(III)

y is a mole fraction of the monomer unit represented by Formula (IV):

[Chem. 7]

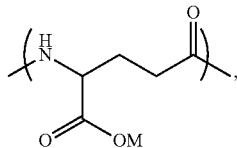

(IV)

z is a mole fraction of the monomer unit represented by Formula (V):

[Chem. 8]

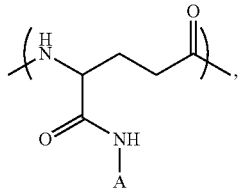

(V)

x, y, and z satisfy the following equations:

$0 \leq x < 1;$ $0 \leq y < 1;$ $0 < z < 1;$ and $x+y+z=1$]

[Math. 2]

An amount of the hydrophobic primary amine compound or a salt thereof represented by Formula (I) used at step (1) is typically 0.01 to 5 equivalents, preferably 0.1 to 1.5 equivalents, relative to the poly(amino acid).

Examples of a condensing agent used at step (1) include a condensing agent used in usual peptide synthesis and include, for example, water-soluble carbodiimide hydrochloride [e.g., 1-ethyl-3-(3-dimethylaminopropyl)carbodiimide hydrochloride] (WSC.HCl), 4-(4,6-dimethoxy-1,3,5-triazin-2-yl)-4-methylmorpholinium chloride n-hydrate (DMT-MM), N,N,N',N'-tetramethyl-O—(N-succinimidyl)uroniumtetrafluoroborate (TSTU), 2-(5-norbornene-2,3-dicarboximide)-1,1,3,3-tetramethyluroniumtetrafluoroborate (TNTU), and the like.

An amount of the condensing agent used at step (1) is typically 0.01 to 5 equivalents, preferably 0.1 to 1.5 equivalents, relative to the poly(amino acid).

Step (1) is performed in a solvent not affecting a reaction. Examples of such a solvent include, for example, water, a mixture of an organic solvent described below and water, and the like. Examples of the organic solvent include $C_{1-3}$ alcohol (e.g., methanol, ethanol, isopropanol, n-propanol), dimethylsulfoxide (DMSO), tetrahydrofuran (THF), N,N-dimethylformamide (DMF), N,N-dimethylacetamide (DMAc), N-methylpyrrolidone (NMP), aprotic solvents with high polarity such as acetonitrile, and the like.

If the poly(amino acid) is a free form, a base or a salt thereof is added at step (1). Examples of the base used in this case include alkali metal salts, carbonates, hydrogencarbonates, organic bases, and the like.

If an alkali metal salt is used as the base at step (1), examples thereof include sodium hydroxide, potassium hydroxide, lithium hydroxide, and the like, and sodium hydroxide is preferable.

If a carbonate is used as the base at step (1), examples thereof include lithium carbonate, sodium carbonate, potassium carbonate, and the like, and sodium carbonate is preferable.

If a hydrogencarbonate is used as the base at step (1), examples thereof include, for example, lithium hydrogencarbonate, sodium hydrogencarbonate, potassium hydrogencarbonate, and the like, and sodium hydrogencarbonate is preferable.

If an organic base is used as the base at step (1), for example, trimethylamine, triethylamine, pyridine, picoline, triethanolamine, N-methylmorpholine, N,N-diisopropylethylamine, 1,8-diazabicyclo[5.4.0]undec-7-ene (DBU) may be used as needed.

An amount of the base or a salt thereof used at step (1) is typically 0.01 to 100 equivalents, preferably 0.3 to 10 equivalents, more preferably 0.5 to 1.5 equivalents, relative to the poly(amino acid).

If the poly(amino acid) is the salt described above or a sodium salt, the poly(amino acid) may directly be used for the reaction.

A reaction temperature of step (1) is typically −30 to 80° C., preferably −5 to 45° C., more preferably −5 to 30° C.

A reaction time of step (1) is typically from 0.5 hours to 7 days, preferably from 1 hour to 2 days.

The graft copolymer acquired at step (1) may be subjected to known purification means for concentration, extraction, chromatography, ultrafiltration, centrifugal concentration, and the like or may directly be used at the next step.

"Allowing an acid to act" at step (2) means that a deprotonated carboxyl group (—COO⁻) contained in the graft copolymer is protonated into the state of a carboxyl group (—COOH) by adding the acid.

Examples of the acid used at step (2) include inorganic acids such as hydrochloric acid, hydrobromic acid, nitric acid, sulfuric acid, and phosphoric acid; and organic acids such as formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, lactic acid, and benzoic acid and, among them, hydrochloric acid, hydrobromic acid, and acetic acid are preferable.

Step (2) is typically performed in a solvent not affecting a reaction. Examples of such a solvent include, for example, water, a mixture of an organic solvent described below and water, and the like. Examples of the organic solvent include $C_{1-3}$ alcohol, dimethylsulfoxide (DMSO), tetrahydrofuran (THF), N,N-dimethylformamide (DMF), N,N-dimethylacetamide (DMAc), N-methylpyrrolidone (NMP), aprotic solvents with high polarity such as acetonitrile, and the like. Alternatively, step (2) may be performed without a solvent.

A reaction temperature of step (2) is typically −5 to 80° C., preferably −5 to 30° C.

In another preferable embodiment, a reaction temperature of step (2) is 0 to 80° C.

This reaction may be conducted under an elevated temperature condition or a lowered temperature condition as long as the temperature is within the temperature ranges.

The reaction temperature of this reaction is more preferably 40 to 70° C.

In this description, a "room temperature" is 1 to 30° C. unless otherwise stated.

A reaction time of step (2) is typically from 0.5 hours to 7 days, preferably from 1 hour to 2 days.

In a preferred embodiment, the reaction is preferably conducted by using hydrochloric acid at 60° C.

In the method, an introduction rate of the hydrophobic primary amine compound represented by Formula (I) relative to the poly(amino acid) is preferably 1 to 99%, more preferably 5 to 85%.

The poly(amino acid) is preferably poly(γ-glutamic acid).

The hydrophobic primary amine compound represented by Formula (I) is preferably α-amino acid derivatives, particularly preferably, phenylalanine derivatives, and phenylalanine ethyl ester is especially preferable.

A number average molecular weight of the graft copolymer acquired in this way is 1 to 2000 kDa, preferably 10 to 1000 kDa.

A second aspect of the present invention relates to an ionized graft copolymer of a poly(amino acid) selected from the group consisting of poly(γ-glutamic acid), poly(α-glutamic acid), and poly(aspartic acid) or a salt thereof and a hydrophobic primary amine compound represented by Formula (I): A-NH$_2$ [wherein A denotes a hydrophobic moiety] or a salt thereof, and a production method thereof.

The production method of the ionized graft copolymer according to the second aspect of the present invention comprises the step of:

ionizing the graft copolymer by allowing a hydroxide of alkali metal, a carbonate of alkali metal, a hydrogencarbonate of alkali metal, a phosphate of alkali metal, a monohydrogen phosphate of alkali metal, a dihydrogen phosphate of alkali metal, an organic acid salt of alkali metal, or an acidic amino-acid salt of alkali metal to act on the graft copolymer of the poly(amino acid) or a salt thereof and the hydrophobic primary amine compound or a salt thereof.

The graft copolymer of a poly(amino acid) or a salt thereof and a hydrophobic primary amine compound or a salt thereof used as a raw material at the step may be produced in conformity to the method of producing the graft copolymer of a poly(amino acid) or a salt thereof and a hydrophobic primary amine compound or a salt thereof described above or the method described in Patent Document 3.

The poly(amino acid) or a salt thereof is preferably poly(γ-glutamic acid).

The hydrophobic primary amine compound represented by Formula (I) is preferably α-amino acid derivatives, particularly preferably, phenylalanine derivatives, and phenylalanine ethyl ester is especially preferable.

At this step, "allowing a hydroxide of alkali metal, a carbonate of alkali metal, a hydrogencarbonate of alkali metal, a phosphate of alkali metal, a monohydrogen phosphate of alkali metal, a dihydrogen phosphate of alkali metal, an organic acid salt of alkali metal, or an acidic amino-acid salt of alkali metal to act" means that a carboxyl group (—COOH) contained in the graft copolymer is deprotonated into the state of a deprotonated carboxyl group (—COO⁻).

Examples of the hydroxide of alkali metal used at this step include, for example, lithium hydroxide, sodium hydroxide, potassium hydroxide, and the like, and sodium hydroxide and potassium hydroxide are preferable. Potassium hydroxide is more preferable.

An amount of the hydroxide of alkali metal used at this step is typically 0.001 to 10 equivalents relative to the graft copolymer.

Examples of the carbonate of alkali metal used at this step include, for example, lithium carbonate, sodium carbonate, potassium carbonate, and the like, and sodium carbonate and potassium carbonate are preferable. Potassium carbonate is more preferable.

An amount of the carbonate of alkali metal used at this step is typically 0.001 to 10 equivalents relative to the graft copolymer.

Examples of the hydrogencarbonate of alkali metal used at this step include, for example, lithium hydrogencarbonate, sodium hydrogencarbonate, potassium hydrogencarbonate, and the like, and sodium hydrogencarbonate and potassium hydrogencarbonate are preferable. Potassium hydrogencarbonate is more preferable.

An amount of the hydrogencarbonate of alkali metal used at this step is 0.001 to 10 equivalents relative to the graft copolymer.

Examples of the phosphate of alkali metal used at this step include, for example, lithium phosphate, sodium phosphate, potassium phosphate, and the like, and sodium phosphate and potassium phosphate are preferable. Potassium phosphate is more preferable.

An amount of the phosphate of alkali metal used at this step is typically 0.001 to 10 equivalents relative to the graft copolymer.

Examples of the monohydrogen phosphate of alkali metal used at this step include, for example, lithium monohydrogen phosphate, sodium monohydrogen phosphate, potassium monohydrogen phosphate, and the like, and sodium monohydrogen phosphate and potassium monohydrogen phosphate preferable. Potassium monohydrogen phosphate is more preferable.

An amount of the monohydrogen phosphate of alkali metal used at this step is typically 0.001 to 10 equivalents relative to the graft copolymer.

Examples of the dihydrogen phosphate of alkali metal used at this step include, for example, lithium dihydrogen phosphate, sodium dihydrogen phosphate, potassium dihydrogen phosphate, and the like, and sodium dihydrogen phosphate and potassium dihydrogen phosphate are preferable. Potassium dihydrogen phosphate is more preferable.

An amount of the dihydrogen phosphate of alkali metal used at this step is typically 0.001 to 10 equivalents relative to the graft copolymer.

Examples of "organic acid salt" used for the organic acid salt of alkali metal used at this step include salts with formic acid, acetic acid, fumaric acid, oxalic acid, tartaric acid, maleic acid, lactic acid, citric acid, succinic acid, malic acid, benzoic acid, and the like. Among them, lactic acid, acetic acid, citric acid, and benzoic acid are preferable, and lactic acid, acetic acid, and benzoic acid are more preferable.

Examples of the organic acid salt of alkali metal used at this step include, for example, lithium formate, lithium acetate, lithium fumarate, lithium oxalate, lithium tartrate, lithium maleate, lithium lactate, lithium citrate, lithium succinate, lithium malate, lithium benzoate, sodium formate, sodium acetate, sodium fumarate, sodium oxalate, sodium tartrate, sodium maleate, sodium lactate, sodium citrate, sodium succinate, sodium malate, sodium benzoate, potassium formate, potassium acetate, potassium fumarate, potassium oxalate, potassium tartrate, potassium maleate, potassium lactate, potassium citrate, potassium succinate, potassium malate, potassium benzoate, and the like. Sodium lactate, sodium acetate, sodium benzoate, potassium lactate, potassium acetate, and potassium benzoate are preferable and, among them, potassium lactate, potassium acetate, and potassium benzoate are preferable.

An amount of the organic acid salt of alkali metal used at this step is typically 0.001 to 10 equivalents relative to the graft copolymer.

Examples of "acidic amino acid" used for the acidic amino-acid salt of alkali metal used at this step include aspartic acid, glutamic acid, and the like. Among them, aspartic acid is preferable.

Examples of the acidic amino-acid salt of alkali metal used at this step include, for example, lithium aspartate, lithium glutamate, sodium aspartate, sodium glutamate, potassium aspartate, potassium glutamate, and the like. Sodium aspartate, and potassium aspartate are preferable. Potassium aspartate is more preferable.

An amount of the acidic amino-acid salt of alkali metal used at this step is typically 0.001 to 10 equivalents relative to the graft copolymer.

The step is performed in a solvent not affecting a reaction. Examples of such a solvent include, for example, water, a mixture of an organic solvent described below and water, and the like. Examples of the organic solvent include $C_{1-3}$ alcohol, dimethylsulfoxide (DMSO), tetrahydrofuran (THF), N,N-dimethylformamide (DMF), N,N-dimethylacetamide (DMAc), N-methylpyrrolidone (NMP), aprotic solvents with high polarity such as acetonitrile, acetone, pyridine, methyl acetate, and the like.

A reaction temperature of this step is typically −30 to 80° C., preferably −5 to 45° C., more preferably −5 to 30° C.

A reaction time of this step is typically from 0.1 hours to 7 days, preferably from 0.5 hours to 2 days.

A number average molecular weight of the ionized graft copolymer acquired in this way is 1 to 2,000 kDa, preferably 10 to 1,000 kDa.

Examples of the ionized graft copolymer of the present invention produced by the method include an ionized graft copolymer represented by Formula (II):

[Chem. 9]

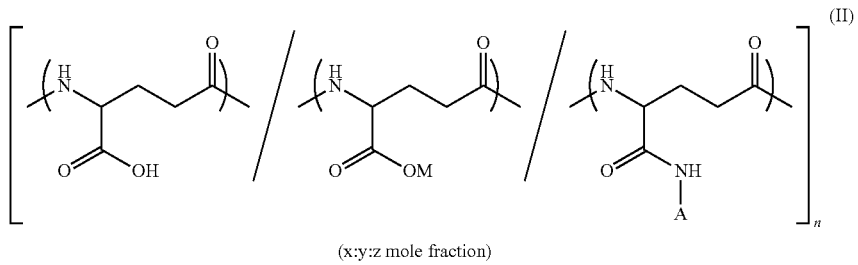

(x:y:z mole fraction)

[wherein M is alkali metal, A is a hydrophobic moiety, and n is an integer from 10 to 100,000; diagonal lines intervening three monomer units represent that the monomer units are arranged in irregular order; and x is a mole fraction of the monomer unit represented by Formula (III):

[Chem. 10]

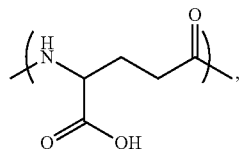

y is a mole fraction of the monomer unit represented by Formula (IV):

[Chem. 11]

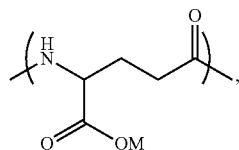

z is a mole fraction of the monomer unit represented by Formula (V):

[Chem. 12]

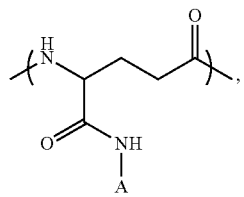

and
x, y, and z satisfy the following equations:

$0 \leq x < 1;$ $0 < y < 1;$ $0 < z < 1;$ and $x+y+z=1$]. [Math. 3]

In the monomer unit represented by Formula (IV), examples of the alkali metal denoted by M include lithium, sodium, potassium, and the like and, among them, the alkali metal is preferably sodium or potassium, most preferably potassium.

In the monomer unit represented by Formula (V), examples of the hydrophobic moiety denoted by A are the same as those of the "hydrophobic moiety" denoted by A in the hydrophobic primary amine compound represented by Formula (I): A-NH$_2$ [wherein A denotes a hydrophobic moiety]. In the monomer unit represented by Formula (V), specific examples of —NH-A [wherein A denotes a hydrophobic moiety] include an α-amino acid derivative that may have a substituent. The "α-amino acid derivative" is preferably a phenylalanine derivative and is preferably a phenylalanine alkyl ester derivative, particularly preferably a phenylalanine ethyl ester derivative. The "amino acid derivative" may be the L-isomer, the D-isomer, or the mixture thereof.

In Formula (II), the monomer unit represented by Formula (III) preferably has a mole fraction x of 0.01 to 0.99, more preferably 0.15 to 0.95.

In Formula (II), the monomer unit represented by Formula (IV) preferably has a mole fraction y of 0.02 to 0.6, more preferably 0.05 to 0.5.

In Formula (II), the monomer unit represented Formula (V) preferably has a mole fraction z of 0.01 to 0.99, more preferably 0.05 to 0.85.

In Formula (II), x, y, and z may have arbitrary numerical values within the respective preferable ranges, provided that x+y+z does not exceed 1.

The ionized copolymer is preferably balanced between moderate water solubility and moderate hydrophobicity depending on the total number of monomer units in the graft copolymer and the structure of the hydrophobic moiety A for being used in production of nanoparticles that are a third aspect of the present invention.

In this description, n denotes the total number of monomer units in the graft copolymer.

In a preferred embodiment, n is 50 to 10,000, more preferably 100 to 2,000.

In this description, a "hydrophobic parameter K" corresponds to an octanol/water distribution coefficient when 1-octanol and water are used as a solvent, and is indicated by Log Pow in this description.

A method of actually measuring Log Pow may be JIS-Z7260-107, for example. However, since the ionized graft copolymer of poly(amino acid) of the present invention makes measurement difficult because of low solubility at the time of concentration measurement, a method may be employed in which each of organic and water layers after distribution is hydrolyzed to quantitate the respective concentrations of amino acid monomers.

The "hydrophobic parameter K" may be determined by using a calculation value from a CLOGP method, which is a method of calculation from chemical structure, instead of an actual measurement value of Log Pow. The "hydrophobic parameter K" calculated with the CLOGP method is indicated by CLOGP in this description.

In a preferred embodiment, the hydrophobic parameter K is −15,000 to 0, more preferably −3,000 to 0.

A third aspect of the present invention relates to nanoparticles containing an ionized graft copolymer of a poly(amino acid) selected from the group consisting of poly(γ-glutamic acid), poly(α-glutamic acid), and poly(aspartic acid) or a salt thereof and a hydrophobic primary amine compound represented by Formula (I): A-NH$_2$ [wherein A denotes a hydrophobic moiety] or a salt thereof, and a production method thereof.

The production method of the nanoparticles according to the third aspect of the present invention comprises the steps of:

(1) condensing a poly(amino acid) selected from the group consisting of poly(γ-glutamic acid), poly(α-glutamic acid), and poly(aspartic acid) or a salt thereof and a hydrophobic primary amine compound represented by Formula (I): A-NH$_2$ [wherein A denotes a hydrophobic moiety] or a salt thereof;

(2) isolating a graft copolymer by allowing an acid to act on a condensate acquired at step (1);

(3) ionizing the graft copolymer by allowing a hydroxide of alkali metal, a carbonate of alkali metal, or a hydrogencarbonate of alkali metal to act on the graft copolymer isolated at step (2); and (4) forming nanoparticles of the ionized graft copolymer acquired at step (3).

Steps (1) and (2) may be performed in accordance with the production method of a graft copolymer of a poly(amino acid) or a salt thereof and a hydrophobic primary amine compound represented by Formula (I) or a salt thereof described above.

Step (3) may be performed in accordance with the production method of an ionized graft copolymer of a poly(amino acid) or a salt thereof and a hydrophobic primary amine compound represented by Formula (I) or a salt thereof described above.

The method of forming nanoparticles of the ionized graft copolymer of step (4) may be performed in conformity to the method described in Patent Document 3. For example, if a precipitation method is used, the ionized graft copolymer acquired at step (3) may be dissolved in a good solvent and subsequently be mixed with a poor solvent to form nanoparticles.

The "good solvent" may be, for example, dimethyl sulfoxide or alcohols (such as methanol, ethanol, isopropanol, and n-propanol).

The "poor solvent" may be water. If water is used as the poor solvent, water is normally used as an aqueous solution of sodium chloride, sodium phosphate, sodium monohydrogen phosphate, sodium dihydrogen phosphate, sodium carbonate, sodium hydrogencarbonate, potassium chloride, potassium phosphate, potassium monohydrogen phosphate, potassium dihydrogen phosphate, potassium carbonate, potassium hydrogencarbonate, and the like. The solution of the ionized graft copolymer acquired at step (3) and the poor solvent may be mixed in both batch-wise and continuous manners.

At the step of ionizing the graft copolymer of a poly(amino acid) or a salt thereof and a hydrophobic primary amine compound represented by Formula (I) or a salt thereof, the ionization may be controlled to adjust an ionization rate of COOH side chains of the poly(amino acid) not binding to the hydrophobic primary amine compound represented by Formula (I) or a salt thereof. By adjusting the ionization rate as described above, nanoparticles with different properties may be produced. Using the production method of the present invention facilitates scale-up and enables the large-scale synthesis of the nanoparticles. If the nanoparticles are prepared from the free form of the graft copolymer, an amount of ionization at the time of formation of the nanoparticles may be controlled. The type of ionization of the graft copolymer is not limited to sodium and the ionization may selectively be achieved by various ion species.

In this description, the "free form of the graft copolymer" refers to the case of y=0 in Formula (VI), i.e., the state in which all the carboxyl groups in the graft copolymer are present as COOH.

In this description, the "ionized graft copolymer" refers to the case of y is other than 0 in Formula (VI), i.e., the state in which all or some of the carboxyl groups in the graft copolymer are present as salt.

In this description, the "monomer unit" means a constituent unit of polymer such as a graft copolymer.

The "nanoparticle" means taking a form of particulates that are mainly composed of aggregates made of a graft copolymer of a poly(amino acid) or a salt thereof and a hydrophobic primary amine compound or a salt thereof and that have a size of 5000 nanometers (nm) or less in the major axis while forming a clear interface with the surrounding environment.

The nanoparticles of the present invention may have various shapes such as a spherical shape, a hollow shape, and a porous spherical shape.

A particle diameter of the nanoparticles of the present invention is 1 nanometer (nm) to 1500 nm, preferably 1 nm to 500 nm, more preferably 10 nm to 300 nm, under a physiological condition.

The "nanoparticles" of the present invention may contain a substance other that the graft copolymer of a poly(amino acid) or a salt thereof and a hydrophobic primary amine compound or a salt thereof.

For example, the nanoparticles of the present invention may be used as an adjuvant for vaccine, when one or two or more antigens are contained in the nanoparticles or immobilized on the surfaces of the nanoparticles.

In this description, the "antigens" means those capable of inducing an immune reaction and may be, but not limited to, pathogens including viruses such as human immunodeficiency virus (HIV) and human papillomavirus (HPV) and pathogenic organisms such as *tubercule bacillus* and *tetanus bacillus* or a portion thereof, or proteins, peptides, and nucleic acids, for example. Such antigens may be selected as needed depending on a disease to be treated or prevented.

In this description, the "adjuvant" means a substance stimulating an immune system and enhancing an immune reaction.

Therefore, a forth aspect of the present invention relates to a vaccine containing such nanoparticles.

The vaccine of the present invention may contain the nanoparticles containing the graft copolymer of a poly(amino acid) and a hydrophobic primary amine compound represented by Formula (I) as an adjuvant and the antigens, and may further contain a solvent, a solubilizing agent, a suspending agent, an isotonizing agent, a soothing agent, an antiseptic agent, an anti-oxidizing agent, and the like.

Examples of the solvent include, for example, water for injection, alcohol, propylene glycol, macrogol, sesame oil, corn oil, olive oil, and the like.

Examples of the solubilizing agent include, for example, polyethylene glycol, propylene glycol, D-mannitol, benzyl benzoate, ethanol, tris-aminomethane, cholesterol, triethanolamine, sodium carbonate, sodium citrate, and the like.

Examples of the suspending agent include, for example, surfactants such as stearyl triethanolamine, sodium lauryl sulfate, lauryl amino propioate, lecithin, benzalkonium chloride, benzethonium chloride, and glyceryl monostearate; hydrophilic macromolecules such as polyvinyl alcohol, polyvinylpyrrolidone, carboxymethyl-cellulose sodium, methyl cellulose, hydroxymethyl cellulose, hydroxyethyl cellulose, and hydroxypropyl cellulose; magnesium chloride, and the like.

Examples of the isotonizing agent include, for example, glucose, D-sorbitol, sodium chloride, glycerin, D-mannitol, and the like.

Examples of the soothing agent include, for example, benzyl alcohol, and the like.

Examples of the antiseptic agent include, for example, p-hydroxybenzoic acid esters, chlorobutanol, benzyl alcohol, phenethyl alcohol, dehydroacetic acid, sorbic acid, and the like.

Examples of the anti-oxidizing agent include, for example, sulfite, ascorbic acid, α-tocopherol, and the like.

The vaccine of the present invention may be in any forms such as solution, suspension, lyophilizate, powder, capsules, and tablets. If the vaccine of the present invention is solid, the vaccine may be suspended or dissolved in a proper solvent such as saline before use.

The vaccine of the present invention is biodegradable. The biodegradability means that a substance has structure degradable in vivo and that the substance itself and a degradation or metabolic product thereof are safe or are nontoxic or low-toxic.

With the vaccine of the present invention, mammals (e.g., mice, rats, rabbits, felines, canines, bovines, equines, monkeys, and humans) may safely be inoculated.

An inoculum dose, an inoculation method, the number of times of inoculation of the vaccine of the present invention may appropriately be selected depending on, for example, an age and a condition of a subject, a type of disease, a type of antigen, and the like.

The inoculum dose of the vaccine of the present invention is, for example, an antigen amount of 1 mg to 100 mg per dose per adult (with body weight of about 60 kg).

Examples of the inoculation method of the vaccine of the present invention include, for example, oral inoculation, subcutaneous injection, intramuscular injection, infusion, and the like.

The number of times of inoculation of the vaccine of the present invention is from once to multiple times.

EXAMPLES

Although the present invention will hereinafter specifically be described with examples, the present invention is not limited thereto. A graft copolymer of poly(γ-glutamic acid) and phenylalanine ethyl ester is a polymer of the present invention and will hereinafter be referred to as γ-PGA-PAE. Water described in the following description may be replaced with water for injection, ion-exchanged water, and the like. Unless otherwise stated, a molecular weight is a relative molecular weight and is a numerical value determined by a molecular weight measurement method using the following SEC-HPLC measurement: TSKgel α-M 300×7.8 mm I.D. (dual), 5 mM NaNO$_3$ DMSO:H$_2$O (9:1), 0.8 mL/minute, 40° C., RI detector, standard: Pullulan (Shodex).

[Example 1] Synthesis of γ-PGA-PAE

In a 1-L four-necked flask, distilled water (400 mL) and NaHCO$_3$ (8.4 g) were measured and dissolved at room temperature. To this solution, γ-PGA (12.1 g, 148 kDa) was added, washed and dissolved with distilled water (60 mL), and then ice-cooled. At ice temperature, WSC.HCl (19.2 g) was added and washed with distilled water (10 mL). After this solution was stirred for 5 minutes, L-phenylalanine ethyl ester hydrochloride (PAE.HCl) (13.8 g) was added and washed with distilled water (15 mL). The solution was stirred for 1 hour at ice temperature and then stirred for 24 hours at room temperature. At room temperature, 2 M hydrochloric acid (120 mL) was added dropwise and stirred for 2 hours. A precipitate was sucked and filtered and was washed with distilled water (100 mL) twice. The precipitate was dried under reduced pressure at room temperature to acquire γ-PGA-PAE (23.2 g, yield: about 96.8%, PAE introduction rate: 55%, moisture: 5.8%, 85 kDa).

$^1$H NMR (500 MHz, DMSO-d$_6$) δ 0.6-1.2 (brs, 3.6H), 1.4-2.4 (brm, 6.7H), 2.6-2.8 (brm, 1.2H), 2.8-3.1 (brm, 3.0H), 3.8-4.5 (brm, 4.1H), 4.5-5.5 (brm, 0.4H), 6.4-6.6 (brm, 0.1H), 6.7-7.5 (brm, 5.0H, a relative value when the protons of the phenyl group of the phenylalanyl group are assumed as 5.0H), 7.6-8.7 (brm, 2.3H).

[Example 2] Synthesis of γ-PGA-PAE

In a 1-L four-necked flask, distilled water (400 mL) and NaHCO$_3$ (8.4 g) were measured and dissolved at room temperature. To this solution, γ-PGA (12.1 g, 148 kDa) was added, washed and dissolved with distilled water (66 mL), and then ice-cooled. At ice temperature, WSC.HCl (19.2 g) was added and washed with distilled water (15 mL). After this solution was stirred for 5 minutes, PAE.HCl (13.8 g) was added and washed with distilled water (5 mL). The solution was stirred for 1 hour at ice temperature and then stirred for 5 hours at room temperature. At room temperature, 2 M hydrochloric acid (120 mL) was added dropwise and stirred for 2 hours. A precipitate was sucked and filtered and was washed with distilled water (100 mL) twice. The precipitate was dried under reduced pressure at room temperature to acquire γ-PGA-PAE (21.1 g, yield: about 94.5%, PAE introduction rate: 46%, moisture: 4.5%, 133 kDa).

$^1$H NMR (500 MHz, DMSO-d$_6$) δ 0.9-1.3 (brs, 3.0H), 1.4-2.4 (brm, 6.2H), 2.6-2.8 (brm, 0.8H), 2.8-3.1 (brm, 2.6H), 3.9-4.5 (brm, 4.0H), 4.5-5.5 (brm, 0.4H), 6.4-6.6 (brm, 0.1H), 6.9-7.5 (brm, 5.0H, a relative value when the protons of the phenyl group of the phenylalanyl group are assumed as 5.0H), 7.6-8.7 (brm, 2.2H).

[Example 3] Synthesis of γ-PGA-PAE

In a 1-L four-necked flask, 1 M sodium hydroxide aqueous solution (90 mL) was measured in distilled water (385 mL) at room temperature, and γ-PGA (12.1 g, 148 kDa) was dissolved and ice-cooled. At ice temperature, WSC.HCl (19.2 g) was added and washed with distilled water (4 mL). After this solution was stirred for 5 minutes, PAE.HCl (13.8 g) was added and washed with distilled water (6 mL). The solution was stirred for 1 hour at ice temperature and then stirred for 5 hours at room temperature. At room temperature, 2 M hydrochloric acid (120 mL) was added dropwise and stirred for 2 hours. A precipitate was sucked and filtered and was washed with distilled water (100 mL) twice. The precipitate was dried under reduced pressure at room temperature to acquire γ-PGA-PAE (21.7 g, yield: about 94.8%, PAE introduction rate: 59%, moisture: 4.5%, 286 kDa).

$^1$H NMR (500 MHz, DMSO-$d_6$) δ 1.1-1.2 (brs, 3.2H), 1.4-2.4 (brm, 6.9H), 2.6-2.8 (brm, 0.6H), 2.8-3.1 (brm, 2.4H), 3.1-3.8 (brm, 7.2H), 4.0 (brs, 2.0H), 4.1-4.4 (brm, 2.5H), 4.6-5.2 (brm, 0.2H), 6.9-7.5 (brm, 5.0H, a relative value when the protons of the phenyl group of the phenylalanyl group are assumed as 5.0H), 7.7-9.0 (brm, 2.6H), 10.0-15.0 (brs, 0.2H).

[Example 4] Synthesis of γ-PGA-PAE

In a 1-L four-necked flask, 1 M sodium hydroxide aqueous solution (90 mL) was measured in distilled water (385 mL) at room temperature, and γ-PGA (12.1 g, 148 kDa) was dissolved and ice-cooled. At ice temperature, WSC.HCl (19.2 g) was added and washed with distilled water (4 mL). After this solution was stirred for 5 minutes, PAE.HCl (13.8 g) was added and washed with distilled water (6 mL). The solution was stirred for 1 hour at ice temperature and then stirred for 22 hours at room temperature. At room temperature, 2 M hydrochloric acid (120 mL) was added dropwise and stirred for 2 hours. A precipitate was sucked and filtered and was washed with distilled water (100 mL) twice. The precipitate was dried under reduced pressure at room temperature to acquire γ-PGA-PAE (26.8 g, yield: about 93.6%, PAE introduction rate: 59%, moisture: 23.6%, 44 kDa).

$^1$H NMR (500 MHz, DMSO-$d_6$) δ 0.7-1.2 (brs, 3.2H), 1.4-2.4 (brm, 6.81-1), 2.6-2.8 (brm, 1.1H), 2.8-3.1 (brm, 2.9H), 3.8-5.1 (brm, 4.4H), 6.9-7.5 (brm, 5.01-1, a relative value when the protons of the phenyl group of the phenylalanyl group are assumed as 5.0H), 7.6-8.7 (brm, 2.4H).

[Example 5] Synthesis of γ-PGA-PAE

In a 1-L four-necked flask, distilled water (350 mL) and 1 M NaOH (90 mL) were measured and mixed at room temperature. To this solution, γ-PGA [12.1 g, 65 kDa, D:L ratio (35:65)] was added and washed with distilled water (28 mL). After dissolution, the solution was ice-cooled. At ice temperature, WSC.HCl (19.2 g) was added and washed with distilled water (10 mL). After this solution was stirred for 5 minutes, PAE.HCl (13.8 g) was added and washed with distilled water (10 mL). The solution was stirred for 1 hour at ice temperature and then stirred for 5 hours at room temperature. At room temperature, 2 M hydrochloric acid (120 mL) was added dropwise and stirred for 1 hour. A precipitate was sucked and filtered and was washed with distilled water (100 mL) twice. The precipitate was dried under reduced pressure at room temperature to acquire γ-PGA-PAE [20.5 g, yield: about 86.2%, PAE introduction rate: 72%, moisture: 2.2%, 247 kDa, Glu D:L ratio (36:64)].

$^1$H NMR (500 MHz, DMSO-$d_6$) δ 0.9-1.3 (brs, 3.2H), 1.4-2.4 (brm, 6.8H), 2.6-2.8 (brm, 0.9H), 2.8-3.1 (brm, 2.5H), 3.9-4.5 (brm, 4.7H), 4.5-5.5 (brm, 0.2H), 6.9-7.5 (brm, 5.0H, a relative value when the protons of the phenyl group of the phenylalanyl group are assumed as 5.0H), 7.6-9.1 (brm, 2.6H).

[Example 6] Synthesis of γ-PGA-PAE

In a 100-mL Scott bottle, distilled water (39 mL) and 1 M NaOH (9.0 mL) were mixed at room temperature. Into this solution, γ-PGA (1.2 g, 65 kDa) was dissolved and then ice-cooled. At ice temperature, WSC.HCl (1.8 g) was added. After this solution was stirred for 5 minutes, PAE.HCl (1.3 g) was added. This solution was reacted overnight from ice temperature to room temperature and stirred for 20 hours. At room temperature, 2 M hydrochloric acid (11 mL) was added dropwise and stirred for 3 hours. A precipitate was sucked and filtered and was washed with distilled water (20 mL) twice. The precipitate was dried under reduced pressure at room temperature to acquire γ-PGA-PAE (2.0 g, yield: about 98.8%, PAE introduction rate: 52%, moisture: 2.9%, 89 kDa).

$^1$H NMR (500 MHz, DMSO-$d_6$) δ 0.9-1.3 (brs, 3.3H), 1.4-2.4 (brm, 7.9H), 2.6-2.8 (brm, 0.9H), 2.8-3.1 (brm, 2.6H), 3.9-4.5 (brm, 4.8H), 4.5-5.5 (brm, 0.2H), 6.9-7.5 (brm, 5.0H, a relative value when the protons of the phenyl group of the phenylalanyl group are assumed as 5.0H), 7.6-8.7 (brm, 2.8H).

[Example 7] Synthesis of γ-PGA-PAE

In a 1-L four-necked flask, distilled water (440 mL) and γ-PGA sodium salt [15.0 g, 29 kDa, D:L ratio (83:17)] were measured and dissolved at room temperature and then ice-cooled. At ice temperature, WSC.HCl (19.2 g) was added and stirred for 5 minutes. PAE.HCl (13.8 g) was then added. The solution was stirred for 1 hour at ice temperature and then stirred for 5 hours at room temperature. At room temperature, 2 M hydrochloric acid (120 mL) was added dropwise and stirred for 1 hour. A precipitate was sucked and filtered and was washed with distilled water (100 mL) twice. The precipitate was dried under reduced pressure at room temperature to acquire γ-PGA-PAE [18.2 g, yield: about 91.2%, PAE introduction rate: 59%, moisture: 3.5%, 56 kDa, Glu D:L ratio (50:50)].

$^1$H NMR (500 MHz, DMSO-$d_6$) δ 0.9-1.3 (brs, 3.0H), 1.4-2.4 (brm, 5.7H), 2.6-2.8 (brm, 0.5H), 2.8-3.1 (brm, 2.3H), 3.9-4.5 (brm, 4.2H), 4.5-5.5 (brm, 0.2H), 6.9-7.5 (brm, 5.0H, a relative value when the protons of the phenyl group of the phenylalanyl group are assumed as 5.0H), 7.6-8.7 (brm, 2.2H).

[Example 8] Synthesis of γ-PGA-PAE

In a 1-L four-necked flask, distilled water (440 mL) and γ-PGA sodium salt (15.0 g, 29 kDa) were measured and dissolved at room temperature and then ice-cooled. At ice temperature, WSC.HCl (19.2 g) was added and stirred for 5 minutes. PAE.HCl (13.8 g) was then added. The solution was stirred for 1.5 hours at ice temperature and then stirred for 20.5 hours at room temperature. At room temperature, 2 M hydrochloric acid (120 mL) was added dropwise and stirred for 1 hour. A precipitate was sucked and filtered and was washed with distilled water (100 mL) twice. The precipitate was dried under reduced pressure at room temperature to acquire γ-PGA-PAE (19.3 g, yield: about 90.9%, PAE introduction rate: 70%, moisture: 2.1%, 54 kDa).

$^1$H NMR (500 MHz, DMSO-$d_6$) δ 0.9-1.3 (brs, 3.4H), 1.4-2.4 (brm, 5.4H), 2.6-2.8 (brm, 0.7H), 2.8-3.1 (brm, 2.3H), 3.9-4.5 (brm, 4.0H), 4.5-5.5 (brm, 0.1H), 6.9-7.5 (brm, 5.0H, a relative value when the protons of the phenyl group of the phenylalanyl group are assumed as 5.0H), 7.6-8.7 (brm, 2.2H).

[Example 9] Synthesis of γ-PGA-PAE

In a 20-mL sample bottle, NaHCO$_3$ (42 mg) was measured and dissolved in distilled water (2.5 mL) at room temperature. After γ-PGA (61 mg, 148 kDa) was added and dissolved, the solution was ice-cooled. At ice temperature, DMTMM (453 mg) was added and stirred for 7 minutes. PAE.HCl (108 mg) was then added. The solution was stirred for 1.0 hour at ice temperature and then stirred for about 15 hours at room temperature. At room temperature, 2 M hydrochloric acid (0.47 mL) was added dropwise and stirred for 1 hour. A precipitate was sucked and filtered and was washed with distilled water. The precipitate was dried under reduced pressure at room temperature to acquire γ-PGA-PAE (103 mg, PAE introduction rate: 68%).

$^1$H NMR (500 MHz, DMSO-$d_6$) δ 0.9-1.3 (brs, 2.9H), 1.4-2.4 (brm, 5.9H), 2.8-3.1 (brm, 2.0H), 3.9-4.5 (brm, 4.3H), 6.9-7.5 (brm, 5.0H, a relative value when the protons of the phenyl group of the phenylalanyl group are assumed as 5.0H), 7.6-8.7 (brm, 2.2H).

[Example 10] Synthesis of γ-PGA-D-PAE

In a 100-mL Scott bottle, distilled water (39 mL) and γ-PGA sodium salt [1.62 g, 29 kDa, D:L ratio (83:17)] were measured, dissolved, and then ice-cooled. At ice temperature, WSC.HCl (1.80 g) was added and stirred for 5 minutes. D-phenylalanine ethyl ester hydrochloride (D-PAE.HCl) (1.30 g) was added and vigorously stirred for 1.3 hours at ice temperature. The solution was then stirred for 5 hours at room temperature. At room temperature, 2 M hydrochloric acid (14 mL) was added dropwise and stirred for 1.5 hours. A precipitate was sucked and filtered and was washed with distilled water (10 mL) twice. The precipitate was dried under reduced pressure at room temperature to acquire γ-PGA-D-PAE [1.90 g, PAE introduction rate: 67%, moisture: 2.41%, 64 kDa, Glu D:L ratio (66:34)].

$^1$H NMR (500 MHz, DMSO-$d_6$) δ 0.9-1.3 (brs, 3.2H), 1.4-2.4 (brm, 6.0H), 2.6-2.8 (brm, 0.6H), 2.8-3.1 (brm, 2.4H), 3.9-4.5 (brm, 4.4H), 4.5-5.5 (brm, 0.2H), 6.9-7.5 (brm, 5.0H, a relative value when the protons of the phenyl group of the phenylalanyl group are assumed as 5.0H), 7.6-8.7 (brm, 2.3H).

[Example 11] Synthesis of γ-PGA-D-PAE

In a 100-mL Scott bottle, 1 M sodium hydroxide aqueous solution (9.0 mL) and distilled water (35 mL) were measured and sufficiently stirred. After γ-PGA [1.21 g, 65 kDa, D:L ratio (35:65)] was added at room temperature and dissolved, the solution was ice-cooled. At ice temperature, WSC.HCl (1.80 g) was added and stirred for 5 minutes. D-PAE.HCl (1.30 g) was added and vigorously stirred for 1.5 hours at ice temperature. The solution was then stirred for 21 hours at room temperature. At room temperature, 2 M hydrochloric acid (13 mL) was added dropwise and stirred for 2.5 hours. A precipitate was sucked and filtered and was washed with distilled water (10 mL) twice. The precipitate was dried under reduced pressure at room temperature to acquire γ-PGA-D-PAE [1.96 g, PAE introduction rate: 56%, moisture: 2.35%, 98 kDa, Glu D:L ratio (54:46)].

$^1$H NMR (500 MHz, DMSO-$d_6$) δ 0.9-1.3 (brs, 3.3H), 1.4-2.4 (brm, 7.2H), 2.6-2.8 (brm, 0.5H), 2.8-3.1 (brm, 2.4H), 3.9-4.5 (brm, 4.9H), 4.5-5.5 (brm, 0.3H), 6.9-7.5 (brm, 5.0H, a relative value when the protons of the phenyl group of the phenylalanyl group are assumed as 5.0H), 7.6-8.7 (brm, 2.6H).

[Example 12] Synthesis of γ-PGA-DL-PAE

In a 100-mL Scott bottle, 1 M sodium hydroxide aqueous solution (9.0 mL) and distilled water (35 mL) were measured and sufficiently stirred. After γ-PGA [1.21 g, 65 kDa, D:L ratio (35:65)] was added at room temperature and dissolved, the solution was ice-cooled. At ice temperature, WSC.HCl (1.80 g) was added and stirred for 5 minutes. DL-PAE.HCl (1.30 g) was added and vigorously stirred for 1.5 hours at ice temperature. The solution was then stirred for 21 hours at room temperature. At room temperature, 2 M hydrochloric acid (13 mL) was added dropwise and stirred for 2.5 hours. A precipitate was sucked and filtered and was washed with distilled water (10 mL) twice. The precipitate was dried under reduced pressure at room temperature to acquire γ-PGA-DL-PAE [2.06 g, PAE introduction rate: 56%, moisture: 2.51%, 97 kDa, Glu D:L ratio (45:55)].

$^1$H NMR (500 MHz, DMSO-$d_6$) δ 0.9-1.3 (brs, 3.3H), 1.4-2.4 (brm, 7.2H), 2.6-2.8 (brm, 0.5H), 2.8-3.1 (brm, 2.5H), 3.9-4.5 (brm, 4.7H), 4.5-5.5 (brm, 0.3H), 6.9-7.5 (brm, 5.0H, a relative value when the protons of the phenyl group of the phenylalanyl group are assumed as 5.0H), 7.6-8.7 (brm, 2.6H).

[Example 13] Synthesis of γ-PGA-PAE

In a 100-mL Scott bottle, NaHCO$_3$ (0.42 g) and distilled water (49 mL) were measured and sufficiently stirred. After γ-PGA (0.61 g, 114 kDa) was added at room temperature and stirred for 30 minutes and dissolved at room temperature, the solution was ice-cooled and stirred for 15 minutes. At ice temperature, WSC.HCl (0.90 g) was added and stirred for 5 minutes. PAE.HCl (1.08 g) was added and vigorously stirred for 1.0 hour at ice temperature. The solution was then stirred for 20 hours at room temperature. At room temperature, 2 M hydrochloric acid (10 mL) was added dropwise and stirred for 1 hour. A precipitate was sucked and filtered and was washed with distilled water (5 mL) twice. The precipitate was dried under reduced pressure at 40° C. to acquire γ-PGA-PAE (1.09 g, PAE introduction rate: 67%, moisture: 2.7%).

$^1$H NMR (500 MHz, DMSO-$d_6$) δ 0.9-1.3 (brs, 3.1H), 1.4-2.4 (brm, 5.3H), 2.6-2.8 (brm, 0.7H), 2.8-3.1 (brm, 2.4H), 3.9-5.5 (brm, 4.4H), 6.9-7.5 (brm, 5.0H, a relative value when the protons of the phenyl group of the phenylalanyl group are assumed as 5.0H), 7.6-8.7 (brm, 2.1H).

[Example 14] Synthesis of γ-PGA-PAE

In a 50-mL conical flask, NaHCO$_3$ (0.42 g) and distilled water (36 mL) were measured and sufficiently stirred. After γ-PGA (0.61 g, 114 kDa) was added at room temperature and stirred for 30 minutes and dissolved at room temperature, the solution was ice-cooled and stirred for 15 minutes. At ice temperature, WSC.HCl (0.90 g) was added and stirred for 5 minutes. PAE.HCl (1.08 g) was added and vigorously stirred for 1.0 hour at ice temperature. The solution was then stirred for 20 hours at room temperature. At room temperature, 2 M hydrochloric acid (10 mL) was added dropwise and stirred for 1 hour. A precipitate was sucked and filtered and was washed with distilled water (5 mL) twice. The precipitate was dried under reduced pressure at 40° C. to acquire γ-PGA-PAE (1.14 g, PAE introduction rate: 67%, moisture: 2.9%).

$^1$H NMR (500 MHz, DMSO-$d_6$) δ 0.9-1.3 (brs, 3.2H), 1.4-2.4 (brm, 5.2H), 2.6-3.1 (brm, 3.0H), 3.9-5.5 (brm, 4.0H), 6.9-7.5 (brm, 5.0H, a relative value when the protons of the phenyl group of the phenylalanyl group are assumed as 5.0H), 7.6-8.7 (brm, 2.1H).

[Example 15] Synthesis of γ-PGA-PAE

In a 50-mL conical flask, NaHCO$_3$ (0.42 g) and distilled water (30 mL) were measured and sufficiently stirred. After γ-PGA (0.61 g, 114 kDa) was added at room temperature and stirred for 30 minutes and dissolved at room temperature, the solution was ice-cooled and stirred for 15 minutes. At ice temperature, WSC.HCl (0.90 g) was added and stirred for 5 minutes. PAE.HCl (1.08 g) was added and vigorously stirred for 1.0 hour at ice temperature. The solution was then stirred for 20 hours at room temperature. At room temperature, 2 M hydrochloric acid (10 mL) was added dropwise and stirred for 1 hour. A precipitate was sucked and filtered and was washed with distilled water (5 mL) twice. The precipitate was dried under reduced pressure at 40° C. to acquire γ-PGA-PAE (1.18 g, PAE introduction rate: 70%, moisture: 2.3%).
$^1$H NMR (500 MHz, DMSO-$d_6$) δ 0.9-1.3 (brs, 3.2H), 1.4-2.4 (brm, 5.1H), 2.6-3.1 (brm, 2.9H), 3.9-5.5 (brm, 4.0H), 6.9-7.5 (brm, 5.0H, a relative value when the protons of the phenyl group of the phenylalanyl group are assumed as 5.0H), 7.6-8.7 (brm, 2.1H).

[Example 16] Synthesis of γ-PGA-PAE

In a 30-mL conical flask, NaHCO$_3$ (0.42 g) and distilled water (21 mL) were measured and sufficiently stirred. After γ-PGA (0.61 g, 114 kDa) was added at room temperature and stirred for 30 minutes and dissolved at room temperature, the solution was ice-cooled and stirred for 5 minutes. At ice temperature, WSC.HCl (0.90 g) was added and stirred for 5 minutes. PAE.HCl (1.08 g) was added and vigorously stirred for 1.0 hour at ice temperature. The solution was then stirred for 20 hours at room temperature. At room temperature, 2 M hydrochloric acid (10 mL) was added dropwise and stirred for 1 hour. A precipitate was sucked and filtered and was washed with distilled water (5 mL) twice. The precipitate was dried under reduced pressure at 40° C. to acquire γ-PGA-PAE (1.21 g, PAE introduction rate: 73%, moisture: 2.6%).
$^1$H NMR (500 MHz, DMSO-$d_6$) δ 0.9-1.3 (brs, 3.2H), 1.4-2.4 (brm, 5.0H), 2.6-2.8 (brm, 0.3H), 2.8-3.1 (brm, 2.3H), 3.9-5.5 (brm, 4.2H), 6.4-6.6 (brm, 0.1H), 6.9-7.5 (brm, 5.0H, a relative value when the protons of the phenyl group of the phenylalanyl group are assumed as 5.0H), 7.6-8.7 (brm, 2.0H).

[Example 17] Synthesis of γ-PGA-PAE

In a 20-mL sample bottle, distilled water (7.8 mL) and 1 M NaOH (0.9 mL) were mixed at room temperature. Into this solution, γ-PGA (121 mg, 239 kDa) was dissolved and then ice-cooled. At ice temperature, WSC.HCl (180 mg) was added. After stirring for 5 minutes, PAE.HCl (130 mg) was added. A reaction was performed at ice temperature for 1 hour and at room temperature for 6 hours. At room temperature, 2 M hydrochloric acid (1.4 mL) was added dropwise and stirred for 1.5 hours. A precipitate was sucked and filtered and was washed with distilled water (5 mL) twice. The precipitate was dried under reduced pressure at room temperature to acquire γ-PGA-PAE (185 mg, PAE introduction rate: 50%, moisture: 3.1%, 797 kDa).
$^1$H NMR (500 MHz, DMSO-$d_6$) δ 0.9-1.3 (brs, 3.3H), 1.4-2.4 (brm, 8.0H), 2.6-2.8 (brm, 1.0H), 2.8-3.1 (brm, 2.5H), 3.9-4.5 (brm, 5.0H), 4.5-5.5 (brm, 0.3H), 6.9-7.5 (brm, 5.0H, a relative value when the protons of the phenyl group of the phenylalanyl group are assumed as 5.0H), 7.6-8.7 (brm, 2.8H).

[Example 18] Synthesis of α-L-PGA-D-PAE

In a 20-mL sample bottle, α-L-PGA sodium salt (136 mg) and distilled water (4.8 mL) were measured and dissolved. The solution was then ice-cooled. At ice temperature, WSC.HCl (180 mg) was added and stirred for 5 minutes. D-PAE.HCl (129 mg) was added and vigorously stirred for 1.5 hours at ice temperature. The solution was then stirred for 16 hours at room temperature. At room temperature, 2 M hydrochloric acid (0.14 mL) was added dropwise and stirred for 1.5 hours. A precipitate was sucked and filtered and was washed with distilled water (5 mL) twice. The precipitate was dried under reduced pressure at room temperature to acquire α-L-PGA-D-PAE (206 mg, PAE introduction rate: 70%, moisture: 2.20%).
$^1$H NMR (500 MHz, DMSO-$d_6$) δ 1.03-1.05 (brm, 3.53H), 1.50-2.35 (brm, 5.70H), 2.50-2.60 (brm, 1.24H), 2.60-2.85 (brm, 2.14H), 2.85-3.05 (brm, 2.14H), 3.10-3.25 (brm, 0.63H), 3.50-3.80 (brm, 0.83H), 3.90-5.00 (brm, 4.68H), 7.04-7.35 (brm, 5H, a relative value when the protons of the phenyl group of the phenylalanyl group are assumed as 5.0H), 7.70-9.30 (brm, 2.48H).

[Example 19] Synthesis of α-L-PGA-L-PAE

In a 20-mL sample bottle, α-L-PGA sodium salt (136 mg) and distilled water (4.8 mL) were measured and dissolved. The solution was then ice-cooled. At ice temperature, WSC.HCl (180 mg) was added and stirred for 5 minutes. L-PAE.HCl (129 mg) was added and vigorously stirred for 1.5 hours at ice temperature. The solution was then stirred for 16 hours at room temperature. At room temperature, 2 M hydrochloric acid (0.14 mL) was added dropwise and stirred for 1.5 hours. A precipitate was sucked and filtered and was washed with distilled water (5 mL) twice. The precipitate was dried under reduced pressure at room temperature to acquire α-L-PGA-L-PAE (216 mg, PAE introduction rate: 69%, moisture: 2.44%).
$^1$H NMR (500 MHz, DMSO-$d_6$) δ 1.05-1.06 (brm, 3.52H), 1.50-2.40 (brm, 5.71H), 2.50-2.75 (brm, 1.59H), 2.75-3.05 (brm, 2.41H), 3.10-3.25 (brm, 0.75H), 3.50-3.80 (brm, 0.59H), 3.90-4.50 (brm, 4.56H), 4.50-5.58 (brm, 0.02H), 7.04-7.35 (brm, 5H, a relative value when the protons of the phenyl group of the phenylalanyl group are assumed as 5.0H), 7.70-9.30 (brm, 2.49H).

[Example 20] Synthesis of α-D-PGA-D-PAE

In a 20-mL sample bottle, α-D-PGA sodium salt (408 mg) and distilled water (14.4 mL) were measured and dissolved. The solution was then ice-cooled. At ice temperature, WSC.HCl (540 mg) was added and stirred for 5 minutes. D-PAE.HCl (387 mg) was added and vigorously stirred for 1 hour at ice temperature. The solution was then stirred for 12 hours at room temperature. At room temperature, 2 M hydrochloric acid (0.5 mL) was added dropwise and stirred for 1.5 hours. A precipitate was sucked and filtered and was washed with distilled water (15 mL) twice. The precipitate was dried under reduced pressure at room temperature to acquire α-D-PGA-D-PAE (579 mg, PAE introduction rate: 77%, moisture: 0.97%).
$^1$H NMR (500 MHz, DMSO-$d_6$) δ 0.98-1.06 (brm, 3.35H), 1.50-2.35 (brm, 5.18H), 2.55-2.80 (brm, 0.96H), 2.80-3.05 (brm, 2.31H), 3.05-3.80 (brm, 2.72H), 3.90-4.80 (brm, 4.35H), 7.00-7.40 (brm, 5H, a relative value when the protons of the phenyl group of the phenylalanyl group are assumed as 5.0H), 7.70-9.30 (brm, 2.31H).

[Example 21] Synthesis of α-D-PGA-L-PAE

In a 20-mL sample bottle, α-D-PGA sodium salt (408 mg) and distilled water (14.4 mL) were measured and dissolved.

The solution was then ice-cooled. At ice temperature, WSC.HCl (540 mg) was added and stirred for 5 minutes. L-PAE.HCl (387 mg) was added and vigorously stirred for 1 hour at ice temperature. The solution was then stirred for 12 hours at room temperature. At room temperature, 2 M hydrochloric acid (0.5 mL) was added dropwise and stirred for 1.5 hours. A precipitate was sucked and filtered and was washed with distilled water (15 mL) twice. The precipitate was dried under reduced pressure at room temperature to acquire α-D-PGA-L-PAE (605 mg, PAE introduction rate: 76%, moisture: 1.09%).

$^1$H NMR (500 MHz, DMSO-$d_6$) δ 0.98-1.04 (brm, 3.44H), 1.50-2.40 (brm, 5.26H), 2.55-2.75 (brm, 1.02H), 2.80-3.05 (brm, 2.32H), 3.05-3.80 (brm, 3.00H), 3.90-4.70 (brm, 4.37H), 7.00-7.45 (brm, 5H, a relative value when the protons of the phenyl group of the phenylalanyl group are assumed as 5.0H), 7.70-9.30 (brm, 2.34H).

[Example 22] Synthesis of αβ-DL-Poly Asp-D-PAE

In a 20-mL sample bottle, αβ-DL-Poly Asp sodium salt (136 mg) and distilled water (4.8 mL) were measured and dissolved. The solution was then ice-cooled. At ice temperature, WSC.HCl (180 mg) was added and stirred for 5 minutes. D-PAE.HCl (129 mg) was added and vigorously stirred for 1.5 hours at ice temperature. The solution was then stirred for 13 hours at room temperature. At room temperature, 2 M hydrochloric acid (0.2 mL) was added and stirred for 1.5 hours. A precipitate was sucked and filtered and was washed with distilled water (5 mL) twice. The precipitate was dried under reduced pressure at room temperature to acquire αβ-DL-Poly Asp-D-PAE (183 mg, PAE introduction rate: about 63%, moisture: 2.37%).

$^1$H NMR (500 MHz, DMSO-$d_6$) δ 0.75-1.25 (brm, 3.30H), 1.60-2.80 (brm, 3.17H), 2.80-3.75 (brm, 6.28H), 3.75-4.15 (brm, 2.06H), 4.15-5.50 (brm, 2.70H), 6.90-7.45 (brm, 5H, a relative value when the protons of the phenyl group of the phenylalanyl group are assumed as 5.0H), 7.60-9.20 (brm, 2.35H).

[Example 23] Synthesis of αβ-DL-Poly Asp-L-PAE

In a 20-mL sample bottle, αβ-DL-Poly Asp sodium salt (136 mg) and distilled water (4.8 mL) were measured and dissolved. The solution was then ice-cooled. At ice temperature, WSC.HCl (180 mg) was added and stirred for 5 minutes. L-PAE.HCl (129 mg) was added and vigorously stirred for 1.5 hours at ice temperature. The solution was then stirred for 16 hours at room temperature. At room temperature, 2 M hydrochloric acid (0.2 mL) was added and stirred for 1.5 hours. A precipitate was sucked and filtered and was washed with distilled water (5 mL) twice. The precipitate was dried under reduced pressure at room temperature to acquire αβ-DL-Poly Asp-L-PAE (176 mg, PAE introduction rate: about 62%, moisture: 2.68%).

$^1$H NMR (500 MHz, DMSO-$d_6$) δ 0.80-1.30 (brm, 3.23H), 1.60-2.80 (brm, 3.22H), 2.80-3.80 (brm, 6.41H), 3.80-4.20 (brm, 2.08H), 4.20-5.30 (brm, 2.75H), 6.90-7.45 (brm, 5H, a relative value when the protons of the phenyl group of the phenylalanyl group are assumed as 5.0H), 7.60-9.30 (brm, 2.35H).

[Comparison Example 1] Synthesis of γ-PGA-PAE by Desalting Method

In a 200-mL conical flask, NaHCO$_3$ (0.42 g) and distilled water (100 mL) were measured and sufficiently stirred. After γ-PGA (0.61 g) was added at room temperature and stirred for 30 minutes and dissolved at room temperature, the solution was ice-cooled and stirred for 15 minutes. At ice temperature, WSC.HCl (0.90 g) was added and stirred for 5 minutes. PAE.HCl (1.08 g) was added and vigorously stirred for 1.0 hour at ice temperature. The solution was then stirred for 22 hours at room temperature. Subsequently, a desalting membrane (Wako, Spectra/Pore 132124, 15 kDa cutoff) was used for desalting (5 L of water was changed twice for 3 days). Acquired retained liquid (about 200 mL) was frozen and then subjected to lyophilization to acquire γ-PGA-PAE (1.039 g, moisture: 5.85%). EtOH (80 mL) was added and shaken at room temperature (200 rpm, 2 hours). After centrifugal separation (4500 rpm, 30 minutes, 5° C.), supernatant was removed by decantation. This was dried under reduced pressure was conducted at room temperature to acquire γ-PGA-PAE (0.97 g, PAE introduction rate: 48%, moisture: 1.85%).

$^1$H NMR (500 MHz, DMSO-$d_6$) δ 0.9-1.3 (brs, 4.0H), 1.4-2.4 (brm, 10.1H), 2.6-2.8 (brm, 0.6H), 2.8-3.1 (brm, 3.2H), 3.35-3.6 (q, 0.6H), 3.9-5.5 (brm, 5.3H), 5.7-6.0 (0.3H), 6.9-7.5 (brm, 5.0H, a relative value when the protons of the phenyl group of the phenylalanyl group are assumed as 5.0H), 7.6-8.7 (brm, 2.6H).

[Example 24] Synthesis of Graft Copolymer (γ-PGA-Phe-OBn) of Poly(γ-Glutamic Acid) and Phenylalanine Benzyl Ester In a 100-mL Scott bottle, 1 M sodium hydroxide aqueous solution (9.0 mL) and distilled water (35 mL) were measured and sufficiently stirred. After γ-PGA (1.21 g, 148 kDa) was added at room temperature and dissolved, the solution was ice-cooled. At ice temperature, WSC.HCl (1.80 g) was added and stirred for 5 minutes. L-phenylalanine benzyl ester hydrochloride (L-H-Phe-OBn.HCl) (1.1 g) was added and vigorously stirred for 1 hour at ice temperature. The solution was then stirred for 17.5 hours at room temperature. At room temperature, 2 M hydrochloric acid (15 mL) was added dropwise and stirred for 1.5 hours. A precipitate was sucked and filtered and was washed with distilled water (50 mL). The precipitate was dried under reduced pressure at room temperature to acquire γ-PGA-Phe-OBn (1.95 g, yield: about 74.2%, Phe-OBn introduction rate: 63%, moisture: 4.67%, 72 kDa).

$^1$H NMR (500 MHz, DMSO-$d_6$) δ 0.9-1.2 (brm, 0.45H), 1.3-2.35 (brm, 6.52H), 2.6-2.8 (brm, 1.06H), 2.8-3.2 (brm, 2.161-1), 4.0-4.4 (brm, 1.56H), 4.4-4.6 (brs, 0.62H), 4.6-4.9 (brm, 0.26H), 4.9-5.2 (brm, 1.06H), 6.9-7.5 (brm, 5.0H, a relative value when the protons of the phenyl group of the phenylalanyl group are assumed as 5.0H), 7.7-9.0 (brm, 1.83H).

[Example 25] Synthesis of γ-PGA-Phe-OBn

In a 100-mL Scott bottle, 1 M sodium hydroxide aqueous solution (9.0 mL) and distilled water (35 mL) were measured and sufficiently stirred. After γ-PGA (1.21 g, 148 kDa) was added at room temperature and dissolved, the solution was ice-cooled. At ice temperature, WSC.HCl (1.80 g) was added and stirred for 5 minutes. H-Phe-OBn.HCl (0.55 g) was added and vigorously stirred for 1 hour at ice temperature. The solution was then stirred for 17.5 hours at room temperature. At room temperature, 2 M hydrochloric acid (15 mL) was added dropwise and stirred for 1.5 hours. A precipitate was sucked and filtered and was washed with distilled water (50 mL). The precipitate was dried under reduced pressure at room temperature to acquire γ-PGA-Phe-OBn (1.39 g, yield: about 72.6%, Phe-OBn introduction rate: 30%, moisture: 5.57%, 31 kDa).

$^1$H NMR (500 MHz, DMSO-d$_6$) δ 1.4-2.3 (brm, 13.99H), 2.6-2.8 (brm, 2.72H), 2.8-3.2 (brm, 4.06H), 4.0-4.49 (brm, 3.70H), 4.9-5.2 (brm, 1.33H), 7.0-7.5 (brm, 5.0H, a relative value when the protons of the phenyl group of the phenylalanyl group are assumed as 5.0H), 7.7-9.1 (brm, 3.90H).

[Example 26] Synthesis of Graft Copolymer (γ-PGA-Phe-OcPen) of Poly(γ-Glutamic Acid) and Phenylalanine Cyclopentyl Ester In a 100-mL Scott bottle, 1 M sodium hydroxide aqueous solution (9.0 mL) and distilled water (35 mL) were measured and sufficiently stirred. After γ-PGA (1.21 g, 148 kDa) was added at room temperature and dissolved, the solution was ice-cooled. At ice temperature, WSC.HCl (1.80 g) was added and stirred for 5 minutes. After (2S)-phenylalanine cyclopentyl ester hydrochloride [(2S)—H-Phe-OcPen.HCl] (1.52 g) was added, the solution was vigorously stirred for 1 hour at ice temperature. The solution was then stirred for 14 hours at room temperature. At room temperature, 2 M hydrochloric acid (13 mL) was added dropwise and stirred for 1 hour. A precipitate was sucked and filtered and was washed with distilled water (10 mL) twice. The precipitate was dried under reduced pressure at room temperature to acquire γ-PGA-Phe-OcPen (2.33 g, yield: about 96.8%, Phe-OcPen introduction rate: 57%, moisture: 2.88%, 282 kDa).

$^1$H NMR (500 MHz, DMSO-d$_6$) δ 0.9-1.2 (brm, 0.43H), 1.3-2.3 (brm, 14.97H), 2.3-2.8 (brm, 1.60H), 2.8-3.1 (brm, 2.25H), 4.0-4.4 (brm, 2.65H), 4.4-4.9 (brs, 0.24H), 4.9-5.2 (brm, 1.06H), 7.0-7.4 (brm, 5.0H, a relative value when the protons of the phenyl group of the phenylalanyl group are assumed as 5.0H), 7.7-9.2 (brm, 2.57H).

[Example 27] Synthesis of γ-PGA-Phe-OcPen

In a 100-mL Scott bottle, 1 M sodium hydroxide aqueous solution (9.0 mL) and distilled water (35 mL) were measured and sufficiently stirred. After γ-PGA (1.21 g, 148 kDa) was added at room temperature and dissolved, the solution was ice-cooled. At ice temperature, WSC.HCl (1.80 g) was added and stirred for 5 minutes. After (2S)-phenylalanine cyclopentyl ester hydrochloride [(2S)—H-Phe-OcPen.HCl] (1.01 g) was added, the solution was vigorously stirred for 1 hour at ice temperature. The solution was then stirred for 14 hours at room temperature. At room temperature, 2 M hydrochloric acid (13 mL) was added dropwise and stirred for 1 hour. A precipitate was sucked and filtered and was washed with distilled water (10 mL) twice. The precipitate was dried under reduced pressure at room temperature to acquire γ-PGA-Phe-OcPen (1.89 g, yield: about 95.8%, Phe-OcPen introduction rate: 36%, moisture: 3.51%, 93 kDa).

$^1$H NMR (500 MHz, DMSO-d$_6$) δ (brm, 0.55H), 1.3-2.3 (brm, 19.20H), 2.6-2.8 (brm, 1.48H), 2.8-3.1 (brm, 2.94H), 4.0-4.4 (brm, 3.77H), 4.4-5.2 (brm, 1.55H), 7.0-7.4 (brm, 5.0H, a relative value when the protons of the phenyl group of the phenylalanyl group are assumed as 5.0H), 7.8-9.2 (brm, 3.45H).

[Example 28] Synthesis of Graft Copolymer (γ-PGA-Phe-OtBu) of Poly(γ-Glutamic Acid) and Phenylalanine t-Butyl Ester In a 100-mL Scott bottle, 1 M sodium hydroxide aqueous solution (9.0 mL) and distilled water (35 mL) were measured and sufficiently stirred. After γ-PGA (1.21 g, 148 kDa) was added at room temperature and dissolved, the solution was ice-cooled. At ice temperature, WSC.HCl (1.80 g) was added and stirred for 5 minutes. L-phenylalanine t-butyl ester hydrochloride (L-H-Phe-OtBu.HCl) (1.94 g) was added and vigorously stirred for 1 hour at ice temperature. The solution was then stirred for 19 hours at room temperature. At room temperature, 2 M hydrochloric acid (13 mL) was added dropwise and stirred for 1 hour. A precipitate was sucked and filtered and was washed with distilled water (10 mL) twice. The precipitate was dried under reduced pressure at room temperature to acquire γ-PGA-Phe-OtBu (3.39 g, yield: about 98.2%, Phe-OtBu introduction rate: 78%, moisture: 25.04%, 106 kDa).

$^1$H NMR (500 MHz, DMSO-d$_6$) δ 0.9-1.5 (brm, 9.31H), 1.5-2.3 (brm, 5.27H), 2.72 (brm, 0.68H), 2.8-3.1 (brm, 2.31H), 4.1-4.5 (brm, 2.09H), 4.5-5.1 (brm, 0.05H), 7.0-7.5 (brm, 5.0H, a relative value when the protons of the phenyl group of the phenylalanyl group are assumed as 5.0H), 7.7-9.8 (brm, 2.24H).

[Example 29] Synthesis of γ-PGA-Phe-OtBu

In a 100-mL Scott bottle, 1 M sodium hydroxide aqueous solution (9.0 mL) and distilled water (35 mL) were measured and sufficiently stirred. After γ-PGA (1.21 g, 148 kDa) was added at room temperature and dissolved, the solution was ice-cooled. At ice temperature, WSC.HCl (1.80 g) was added and stirred for 5 minutes. L-phenylalanine t-butyl ester hydrochloride (L-H-Phe-OtBu.HCl) (1.45 g) was added and vigorously stirred for 1 hour at ice temperature. The solution was then stirred for 19 hours at room temperature. At room temperature, 2 M hydrochloric acid (13 mL) was added dropwise and stirred for 1 hour. A precipitate was sucked and filtered and was washed with distilled water (10 mL) twice. The precipitate was dried under reduced pressure at room temperature to acquire γ-PGA-Phe-OtBu (3.28 g, yield: about 100.0%, Phe-OtBu introduction rate: 57%, moisture: 29.72%, 71 kDa).

$^1$H NMR (500 MHz, DMSO-d$_6$) δ 0.9-1.5 (brm, 9.31H), 1.5-2.3 (brm, 5.27H), 2.72 (brm, 0.68H), 2.8-3.1 (brm, 2.31H), 4.1-4.5 (brm, 2.09H), 4.4-5.1 (brm, 0.05H), 7.0-7.5 (brm, 5.0H, a relative value when the protons of the phenyl group of the phenylalanyl group are assumed as 5.0H), 7.7-9.8 (brm, 2.24H).

[Example 30] Synthesis of Graft Copolymer (γ-PGA-Phe-OMe) of Poly(γ-Glutamic Acid) and Phenylalanine Methyl Ester In a 100-mL Scott bottle, 1 M sodium hydroxide aqueous solution (9.0 mL) and distilled water (35 mL) were measured and sufficiently stirred. After γ-PGA (1.21 g, 148 kDa) was added at room temperature and dissolved, the solution was ice-cooled. At ice temperature, WSC.HCl (1.80 g) was added and stirred for 5 minutes. L-phenylalanine methyl ester hydrochloride (L-H-Phe-OMe.HCl) (1.62 g) was added and vigorously stirred for 1.5 hours at ice temperature. The solution was then stirred for 15 hours at room temperature. At room temperature, 2 M hydrochloric acid (14 mL) was added dropwise and stirred for 1 hour. A precipitate was sucked and filtered and was washed with distilled water (10 mL) thrice. The precipitate was dried under reduced pressure at room temperature to acquire γ-PGA-Phe-OMe (2.24 g, yield: about 99.6%, Phe-OMe introduction rate: 72%, moisture: 4.78%, 260 kDa).

¹H NMR (500 MHz, DMSO-d₆) δ 1.4-2.4 (brm, 5.53H), 2.4-2.7 (brm, 0.50H), 2.8-3.1 (brm, 2.49H), 3.5-3.7 (brm, 3.00H), 4.0-4.6 (brm, 2.36H), 4.6-5.1 (brm, 0.19H), 6.9-7.5 (brm, 5.0H, a relative value when the protons of the phenyl group of the phenylalanyl group are assumed as 5.0H), 7.7-9.2 (brm, 2.25H).

[Example 31] Synthesis of γ-PGA-Phe-OMe

In a 100-mL Scott bottle, 1 M sodium hydroxide aqueous solution (9.0 mL) and distilled water (35 mL) were measured and sufficiently stirred. After γ-PGA (1.21 g, 148 kDa) was added at room temperature and dissolved, the solution was ice-cooled. At ice temperature, WSC.HCl (1.80 g) was added and stirred for 5 minutes. L-phenylalanine methyl ester hydrochloride (L-H-Phe-OMe.HCl) (1.22 g) was added and vigorously stirred for 1.5 hours at ice temperature. The solution was then stirred for 15 hours at room temperature. At room temperature, 2 M hydrochloric acid (14 mL) was added dropwise and stirred for 1 hour. A precipitate was sucked and filtered and was washed with distilled water (10 mL) thrice. The precipitate was dried under reduced pressure at room temperature to acquire γ-PGA-Phe-OMe (2.07 g, yield: about 97.6%, Phe-OMe introduction rate: 53%, moisture: 4.70%, 205 kDa).

¹H NMR (500 MHz, DMSO-d₆) δ 1.4-2.4 (brm, 7.61H), 2.5-2.7 (brm, 0.80H), 2.8-3.1 (brm, 2.92H), 3.5-3.7 (brm, 3.00H), 4.0-4.6 (brm, 2.92H), 4.6-5.2 (brm, 0.31H), 6.9-7.5 (brm, 5.0H, a relative value when the protons of the phenyl group of the phenylalanyl group are assumed as 5.0H), 7.7-9.2 (brm, 2.71H).

[Example 32] Synthesis of Graft Copolymer (γ-PGA-Phe-OH) of Poly(γ-Glutamic Acid) and Phenylalanine In a 100-mL Scott bottle, 1 M sodium hydroxide aqueous solution (9.0 mL) and distilled water (35 mL) were measured and sufficiently stirred. After γ-PGA (1.21 g, 148 kDa) was added at room temperature and dissolved, the solution was ice-cooled. At ice temperature, WSC.HCl (1.80 g) was added and stirred for 5 minutes. A hydrochloric acid aqueous solution (13.2 mL) of L-phenylalanine (L-H-Phe-OH) (1.24 g) was added and vigorously stirred for 1 hour at ice temperature. The solution was then stirred for 14 hours at room temperature. At room temperature, 2 M hydrochloric acid (12 mL) was added dropwise and stirred for 2 hours. A precipitate was taken out and washed with distilled water (25 mL) twice. The precipitate was dried under reduced pressure at room temperature to acquire γ-PGA-Phe-OH (0.26 g, yield: about 17.3%, Phe-OH introduction rate: 19%, moisture: 7.11%, 271 kDa).

¹H NMR (500 MHz, DMSO-d₆) δ 1.5-2.4 (brm, 21.68H), 2.4-2.8 (brm, 3.09H), 2.8-3.2 (brm, 5.61H), 4.0-5.2 (brm, 8.09H), 5.3-6.2 (brm, 0.27), 6.9-7.4 (brm, 5.0H, a relative value when the protons of the phenyl group of the phenylalanyl group are assumed as 5.0H), 7.7-8.5 (brm, 4.98H).

[Example 33] Synthesis of Graft Copolymer ('γ-PGA-Phe-NH₂) of Poly(γ-Glutamic Acid) and Phenylalaninamide In a 100-mL Scott bottle, 1 M sodium hydroxide aqueous solution (9.0 mL) and distilled water (35 mL) were measured and sufficiently stirred. After γ-PGA (1.21 g, 148 kDa) was added at room temperature and dissolved, the solution was ice-cooled. At ice temperature, WSC.HCl (1.80 g) was added and stirred for 5 minutes. A hydrochloric acid aqueous solution (12 mL) of L-phenylalaninamide (L-H-Phe-NH₂) (1.24 g) was added and vigorously stirred for 1 hour at ice temperature. The solution was then stirred for 16 hours at room temperature. At room temperature, 2 M hydrochloric acid (12 mL) was added dropwise and stirred for 2 hours. A precipitate was taken out and washed with distilled water (30 mL) twice. The precipitate was dried under reduced pressure at room temperature to acquire γ-PGA-Phe-NH₂ (1.043 g, yield: about 63.3%, Phe-NH₂ introduction rate: 26%, moisture: 8.79%, 30 kDa).

¹H NMR (500 MHz, DMSO-d₆) δ 1.4-2.4 (brm, 20.81H), 2.4-2.8 (brm, 3.57H), 2.8-3.2 (brm, 7.33H), 4.0-5.2 (brm, 8.82H), 6.9-7.3 (brm, 6.57H, a relative value when 5.0H of the protons of the phenyl group of the phenylalanyl group is assumed as 6.57H), 7.3-7.7 (1.09), 7.7-8.5 (brm, 5.35H).

[Example 34] Synthesis of Graft Copolymer (γ-PGA-p-F-Phe-OEt) of Poly(γ-Glutamic Acid) and 4-Fluorophenylalanine Ethyl Ester In a 100-mL Scott bottle, 1 M sodium hydroxide aqueous solution (9.0 mL) and distilled water (35 mL) were measured and sufficiently stirred. After γ-PGA (1.21 g, 148 kDa) was added at room temperature and dissolved, the solution was ice-cooled. At ice temperature, WSC.HCl (1.80 g) was added and stirred for 5 minutes. L-4-fluorophenylalanine ethyl ester hydrochloride (L-H-p-F-Phe-OEt.HCl) (1.40 g) was added and vigorously stirred for 1 hour at ice temperature. The solution was then stirred for 12 hours at room temperature. At room temperature, 2 M hydrochloric acid (13 mL) was added dropwise and stirred for 1 hour. A precipitate was sucked and filtered and was washed with distilled water (50 mL) twice. The precipitate was dried under reduced pressure at room temperature to acquire γ-PGA-p-F-Phe-OEt (2.22 g, yield: about 96.2%, p-F-Phe-OEt introduction rate: 56%, moisture: 3.25%, 325 kDa).

¹H NMR (500 MHz, DMSO-d₆) δ 0.8-1.8 (brm, 3.38H), 1.4-2.3 (brm, 7.10), 2.4-2.7 (brm, 1.18), 2.8-3.1 (brm, 2.55H), 3.9-4.5 (brm, 4.78H), 4.5-5.2 (brm, 0.27H), 6.8-7.5 (brm, 4.00H; a relative value when the protons of the phenyl group are assumed as 4.0H), 7.7-9.2 (brm, 2.59H).

[Example 35] Synthesis of Graft Copolymer (γ-PGA-p-Cl-Phe-OEt) of Poly(γ-Glutamic Acid) and 4-Chlorophenylalanine Ethyl Ester In a 100-mL Scott bottle, 1 M sodium hydroxide aqueous solution (9.0 mL) and distilled water (35 mL) were measured and sufficiently stirred. After γ-PGA (1.21 g, 148 kDa) was added at room temperature and dissolved, the solution was ice-cooled. At ice temperature, WSC.HCl (1.80 g) was added and stirred for 5 minutes. DL-4-chlorophenylalanine ethyl ester hydrochloride (DL-H-p-Cl-Phe-OEt.HCl) (1.49 g) was added and vigorously stirred for 1 hour at ice temperature. The solution was then stirred for 15.5 hours at room temperature. At room temperature, 2 M hydrochloric acid (14 mL) was added dropwise and stirred for 1 hour. A precipitate was sucked and filtered and was washed with distilled water (20 mL) twice. The precipitate was dried under reduced pressure at room temperature to acquire γ-PGA-p-Cl-Phe-OEt (2.26 g, yield: about 96.6%, p-Cl-Phe-OEt introduction rate: 58%, moisture: 3.65%, 284 kDa).

¹H NMR (500 MHz, DMSO-d₆) δ 1.0-1.3 (brm, 3.30H), 1.4-2.4 (brm, 6.95), 2.4-2.7 (brm, 1.19), 2.8-3.1 (brm, 2.68H), 3.9-4.5 (brm, 4.70H), 4.5-5.2 (brm, 0.20H), 7.0-7.5

(brm, 4.00H; a relative value when the protons of the phenyl group are assumed as 4.0H), 7.7-9.2 (brm, 2.57H).

[Example 36] Synthesis of Graft Copolymer (γ-PGA-p-Br-Phe-OEt) of Poly(γ-Glutamic Acid) and 4-Bromophenylalanine Ethyl Ester In a 100-mL Scott bottle, 1 M sodium hydroxide aqueous solution (9.0 mL) and distilled water (35 mL) were measured and sufficiently stirred. After γ-PGA (1.21 g, 148 kDa) was added at room temperature and dissolved, the solution was ice-cooled. At ice temperature, WSC.HCl (1.80 g) was added and stirred for 5 minutes. (S)-4-bromophenylalanine ethyl ester hydrochloride [(S)—H-p-Br-Phe-OEt.HCl] (1.74 g) was added and vigorously stirred for 1 hour at ice temperature. The solution was then stirred for 13 hours at room temperature. At room temperature, 2 M hydrochloric acid (13 mL) was added dropwise and stirred for 1 hour. A precipitate was sucked and filtered and was washed with distilled water (20 mL) twice. The precipitate was dried under reduced pressure at room temperature to acquire γ-PGA-p-Br-Phe-OEt (2.43 g, yield: about 97.2%, p-Br-Phe-OEt introduction rate: 56%, moisture: 2.39%, 185 kDa).
$^1$H NMR (500 MHz, DMSO-$d_6$) δ 0.9-1.3 (brm, 3.34H), 1.4-2.4 (brm, 7.17), 2.4-2.7 (brm, 1.46), 2.7-3.1 (brm, 2.76H), 3.9-4.5 (brm, 4.90H), 4.5-5.2 (brm, 0.33H), 6.9-7.3 (brm, 4.00H; 2.0H was defined as a relative value out of 4.0H for the protons of the phenyl group), 7.3-7.7 (brm, 2.0H), 7.7-9.2 (brm, 2.63H).

[Example 37] Synthesis of Graft Copolymer (γ-PGA-p-NO$_2$-Phe-OEt) of Poly(γ-Glutamic Acid) and 4-Nitrophenylalanine Ethyl Ester In a 100-mL Scott bottle, 1 M sodium hydroxide aqueous solution (9.0 mL) and distilled water (35 mL) were measured and sufficiently stirred. After γ-PGA (1.21 g, 148 kDa) was added at room temperature and dissolved, the solution was ice-cooled. At ice temperature, WSC.HCl (1.80 g) was added and stirred for 5 minutes. D-p-nitrophenylalanine ethyl ester hydrochloride (D-H-p-NO$_2$-Phe-OEt.HCl) (1.55 g) was added and vigorously stirred for 1 hour at ice temperature. The solution was then stirred for 12 hours at room temperature. At room temperature, 2 M hydrochloric acid (13 mL) was added dropwise and stirred for 1 hour. A precipitate was sucked and filtered and was washed with distilled water (50 mL) twice. The precipitate was dried under reduced pressure at room temperature to acquire γ-PGA-p-NO$_2$-Phe-OEt (2.39 g, yield: about 95.7%, p-NO$_2$-Phe-OEt introduction rate: 58%, moisture: 3.42%, 331 kDa).
$^1$H NMR (500 MHz, DMSO-$d_6$) δ 0.8-1.3 (brm, 3.28H), 1.4-2.4 (brm, 6.90), 2.4-2.7 (brm, 1.06), 2.7-3.3 (brm, 3.76H), 3.9-5.1 (brm, 1.25H), 7.3-7.6 (brm, 2.00H; 2.0H was defined as a relative value out of 4.0H for the protons of the phenyl group), 7.6-9.2 (brm, 0.03H).

[Example 38] Synthesis of Graft Copolymer (γ-PGA-p-OiPr-Phe-OEt) of Poly(γ-Glutamic Acid) and O-(1-Methylethyl)-L-Tyrosine Ethyl Ester In a 100-mL Scott bottle, 1 M sodium hydroxide aqueous solution (9.0 mL) and distilled water (35 mL) were measured and sufficiently stirred. After γ-PGA (1.21 g, 148 kDa) was added at room temperature and dissolved, the solution was ice-cooled. At ice temperature, WSC.HCl (1.80 g) was added and stirred for 5 minutes. O-(1-methylethyl)-L-tyrosine ethyl ester hydrochloride (L-H-p-OiPr-Phe-OEt.HCl) (1.62 g) was added and vigorously stirred for 1 hour at ice temperature. The solution was then stirred for 14 hours at room temperature. At room temperature, 2 M hydrochloric acid (13 mL) was added dropwise and stirred for 1 hour. A precipitate was sucked and filtered and was washed with distilled water (10 mL) twice. The precipitate was dried under reduced pressure at room temperature to acquire γ-PGA-p-OiPr-Phe-OEt (2.43 g, yield: about 95.6%, p-OiPr-Phe-OEt introduction rate: 57%, moisture: 2.82%, 309 kDa).
$^1$H NMR (500 MHz, DMSO-$d_6$) δ 0.9-1.3 (brm, 9.58H), 1.5-2.4 (brm, 7.11), 2.6-2.8 (brm, 0.85), 2.8-3.1 (brm, 2.52H), 3.9-4.9 (brm, 5.92H), 6.78 (brs, 2.0H; 2.0H was defined as a relative value out of 4.0H for the protons of the phenyl group), 7.0-7.1 (brm, 2.0H), 7.8-9.2 (brm, 2.76H).

[Example 39] Synthesis of Graft Copolymer (γ-PGA-α-Phegly-OEt) of Poly(γ-Glutamic Acid) and α-Phenylglycine Ethyl Ester In a 100-mL Scott bottle, 1 M sodium hydroxide aqueous solution (9.0 mL) and distilled water (35 mL) were measured and sufficiently stirred. After γ-PGA (1.21 g, 148 kDa) was added at room temperature and dissolved, the solution was ice-cooled. At ice temperature, WSC.HCl (1.80 g) was added and stirred for 5 minutes. D-α-phenylglycine ethyl ester hydrochloride (D-H-α-Phegly-OEt.HCl) (1.22 g) was added and vigorously stirred for 1 hour at ice temperature. The solution was then stirred for 13 hours at room temperature. At room temperature, 2 M hydrochloric acid (13 mL) was added dropwise and stirred for 1 hour. A precipitate was sucked and filtered and was washed with distilled water (20 mL) twice. The precipitate was dried under reduced pressure at room temperature to acquire γ-PGA-α-Phegly-OEt (2.00 g, yield: about 96.1%, α-Phegly-OEt introduction rate: 59%, moisture: 3.18%, 126 kDa).
$^1$H NMR (500 MHz, DMSO-$d_6$) δ 0.9-1.3 (brm, 3.23H), 1.5-2.3 (brm, 6.84H), 2.4-2.7 (brm, 1.21H), 2.7-3.0 (brm, 0.41H), 4.0-4.2 (brs, 2.61H), 4.3-4.5 (brm, 1.03H), 4.5-5.2 (brs, 0.19H), 5.3-5.4 (brm, 0.99H), 7.0-7.6 (brm, 5.0H, a relative value when the protons of the phenyl group are assumed as 5.0H), 7.8-9.2 (brm, 2.56H).

[Example 40] Synthesis of Graft Copolymer (γ-PGA-Leu-OEt) of Poly(γ-Glutamic Acid) and Leucine Ethyl Ester In a 100-mL Scott bottle, 1 M sodium hydroxide aqueous solution (9.0 mL) and distilled water (35 mL) were measured and sufficiently stirred. After γ-PGA (1.21 g, 148 kDa) was added at room temperature and dissolved, the solution was ice-cooled. At ice temperature, WSC.HCl (1.80 g) was added and stirred for 5 minutes. L-leucine ethyl ester hydrochloride (L-H-Leu-OEt.HCl) (1.47 g) was added and vigorously stirred for 1 hour at ice temperature. The solution was then stirred for 6 hours at room temperature. At room temperature, 2 M hydrochloric acid (13 mL) was added dropwise and stirred for 2 hours. A precipitate was taken out and washed with distilled water (20 mL) twice. The precipitate was dried under reduced pressure at room temperature to acquire γ-PGA-Leu-OEt (2.25 g, Leu-OEt introduction rate: 48%, moisture: 5.13%, 284 kDa).
$^1$H NMR (500 MHz, DMSO-$d_6$) δ 0.7-1.0 (brm, 6.5H, indicated as a relative value), 1.1-1.3 (brm, 1.0H), 1.4-2.4 (brm, 10.1H), 2.6-2.8 (brm, 1.2H), 2.9-3.3 (brm, 1.3H), 3.9-5.2 (brm, 4.7H), 7.5-9.0 (brm, 2.7H).

[Example 41] Synthesis of Graft Copolymer (γ-PGA-Ile-OMe) of Poly(γ-Glutamic Acid) and Isoleucine Methyl Ester In a 100-mL Scott bottle, 1 M sodium hydroxide aqueous solution (9.0 mL) and distilled water (35 mL) were measured and sufficiently stirred. After γ-PGA (1.21 g, 148 kDa) was added at room temperature and dissolved, the solution was ice-cooled. At ice temperature, WSC.HCl (1.80 g) was added and stirred for 5 minutes. L-isoleucine methyl ester hydrochloride (L-H-Ile-OMe.HCl) (1.47 g) was added and vigorously stirred for 1 hour at ice temperature. The solution was then stirred for 6 hours at room temperature. At room temperature, 2 M hydrochloric acid (13 mL) was added dropwise and stirred for 2 hours. A precipitate was taken out and washed with distilled water (20 mL) thrice. The precipitate was dried under reduced pressure at room temperature to acquire γ-PGA-Ile-OMe (2.25 g, Ile-OMe introduction rate: 55%, moisture: 15.11%, 209 kDa).

$^1$H NMR (500 MHz, DMSO-$d_6$) δ 0.7-0.9 (brm, 6.0H), 1.0-1.3 (brm, 1.3H), 1.3-1.5 (brm, 1.0H), 1.6-2.4 (brm, 7.8H), 2.6-2.9 (brm, 0.8H), 2.9-3.3 (brm, 1.0H), 3.5-3.7 (brm, 3.0H, a relative value when the methyl group of $CO_2Me$ is assumed as 3.0H), 4.0-5.2 (brm, 2.7H), 7.8-9.8 (brm, 2.7H).

[Example 42] Synthesis of Graft Copolymer [γ-PGA-Cys(Bn)-OEt]Poly(γ-Glutamic Acid) and S-Benzylcysteine Ethyl Ester In a 100-mL Scott bottle, 1 M sodium hydroxide aqueous solution (9.0 mL) and distilled water (35 mL) were measured and sufficiently stirred. After γ-PGA (1.21 g, 148 kDa) was added at room temperature and dissolved, the solution was ice-cooled. At ice temperature, WSC.HCl (1.80 g) was added and stirred for 5 minutes. L-S-benzylcysteine ethyl ester hydrochloride [L-H-Cys(Bn)-OEt.HCl] (1.56 g) was added and vigorously stirred for 1 hour at ice temperature. The solution was then stirred for 17 hours at room temperature. At room temperature, 2 M hydrochloric acid (14 mL) was added dropwise and stirred for 1 hour. A precipitate was sucked and filtered and was washed with distilled water (10 mL) twice. The precipitate was dried under reduced pressure at room temperature to acquire γ-PGA-Cys(Bn)-OEt [1.36 g, Cys(Bn)-OEt introduction rate: 60%, moisture: 3.40%, 404 kDa].

$^1$H NMR (500 MHz, DMSO-$d_6$) δ 1.0-1.2 (brs, 3.3H), 1.4-2.4 (brm, 6.7H), 2.4-2.7 (brm, 0.3H), 2.6-2.8 (brm, 2.6H), 2.8-3.1 (brm, 0.6H), 4.0-4.5 (brm, 4.7H), 4.5-5.2 (brm, 0.3H), 7.1-7.5 (brm, 5.0H, a relative value when the protons of the phenyl group are assumed as 5.0H), 7.7-9.2 (brm, 2.6H).

[Example 43] Synthesis of Graft Copolymer (γ-PGA-Trp-OEt) of Poly(γ-Glutamic Acid) and Tryptophan Ethyl Ester In a 100-mL Scott bottle, 1 M sodium hydroxide aqueous solution (9.0 mL) and distilled water (35 mL) were measured and sufficiently stirred. After γ-PGA (1.21 g, 148 kDa) was added at room temperature and dissolved, the solution was ice-cooled. At ice temperature, WSC.HCl (1.80 g) was added and stirred for 5 minutes. L-tryptophan ethyl ester hydrochloride (L-H-Trp-OEt.HCl) (1.52 g) was added and vigorously stirred for 1.5 hours at ice temperature. The solution was then stirred for 22 hours at room temperature. At room temperature, 2 M hydrochloric acid (13 mL) was added dropwise and stirred for 1 hour. A precipitate was sucked and filtered and was washed with distilled water (10 mL) twice. The precipitate was dried under reduced pressure at room temperature to acquire γ-PGA-Trp-OEt (2.33 g, Trp-OEt introduction rate: 56%, moisture: 2.97%, 217 kDa).

$^1$H NMR (500 MHz, DMSO-$d_6$) δ 0.8-1.2 (brs, 3.4H), 1.5-2.4 (brm, 6.9H), 2.5-2.8 (brm, 1.0H), 2.9-3.3 (brm, 3.2H), 3.9-5.2 (brm, 4.7H), 6.8-7.6 (brm, 5.0H, a relative value when the protons of the indole group except NH are assumed as 5.0H), 7.7-9.5 (brm, 2.6H).

[Example 44] Synthesis of γ-PGA-Trp-OEt

In a 100-mL Scott bottle, 1 M sodium hydroxide aqueous solution (9.0 mL) and distilled water (35 mL) were measured and sufficiently stirred. After γ-PGA (1.21 g, 148 kDa) was added at room temperature and dissolved, the solution was ice-cooled. At ice temperature, WSC.HCl (1.80 g) was added and stirred for 5 minutes. L-tryptophan ethyl ester hydrochloride (L-H-Trp-OEt.HCl) (1.01 g) was added and vigorously stirred for 1.5 hours at ice temperature. The solution was then stirred for 22 hours at room temperature. At room temperature, 2 M hydrochloric acid (13 mL) was added dropwise and stirred for 1 hour. A precipitate was sucked and filtered and was washed with distilled water (10 mL) twice. The precipitate was dried under reduced pressure at room temperature to acquire γ-PGA-Trp-OEt (1.92 g, Trp-OEt introduction rate: 33%, moisture: 3.32%, 47 kDa).

$^1$H NMR (500 MHz, DMSO-$d_6$) δ 0.8-1.2 (brs, 3.6H), 1.5-2.4 (brm, 10.2H), 2.6-2.8 (brm, 1.7H), 2.9-3.3 (brm, 3.9H), 3.9-5.2 (brm, 6.0H), 6.9-7.6 (brm, 5.0H, a relative value when the protons of the indole group except NH are assumed as 5.0H), 7.8-9.3 (brm, 3.3H).

[Example 45] Synthesis of γ-PGA-PAE

In a 1-L four-necked flask, $Na_2CO_3$ (1.59 g) and distilled water (500 mL) were measured and sufficiently stirred. γ-PGA (3.64 g) was added at room temperature and washed with distilled water (50 mL). After stirring at room temperature for dissolution, the solution was ice-cooled. At ice temperature, WSC.HCl (5.41 g) was added and stirred for 5 minutes. PAE.HCl (6.48 g) was added and vigorously stirred for 2.0 hours at ice temperature. The solution was then stirred for 20 hours at room temperature. At room temperature, 2 M hydrochloric acid (45 mL) was added dropwise and stirred for 1.5 hours. A precipitate was sucked and filtered and was washed with distilled water (50 mL) thrice. The precipitate was dried under reduced pressure at room temperature to acquire γ-PGA-PAE (5.83 g, PAE introduction rate: 48%).

$^1$H NMR (500 MHz, DMSO-$d_6$) δ 0.9-1.3 (brs, 3.2H), 1.4-2.4 (brm, 7.4H), 2.6-2.8 (brm, 0.9H), 2.8-3.1 (brm, 2.9H), 3.9-5.5 (brm, 5.3H), 6.9-7.5 (brm, 5.0H, a relative value when the protons of the phenyl group of the phenylalanyl group are assumed as 5.0H), 7.6-8.7 (brm, 2.5H).

[Example 46] Synthesis of γ-PGA-PAE

In a 100-mL Scott bottle, 1 M sodium hydroxide aqueous solution (4.5 mL) and distilled water (20 mL) were measured and sufficiently stirred. After γ-PGA (0.61 g) was added at room temperature and dissolved, the solution was ice-cooled. At ice temperature, WSC.HCl (0.90 g) was added and stirred for 5 minutes. PAE.HCl (0.65 g) was added and vigorously stirred for 2.0 hours at ice temperature. The solution was then stirred for 21 hours at room temperature. 1 M sodium hydroxide aqueous solution (1.9 mL) was then added dropwise and stirred for 0.5 hours. Subsequently, 2 M HCl (13 mL) was added dropwise and stirred for 1 h. A precipitate was sucked and filtered and was washed with distilled water (10 mL) twice. The precipitate was dried under reduced pressure at room temperature to acquire γ-PGA-PAE (0.99 g, PAE introduction rate: 57%).

$^1$H NMR (500 MHz, DMSO-$d_6$) δ 0.9-1.3 (brs, 3.3H), 1.4-2.4 (brm, 7.1H), 2.8-3.1 (brm, 2.5H), 3.9-5.5 (brm, 5.1H), 6.9-7.5 (brm, 5.0H, a relative value when the protons of the phenyl group of the phenylalanyl group are assumed as 5.0H), 7.6-9.2 (brm, 2.6H).

[Example 47] Preparation of γ-PGA-PAE (28% Na Salt)

γ-PGA-PAE (200 mg, PAE introduction rate: 55%) and DMSO (1.5 mL) were measured and stirred at room temperature for 1 hour to acquire a solution. This solution (1.5 mL) was added dropwise into distilled water (28.5 mL). A 0.1 M NaOH aqueous solution (3.1 mL) was added dropwise with stirring at room temperature to adjust pH to 10.0. Subsequently, 0.01 M HCl (0.05 mL) was added with stirring at room temperature. This solution was frozen and then subjected to lyophilization to acquire γ-PGA-PAE (28% Na salt) (207 mg, PAE introduction rate: 58%, Na: 42000 ppm, Cl: 2271 ppm).

$^1$H NMR (500 MHz, DMSO-$d_6$) δ 0.6-1.2 (brs, 2.8H), 1.4-2.4 (brm, 6.6H), 2.8-3.1 (brm, 2.7H), 3.8-4.5 (brm, 4.1H), 4.5-5.5 (brm, 0.5H), 6.4-6.6 (brm, 0.2H), 6.7-7.5 (brm, 5.0H, a relative value when the protons of the phenyl group of the phenylalanyl group are assumed as 5.0H), 7.6-8.7 (brm, 2.1H).

[Example 48] Preparation of γ-PGA-PAE (26% Na Salt)

γ-PGA-PAE (200 mg, PAE introduction rate: 55%) and DMSO (1.5 mL) were measured and stirred at room temperature for 1 hour to acquire a solution. This solution (1.5 mL) was added dropwise into distilled water (28.5 mL). A 0.1 M NaOH aqueous solution (2.8 mL) was added dropwise with stirring at room temperature to adjust pH to 8.0. Subsequently, 0.01 M HCl (0.02 mL) was added with stirring at room temperature. This solution was frozen and then subjected to lyophilization to acquire γ-PGA-PAE (26% Na salt) (210 mg, PAE introduction rate: 56%, Na: 35000 ppm, Cl: 15662 ppm).

$^1$H NMR (500 MHz, DMSO-$d_6$) δ 0.6-1.2 (brs, 2.8H), 1.4-2.4 (brm, 6.8H), 2.8-3.1 (brm, 2.7H), 3.8-4.5 (brm, 4.1H), 4.5-5.5 (brm, 0.5H), 6.4-6.6 (brm, 0.2H), 6.7-7.5 (brm, 5.0H, a relative value when the protons of the phenyl group of the phenylalanyl group are assumed as 5.0H), 7.6-8.7 (brm, 2.0H).

[Example 49] Preparation of γ-PGA-PAE (14% Na Salt)

γ-PGA-PAE (200 mg, PAE introduction rate: 55%) and DMSO (1.5 mL) were measured and stirred at room temperature for 1 hour to acquire a solution. This solution (1.5 mL) was added dropwise into distilled water (28.5 mL). A 0.1 M NaOH aqueous solution (2.3 mL) was added dropwise with stirring at room temperature to adjust pH to 6.0. Subsequently, 0.01 M HCl (0.01 mL) was added with stirring at room temperature. This solution was frozen and then subjected to lyophilization to acquire γ-PGA-PAE (14% Na salt) (217 mg, PAE introduction rate: 53%, Na: 22000 ppm, Cl: 13282 ppm).

$^1$H NMR (500 MHz, DMSO-$d_6$) δ 0.6-1.2 (brs, 2.9H), 1.4-2.4 (brm, 7.0H), 2.8-3.1 (brm, 2.4H), 3.8-4.5 (brm, 3.9H), 4.5-5.5 (brm, 0.3H), 6.4-6.6 (brm, 0.2H), 6.7-7.5 (brm, 5.0H, a relative value when the protons of the phenyl group of the phenylalanyl group are assumed as 5.0H), 7.6-8.7 (brm, 1.6H).

[Example 50] Preparation of γ-PGA-PAE (0% Na Salt)

γ-PGA-PAE (200 mg, PAE introduction rate: 55%) and DMSO (1.5 mL) were measured and stirred at room temperature for 1 hour to acquire a solution. This solution (1.5 mL) was added dropwise into distilled water (28.5 mL). A 0.1 M NaOH aqueous solution (0.9 mL) was added dropwise with stirring at room temperature to adjust pH to 4.0. Subsequently, 0.01 M HCl (0.02 mL) was added with stirring at room temperature. This solution was frozen and then subjected to lyophilization to acquire γ-PGA-PAE (0 Na salt) (244 mg, PAE introduction rate: 51%, Na: 6900 ppm, Cl: 13785 ppm).

$^1$H NMR (500 MHz, DMSO-$d_6$) δ 0.6-1.2 (brs, 2.8H), 1.4-2.4 (brm, 6.6H), 2.8-3.1 (brm, 2.3H), 3.8-4.5 (brm, 3.8H), 4.5-5.5 (brm, 0.3H), 6.4-6.6 (brm, 0.3H), 6.7-7.5 (brm, 5.0H, a relative value when the protons of the phenyl group of the phenylalanyl group are assumed as 5.0H), 7.6-8.7 (brm, 1.4H).

[Example 51] Preparation of γ-PGA-PAE (27% K Salt)

γ-PGA-PAE (200 mg, PAE introduction rate: 55%) and DMSO (1.5 mL) were measured and stirred at room temperature for 1 hour to acquire a solution. This solution (1.5 mL) was added dropwise into distilled water (28.5 mL). A 0.1 M KOH aqueous solution (3.1 mL) was added dropwise with stirring at room temperature to adjust pH to 10.0. Subsequently, 0.01 M HCl (0.02 mL) was added with stirring at room temperature. This solution was frozen and then subjected to lyophilization to acquire γ-PGA-PAE (27 K salt) (215 mg, PAE introduction rate: 53%, K: 62000 ppm, Cl: 22769 ppm, 105 kDa).

$^1$H NMR (500 MHz, DMSO-$d_6$) δ 0.6-1.2 (brs, 2.7H), 1.4-2.4 (brm, 7.0H), 2.8-3.1 (brm, 2.3H), 3.8-4.5 (brm, 3.9H), 4.5-5.5 (brm, 0.3H), 6.4-6.6 (brm, 0.3H), 6.7-7.5 (brm, 5.0H, a relative value when the protons of the phenyl group of the phenylalanyl group are assumed as 5.0H), 7.6-8.7 (brm, 2.4H).

[Example 52] Preparation of γ-PGA-PAE (55% K Salt)

γ-PGA-PAE (200 mg, PAE introduction rate: 55%) and DMSO (1.5 mL) were measured and stirred at room temperature for 1 hour to acquire a solution. This solution (1.5 mL) was added dropwise into distilled water (28.5 mL). A 0.1 M KOH aqueous solution (2.8 mL) was added dropwise with stirring at room temperature to adjust pH to 8.0. Subsequently, 0.01 M HCl (0.02 mL) was added with stirring at room temperature. This solution was frozen and then subjected to lyophilization to acquire γ-PGA-PAE (55 K salt) (215 mg, PAE introduction rate: 48%, K: 42000 ppm, Cl: 19974 ppm, 125 kDa).

¹H NMR (500 MHz, DMSO-d$_6$) δ 0.6-1.2 (brs, 2.8H), 1.4-2.4 (brm, 7.2H), 2.8-3.1 (brm, 2.41-1), 3.8-4.5 (brm, 3.8H), 4.5-5.5 (brm, 0.3H), 6.4-6.6 (brm, 0.2H), 6.7-7.5 (brm, 5.0H, a relative value when the protons of the phenyl group of the phenylalanyl group are assumed as 5.0H), 7.6-8.7 (brm, 1.7H).

[Example 53] Preparation of γ-PGA-PAE (12% K Salt)

γ-PGA-PAE (200 mg, PAE introduction rate: 55%) and DMSO (1.5 mL) were measured and stirred at room temperature for 1 hour to acquire a solution. This solution (1.5 mL) was added dropwise into distilled water (28.5 mL). A 0.1 M KOH aqueous solution (2.2 mL) was added dropwise with stirring at room temperature to adjust pH to 6.0. Subsequently, 0.01 M HCl (0.02 mL) was added with stirring at room temperature. This solution was frozen and then subjected to lyophilization to acquire γ-PGA-PAE (12% K salt) (232 mg, PAE introduction rate: 47%, K: 33000 ppm, Cl: 11743 ppm, 138 kDa).

¹H NMR (500 MHz, DMSO-d$_6$) δ 0.6-1.2 (brs, 2.9H), 1.4-2.4 (brm, 7.2H), 2.8-3.1 (brm, 2.4H), 3.8-4.5 (brm, 4.0H), 4.5-5.5 (brm, 0.4H), 6.4-6.6 (brm, 0.3H), 6.7-7.5 (brm, 5.0H, a relative value when the protons of the phenyl group of the phenylalanyl group are assumed as 5.0H), 7.6-8.7 (brm, 2.1H).

[Example 54] Preparation of Nanoparticles of γ-PGA-PAE

γ-PGA-PAE (28%, Na salt) (2.0 mg, PAE introduction rate: 58%, Example 47) and DMSO (0.2 mL) were measured and dissolved with stirring for 2 hours at room temperature to acquire a DMSO aqueous solution (concentration: 10 mg/mL) of γ-PGA-PAE (Na salt).

A portion of this solution (concentration: 10 mg/mL, 0.2 mL) was quickly mixed into NaCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-PAE (10 mg/mL).

Subsequently, the nanoparticles of γ-PGA-PAE were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.50 M NaCl, 30 nm (PDI 0.29); 0.80 M NaCl, 167 nm (PDI 0.21); 0.95 M NaCl, 348 nm (PDI 0.27); 1.10 M NaCl, 775 nm (PDI 0.24); 1.25 M NaCl, 898 nm (PDI 0.47); 1.40 M NaCl, 988 nm (PDI 0.37); and 1.55 M NaCl, 994 nm (PDI 0.38).

[Example 55] Preparation of Nanoparticles of γ-PGA-PAE

γ-PGA-PAE (28%, Na salt) (2.0 mg, PAE introduction rate: 58%, Example 47), DMSO (0.16 mL), and distilled water (0.04 mL) were measured and dissolved with stirring for 2 hours at room temperature to acquire a DMSO aqueous solution (concentration: 10 mg/mL) of γ-PGA-PAE (Na salt).

A portion of this solution (concentration: 10 mg/mL, 0.2 mL) was quickly mixed into NaCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-PAE (10 mg/mL).

Subsequently, the nanoparticles of γ-PGA-PAE were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.80 M NaCl, 98 nm (PDI 0.21); 0.95 M NaCl, 197 nm (PDI 0.25); 1.10 M NaCl, 357 nm (PDI 0.43); 1.25 M NaCl, 577 nm (PDI 0.45); 1.40 M NaCl, 741 nm (PDI 0.51); and 1.55 M NaCl, 649 nm (PDI 0.37).

[Example 56] Preparation of Nanoparticles of γ-PGA-PAE

γ-PGA-PAE (26%, Na salt) (2.0 mg, PAE introduction rate: 56%, Example 48) and DMSO (0.2 mL) were measured and dissolved with stirring for 2 hours at room temperature to acquire a DMSO aqueous solution (concentration: 10 mg/mL) of γ-PGA-PAE (Na salt).

A portion of this solution (concentration: 10 mg/mL, 0.2 mL) was quickly mixed into NaCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-PAE (10 mg/mL).

Subsequently, the nanoparticles of γ-PGA-PAE were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.50 M NaCl, 43 nm (PDI 0.19); 0.65 M NaCl, 145 nm (PDI 0.16); 0.70 M NaCl, 278 nm (PDI 0.29); 0.75 M NaCl, 282 nm (PDI 0.28); 0.80 M NaCl, 578 nm (PDI 0.43); 0.95 M NaCl, 963 nm (PDI 0.27); and 1.10 M NaCl, 1539 nm (PDI 0.26).

[Example 57] Preparation of Nanoparticles of γ-PGA-PAE

γ-PGA-PAE (26%, Na salt) (2.0 mg, PAE introduction rate: 56%, Example 48), DMSO (0.16 mL), and distilled water (0.04 mL) were measured and dissolved with stirring for 2 hours at room temperature to acquire a DMSO aqueous solution (concentration: 10 mg/mL) of γ-PGA-PAE (Na salt).

A portion of this solution (concentration: 10 mg/mL, 0.2 mL) was quickly mixed into NaCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-PAE (10 mg/mL).

Subsequently, the nanoparticles of γ-PGA-PAE were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.70 M NaCl, 92 nm (PDI 0.18); 0.75 M NaCl, 135 nm (PDI 0.27); 0.80 M NaCl, 167 nm (PDI 0.19); 0.95 M NaCl, 398 nm (PDI 0.28); and 1.10 M NaCl, 677 nm (PDI 0.38).

[Example 58] Preparation of Nanoparticles of γ-PGA-PAE

γ-PGA-PAE (14%, Na salt) (2.0 mg, PAE introduction rate: 53%, Example 49) and DMSO (0.2 mL) were measured and dissolved with stirring for 2 hours at room temperature to acquire a DMSO aqueous solution (concentration: 10 mg/mL) of γ-PGA-PAE (Na salt).

A portion of this solution (concentration: 10 mg/mL, 0.2 mL) was quickly mixed into NaCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-PAE (10 mg/mL).

Subsequently, the nanoparticles of γ-PGA-PAE were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.40 M NaCl, 77 nm (PDI 0.15); 0.50 M NaCl, 158 nm (PDI 0.11); 0.60 M NaCl, 244 nm (PDI 0.19); 0.65 M NaCl, 310 nm (PDI 0.22); and 0.70 M NaCl, 489 nm (PDI 0.25).

[Example 59] Preparation of Nanoparticles of γ-PGA-PAE

γ-PGA-PAE (14%, Na salt) (2.0 mg, PAE introduction rate: 53%, Example 49), DMSO (0.16 mL), and distilled water (0.04 mL) were measured and dissolved with stirring for 2 hours at room temperature to acquire a DMSO aqueous solution (concentration: 10 mg/mL) of γ-PGA-PAE (Na salt).

A portion of this solution (concentration: 10 mg/mL, 0.2 mL) was quickly mixed into NaCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-PAE (10 mg/mL).

Subsequently, the nanoparticles of γ-PGA-PAE were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.60 M NaCl, 113 nm (PDI 0.11); 0.70 M NaCl, 184 nm (PDI 0.20); 0.75 M NaCl, 210 nm (PDI 0.19); 0.80 M NaCl, 312 nm (PDI 0.28); 0.90 M NaCl, 553 nm (PDI 0.31); and 1.00 M NaCl, 800 nm (PDI 0.27).

[Example 60] Preparation of Nanoparticles of γ-PGA-PAE

γ-PGA-PAE (0%, Na salt) (2.0 mg, PAE introduction rate: 51%, Example 50) and DMSO (0.2 mL) were measured and dissolved with stirring for 2 hours at room temperature to acquire a DMSO aqueous solution (concentration: 10 mg/mL) of γ-PGA-PAE (Na salt).

A portion of this solution (concentration: 10 mg/mL, 0.2 mL) was quickly mixed into NaCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-PAE (10 mg/mL).

Subsequently, the nanoparticles of γ-PGA-PAE were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.00 M NaCl, 155 nm (PDI 0.11); and 0.01 M NaCl, 217 nm (PDI 0.09).

[Example 61] Preparation of Nanoparticles of γ-PGA-PAE

γ-PGA-PAE (0%, Na salt) (2.0 mg, PAE introduction rate: 51%, Example 50), DMSO (0.16 mL), and distilled water (0.04 mL) were measured and added and dissolved with stirring for 2 hours at room temperature to acquire a DMSO aqueous solution (concentration: 10 mg/mL) of γ-PGA-PAE (Na salt).

A portion of this solution (concentration: 10 mg/mL, 0.2 mL) was quickly mixed into NaCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-PAE (10 mg/mL).

Subsequently, the nanoparticles of γ-PGA-PAE were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.00 M NaCl, 140 nm (PDI 0.14); 0.01 M NaCl, 178 nm (PDI 0.07); and 0.02 M NaCl, 220 nm (PDI 0.09).

[Example 62] Preparation of Nanoparticles of γ-PGA-PAE

γ-PGA-PAE (30 mg, PAE introduction rate: 55%) and DMSO (2.4 mL) were measured and stirred at room temperature. Subsequently, an aqueous solution (0.6 mL) of $Na_2CO_3$ (12.0 mg) was added dropwise and stirred for 2 hours to acquire a DMSO aqueous solution (concentration: 10 mg/mL) of γ-PGA-PAE (Na salt).

A portion of this solution (concentration: 10 mg/mL, 0.2 mL) was quickly mixed into NaCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-PAE (10 mg/mL).

Subsequently, the nanoparticles of γ-PGA-PAE were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.95 M NaCl, 192 nm (PDI 0.42); 1.10 M NaCl, 274 nm (PDI 0.28); 1.25 M NaCl, 494 nm (PDI 0.32); 1.40 M NaCl, 810 nm (PDI 0.42); and 1.55 M NaCl, 871 nm (PDI 0.42).

[Example 63] Preparation of Nanoparticles of γ-PGA-PAE

γ-PGA-PAE (30 mg, PAE introduction rate: 55%) and DMSO (2.4 mL) were measured and stirred at room temperature. Subsequently, an aqueous solution (0.6 mL) of $Na_2CO_3$ (6.0 mg) was added dropwise and stirred for 2 hours to acquire a DMSO aqueous solution (concentration: 10 mg/mL) of γ-PGA-PAE (Na salt).

A portion of this solution (concentration: 10 mg/mL, 0.2 mL) was quickly mixed into NaCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-PAE (10 mg/mL).

Subsequently, the nanoparticles of γ-PGA-PAE were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 1.00 M NaCl, 184 nm (PDI 0.23); 1.10 M NaCl, 335 nm (PDI 0.27); 1.15 M NaCl, 553 nm (PDI 0.51); 1.20 M NaCl, 505 nm (PDI 0.32); 1.25 M NaCl, 619 nm (PDI 0.39); and 1.30 M NaCl, 727 nm (PDI 0.39).

[Example 64] Preparation of Nanoparticles of γ-PGA-PAE

γ-PGA-PAE (30 mg, PAE introduction rate: 55%) and DMSO (2.4 mL) were measured and stirred at room temperature. Subsequently, an aqueous solution (0.6 mL) of $Na_2CO_3$ (3.0 mg) was added dropwise and stirred for 2 hours to acquire a DMSO aqueous solution (concentration: 10 mg/mL) of γ-PGA-PAE (Na salt).

A portion of this solution (concentration: 10 mg/mL, 0.2 mL) was quickly mixed into NaCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-PAE (10 mg/mL).

Subsequently, the nanoparticles of γ-PGA-PAE were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.60 M NaCl, 53 nm (PDI 0.20); 0.80 M NaCl, 202 nm (PDI 0.22); 0.85 M NaCl, 245 nm (PDI 0.25); 0.90 M NaCl, 355 nm (PDI 0.29); 0.95 M NaCl, 875 nm (PDI 0.59); and 1.00 M NaCl, 676 nm (PDI 0.50).

[Example 65] Preparation of Nanoparticles of γ-PGA-PAE

γ-PGA-PAE (30 mg, PAE introduction rate: 55%) and DMSO (2.4 mL) were measured and stirred at room temperature. Subsequently, an aqueous solution (0.6 mL) of $Na_2CO_3$ (1.5 mg) was added dropwise and stirred for 2 hours to acquire a DMSO aqueous solution (concentration: 10 mg/mL) of γ-PGA-PAE (Na salt).

A portion of this solution (concentration: 10 mg/mL, 0.2 mL) was quickly mixed into NaCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-PAE (10 mg/mL).

Subsequently, the nanoparticles of γ-PGA-PAE were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.20 M NaCl, 63 nm (PDI 0.06); 0.25 M NaCl, 78 nm (PDI 0.05); 0.30 M NaCl, 112 nm (PDI 0.08); 0.35 M NaCl, 123 nm (PDI 0.09); 0.40 M NaCl, 164 nm (PDI 0.10); 0.45 M NaCl, 210 nm (PDI 0.16); 0.50 M NaCl, 459 nm (PDI 0.42); and 0.60 M NaCl, 719 nm (PDI 0.36).

[Example 66] Preparation of Nanoparticles of γ-PGA-PAE

γ-PGA-PAE (30 mg, PAE introduction rate: 55%) and DMSO (2.4 mL) were measured and stirred at room temperature. Subsequently, an aqueous solution (0.6 mL) of $Na_2HPO_4$ (12.0 mg) was added dropwise and stirred for 2 hours to acquire a DMSO aqueous solution (concentration: 10 mg/mL) of γ-PGA-PAE (Na salt).

A portion of this solution (concentration: 10 mg/mL, 0.2 mL) was quickly mixed into NaCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-PAE (10 mg/mL).

Subsequently, the nanoparticles of γ-PGA-PAE were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.50 M NaCl, 34 nm (PDI 0.21); 0.60 M NaCl, 118 nm (PDI 0.17); 0.70 M NaCl 197 nm (PDI 0.22); 0.80 M NaCl 345 nm (PDI 0.28); 0.90 M NaCl, 537 nm (PDI 0.35); and 1.00 M NaCl, 642 nm (PDI 0.28).

[Example 67] Preparation of Nanoparticles of γ-PGA-PAE

γ-PGA-PAE (30 mg, PAE introduction rate: 55%) and DMSO (2.4 mL) were measured and stirred at room temperature. Subsequently, an aqueous solution (0.6 mL) of $Na_2HPO_4$ (6.0 mg) was added dropwise and stirred for 2 hours to acquire a DMSO aqueous solution (concentration: 10 mg/mL) of γ-PGA-PAE (Na salt).

A portion of this solution (concentration: 10 mg/mL, 0.2 mL) was quickly mixed into NaCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-PAE (10 mg/mL).

Subsequently, the nanoparticles of γ-PGA-PAE were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.05 M NaCl, 31 nm (PDI 0.14); 0.20 M NaCl, 56 nm (PDI 0.07); 0.30 M NaCl, 88 nm (PDI 0.10); 0.40 M NaCl, 137 nm (PDI 0.11); 0.50 M NaCl, 236 nm (PDI 0.20); 0.60 M NaCl, 530 nm (PDI 0.48); and 0.70 M NaCl, 585 nm (PDI 0.49).

[Example 68] Preparation of Nanoparticles of γ-PGA-PAE

γ-PGA-PAE (30 mg, PAE introduction rate: 55%) and DMSO (2.4 mL) were measured and stirred at room temperature. Subsequently, an aqueous solution (0.6 mL) of $Na_2HPO_4$ (3.0 mg) was added dropwise and stirred for 2 hours to acquire a DMSO aqueous solution (concentration: 10 mg/mL) of γ-PGA-PAE (Na salt).

A portion of this solution (concentration: 10 mg/mL, 0.2 mL) was quickly mixed into NaCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-PAE (10 mg/mL).

Subsequently, the nanoparticles of γ-PGA-PAE were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.01 M NaCl, 365 nm (PDI 0.21); 0.02 M NaCl, 595 nm (PDI 0.21); 0.04 M NaCl, 1195 nm (PDI 0.25); and 0.05 M NaCl, 1057 nm (PDI 0.46).

[Example 69] Preparation of Nanoparticles of γ-PGA-PAE (K Salt)

γ-PGA-PAE (30 mg, PAE introduction rate: 55%) and DMSO (2.4 mL) were measured and stirred at room temperature. Subsequently, an aqueous solution (0.6 mL) of $K_2CO_3$ (12.0 mg) was added dropwise and stirred for 2 hours to acquire a DMSO aqueous solution (concentration: 10 mg/mL) of γ-PGA-PAE (K salt).

A portion of this solution (concentration: 10 mg/mL, 0.2 mL) was quickly mixed into KCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-PAE (10 mg/mL).

Subsequently, the nanoparticles of γ-PGA-PAE were measured in terms of mean particle diameter [Z-Ave d. (nm)] and particle diameter dispersion index (PDI) by Zetasizer Nano ZS (Malvern). When the KCl aqueous solutions of various concentrations were used for preparation, the following results were acquired: 1.40 M KCl, 415 nm (PDI 0.55); 1.50 M KCl, 595 nm (PDI 0.41); and 1.60 M KCl, 902 nm (PDI 0.54).

[Example 70] Preparation of Nanoparticles of γ-PGA-PAE (K Salt)

γ-PGA-PAE (30 mg, PAE introduction rate: 55%) and DMSO (2.4 mL) were measured and stirred at room temperature. Subsequently, an aqueous solution (0.6 mL) of $K_2CO_3$ (6.0 mg) was added dropwise and stirred for 2 hours to acquire a DMSO aqueous solution (concentration: 10 mg/mL) of γ-PGA-PAE (K salt).

A portion of this solution (concentration: 10 mg/mL, 0.2 mL) was quickly mixed into KCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-PAE (10 mg/mL).

Subsequently, the nanoparticles of γ-PGA-PAE were measured in terms of mean particle diameter [Z-Ave d. (nm)] and particle diameter dispersion index (PDI) by Zetasizer Nano ZS (Malvern). When the KCl aqueous solutions of various concentrations were used for preparation, the following results were acquired: 0.60 M KCl, 83 nm (PDI 0.29); 0.70 M KCl, 189 nm (PDI 0.25); 0.80 M KCl, 421 nm (PDI 0.30); 0.90 M KCl, 940 nm (PDI 0.26); and 0.95 M KCl, 1185 nm (PDI 0.07).

[Example 71] Preparation of Nanoparticles of γ-PGA-PAE (K Salt)

γ-PGA-PAE (30 mg, PAE introduction rate: 55%) and DMSO (2.4 mL) were measured and stirred at room temperature. Subsequently, an aqueous solution (0.6 mL) of $K_2CO_3$ (3.0 mg) was added dropwise and stirred for 2 hours to acquire a DMSO aqueous solution (concentration: 10 mg/mL) of γ-PGA-PAE (K salt).

A portion of this solution (concentration: 10 mg/mL, 0.2 mL) was quickly mixed into KCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-PAE (10 mg/mL).

Subsequently, the nanoparticles of γ-PGA-PAE were measured in terms of mean particle diameter [Z-Ave d. (nm)] and particle diameter dispersion index (PDI) by Zetasizer Nano ZS (Malvern). When the KCl aqueous solutions of various concentrations were used for preparation, the following results were acquired: 0.50 M KCl, 103 nm (PDI 0.11); 0.55 M KCl, 93 nm (PDI 0.12); 0.60 M KCl, 161 nm (PDI 0.16); 0.65 M KCl, 216 nm (PDI 0.22); 0.70 M KCl, 308 nm (PDI 0.23); 0.75 M KCl, 398 nm (PDI 0.31); and 0.80 M KCl, 612 nm (PDI 0.31).

[Example 72] Preparation of Nanoparticles of γ-PGA-PAE (K Salt)

γ-PGA-PAE (30 mg, PAE introduction rate: 55%) and DMSO (2.4 mL) were measured and stirred at room temperature. Subsequently, an aqueous solution (0.6 mL) of $K_2CO_3$ (1.5 mg) was added dropwise and stirred for 2 hours to acquire a DMSO aqueous solution (concentration: 10 mg/mL) of γ-PGA-PAE (K salt).

A portion of this solution (concentration: 10 mg/mL, 0.2 mL) was quickly mixed into KCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-PAE (10 mg/mL).

Subsequently, the nanoparticles of γ-PGA-PAE were measured in terms of mean particle diameter [Z-Ave d. (nm)] and particle diameter dispersion index (PDI) by Zetasizer Nano ZS (Malvern). When the KCl aqueous solutions of various concentrations were used for preparation, the following results were acquired: 0.05 M KCl, 105 nm (PDI 0.08); 0.08 M KCl, 153 nm (PDI 0.08); 0.10 M KCl, 198 nm (PDI 0.15); 0.12 M KCl, 266 nm (PDI 0.20); 0.15 M KCl, 356 nm (PDI 0.18); and 0.20 M KCl, 838 nm (PDI 0.29).

[Example 73] Preparation of Nanoparticles of γ-PGA-PAE (K Salt)

γ-PGA-PAE (30 mg, PAE introduction rate: 55%) and DMSO (2.4 mL) were measured and stirred at room temperature. Subsequently, an aqueous solution (0.6 mL) of $KHCO_3$ (12.0 mg) was added dropwise and stirred for 2 hours to acquire a DMSO aqueous solution (concentration: 10 mg/mL) of γ-PGA-PAE (K salt).

A portion of this solution (concentration: 10 mg/mL, 0.2 mL) was quickly mixed into KCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-PAE (10 mg/mL).

Subsequently, the nanoparticles of γ-PGA-PAE were measured in terms of mean particle diameter [Z-Ave d. (nm)] and particle diameter dispersion index (PDI) by Zetasizer Nano ZS (Malvern). When the KCl aqueous solutions of various concentrations were used for preparation, the following results were acquired: 0.70 M KCl, 127 nm (PDI 0.20); 0.80 M KCl, 263 nm (PDI 0.28); 0.90 M KCl, 479 nm (PDI 0.42); 1.00 M KCl, 1097 nm (PDI 0.47); and 1.10 M KCl, 2085 nm (PDI 0.15).

[Example 74] Preparation of Nanoparticles of γ-PGA-PAE (K Salt)

γ-PGA-PAE (30 mg, PAE introduction rate: 55%) and DMSO (2.4 mL) were measured and stirred at room temperature. Subsequently, an aqueous solution (0.6 mL) of $KHCO_3$ (6.0 mg) was added dropwise and stirred for 2 hours to acquire a DMSO aqueous solution (concentration: 10 mg/mL) of γ-PGA-PAE (K salt).

A portion of this solution (concentration: 10 mg/mL, 0.2 mL) was quickly mixed into KCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-PAE (10 mg/mL).

Subsequently, the nanoparticles of γ-PGA-PAE were measured in terms of mean particle diameter [Z-Ave d. (nm)] and particle diameter dispersion index (PDI) by Zetasizer Nano ZS (Malvern). When the KCl aqueous solutions of various concentrations were used for preparation, the following results were acquired: 0.50 M KCl, 40 nm (PDI 0.16); 0.60 M KCl, 63 nm (PDI 0.18); 0.70 M KCl, 141 nm (PDI 0.18); 0.80 M KCl, 286 nm (PDI 0.27); 0.90 M KCl, 679 nm (PDI 0.49); and 1.00 M KCl, 1228 nm (PDI 0.04).

[Example 75] Preparation of Nanoparticles of γ-PGA-PAE (K Salt)

γ-PGA-PAE (30 mg, PAE introduction rate: 55%) and DMSO (2.4 mL) were measured and stirred at room temperature. Subsequently, an aqueous solution (0.6 mL) of $KHCO_3$ (3.0 mg) was added dropwise and stirred for 2 hours to acquire a DMSO aqueous solution (concentration: 10 mg/mL) of γ-PGA-PAE (K salt).

A portion of this solution (concentration: 10 mg/mL, 0.2 mL) was quickly mixed into KCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-PAE (10 mg/mL).

Subsequently, the nanoparticles of γ-PGA-PAE were measured in terms of mean particle diameter [Z-Ave d. (nm)] and particle diameter dispersion index (PDI) by Zetasizer Nano ZS (Malvern). When the KCl aqueous solutions of various concentrations were used for preparation, the following results were acquired: 0.20 M KCl, 58 nm (PDI 0.07); 0.30 M KCl, 91 nm (PDI 0.07); 0.40 M KCl, 161 nm (PDI 0.11); 0.45 M KCl, 189 nm (PDI 0.15); 0.50 M KCl, 303 nm (PDI 0.25); 0.55 M KCl, 488 nm (PDI 0.31); and 0.60 M KCl, 672 nm (PDI 0.28).

[Example 76] Preparation of Nanoparticles of γ-PGA-PAE (K Salt)

γ-PGA-PAE (30 mg, PAE introduction rate: 55%) and DMSO (2.4 mL) were measured and stirred at room temperature. Subsequently, an aqueous solution (0.6 mL) of $KHCO_3$ (1.5 mg) was added dropwise and stirred for 2 hours to acquire a DMSO aqueous solution (concentration: 10 mg/mL) of γ-PGA-PAE (K salt).

A portion of this solution (concentration: 10 mg/mL, 0.2 mL) was quickly mixed into KCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-PAE (10 mg/mL).

Subsequently, the nanoparticles of γ-PGA-PAE were measured in terms of mean particle diameter [Z-Ave d. (nm)] and particle diameter dispersion index (PDI) by Zetasizer Nano ZS (Malvern). When the KCl aqueous solutions of various concentrations were used for preparation, the following results were acquired: 0.00 M KCl, 237 nm (PDI 0.11); 0.005 M KCl, 242 nm (PDI 0.11); and 0.01 M KCl, 361 nm (PDI 0.17).

[Example 77] Preparation of Nanoparticles of γ-PGA-PAE

In a 100-mL egg-plant shaped flask, γ-PGA-PAE (1.03 g, moisture: 2.21%) and DMSO (60 mL) were measured, stirred at room temperature, and completely dissolved. At an internal temperature of 18 to 30° C., $NaHCO_3$ aqueous solution [$NaHCO_3$ (50 mg) was diluted with distilled water (20.0 mL)] was added dropwise. After stirring for 30 minutes, an acquired solution was filtered with a syringe filter (Corning, 0.2 μm). After washing with DMSO wash liquid (20 mL), the wash liquid was washed/filtered through a syringe filter and mixed. This solution was defined as a solution A (0.5 mL was sampled for study).

NaCl (2.63 g) was dissolved in Otsuka distilled water (100 mL) and filtered with a syringe filter (0.2 μm). This solution was defined as a solution B.

The solutions A and B were mixed through a ⅛" tube at a flow rate of 10 mL/minute. The mixed solution was received by a 1000-mL plastic bottle (Corning, storage bottle made of PS, 430281). Distilled water (about 800 mL) was added to this mixed solution to prepare a solution for desalting. This solution was desalted [desalting conditions: SARTOCON (registered trademark) Slice Cassette 2 kDa, TM 20-22 psi). This solution was frozen in a freezer at −40° C. This frozen solution was subjected to lyophilization to acquire nanoparticles of γ-PGA-PAE [957 mg, yield: 95.7%, moisture: 1.40%, PAE introduction rate: 57%, Z-Ave d. 522 nm (PDI 0.49)].

$^1$H NMR (500 MHz, DMSO-$d_6$) δ 0.9-1.3 (brs, 3.2H), 1.4-2.4 (brm, 7.1H), 2.6-2.8 (brm, 0.2H), 2.8-3.1 (brm, 2.3H), 3.9-4.5 (brm, 4.81-1), 4.5-5.5 (brm, 0.3H), 6.9-7.5 (brm, 5.0H, a relative value when the protons of the phenyl group of the phenylalanyl group are assumed as 5.0H), 7.6-8.7 (brm, 2.5H).

[Example 78] Preparation of Nanoparticles of γ-PGA-PAE

In a 100-mL egg-plant shaped flask, γ-PGA-PAE (3.075 g, moisture: 2.21%) and DMSO (45 mL) were measured, stirred at room temperature, and completely dissolved. At an internal temperature of 18 to 30° C., $NaHCO_3$ aqueous solution [acquired by diluting $NaHCO_3$ (300 mg) with distilled water (6.0 mL), washing with distilled water (3.0 mL) after dropping, and further dropping this wash liquid] was added dropwise. After stirring for 30 minutes, an acquired solution was filtered with a syringe filter (Corning, 0.2 μm). After washing with DMSO wash liquid (6 mL), the wash liquid was washed/filtered through a syringe filter and mixed. This solution was defined as a solution A (0.5 mL was sampled for study).

In a 1-L plastic bottle (Corning, storage bottle made of PS, 430281), NaCl (23.38 g) and Otsuka distilled water (1000 mL) were measured and dissolved. This solution was filtered by a 0.2 μm filter. This solution was defined as a solution B.

The solution A (about 60 mL) and the solution B (about 70 mL) were mixed through a ⅛" tube at a flow rate of 10 mL/minute. The mixed solution was received by a 1-L plastic bottle (Corning, storage bottle made of PS, 430281). Distilled water (about 900 mL) was added to this mixed solution to prepare a solution for desalting. This solution was desalted [desalting conditions: SARTOCON (registered trademark) Slice Cassette 10 kDa (3051443901E-SG), TM 17-18 psi, about 12 to 16 g/minute, about 3 hours]. This solution was frozen in a freezer at −40° C. This frozen solution was subjected to lyophilization to acquire nanoparticles of γ-PGA-PAE [2.68 g, yield: 83.4%, moisture: 6.72%, PAE introduction rate: 57%, Z-Ave d. 79.5 nm (PDI 0.28)].

$^1$H NMR (500 MHz, DMSO-$d_6$) δ 0.9-1.3 (brs, 3.21-1), 1.4-2.4 (brm, 7.0H), 2.8-3.1 (brm, 2.3H), 3.9-4.5 (brm, 4.5H), 4.5-5.5 (brm, 0.2H), 6.9-7.5 (brm, 5.0H, a relative value when the protons of the phenyl group of the phenylalanyl group are assumed as 5.0H), 7.6-8.7 (brm, 2.5H).

$^1$H NMR (500 MHz, $D_2O$) δ No signal. When a gain was increased for forcible observation, the following extremely small peaks were observed: 0.7-1.2 (brs, 3.0H), 1.5-2.5 (brm, 5.1H), 2.7-2.3 (brm, 1.8H), 3.7-4.2 (brm, 2.0H), 6.7-7.4 (brm, 5.0H, a relative value when the protons of the phenyl group of the phenylalanyl group are assumed as 5.0H).

[Example 79] Preparation of Nanoparticles of γ-PGA-PAE

In a 100-mL egg-plant shaped flask, γ-PGA-PAE (3.075 g, moisture: 2.21%) and DMSO (45 mL) were measured, stirred at room temperature, and completely dissolved. At an internal temperature of 18 to 30° C., NaOH aqueous solution [acquired by diluting 1 M NaOH (2.5 mL) with distilled water (4.5 mL), washing with distilled water (2.0 mL) after dropping, and further dropping this wash liquid] was added dropwise. After stirring for 30 minutes, an acquired solution was filtered with a syringe filter (Corning, 0.2 μm). After washing with DMSO wash liquid (6 mL), the wash liquid was washed/filtered through a syringe filter and mixed. This solution was defined as a solution A.

In a 1-L plastic bottle (Corning, storage bottle made of PS, 430281), NaCl (17.53 g) and Otsuka distilled water (1000 mL) were measured and dissolved. This solution was filtered by a 0.2 μm filter. This solution was defined as a solution B (0.5 mL was sampled for study).

The solution A (about 60 mL) and the solution B (about 70 mL) were mixed through a ⅛" tube at a flow rate of 10 mL/minute. The mixed solution was received by a 1-L plastic bottle (Corning, storage bottle made of PS, 430281). Distilled water (about 900 mL) was added to this mixed solution to prepare a solution for desalting. This solution was desalted [desalting conditions: SARTOCON (registered trademark) Slice Cassette 10 kDa (3051443901E-SG), TM 17-18 psi, about 12 to 16 g/minute, about 3 hours]. This solution was frozen in a freezer at −40° C. This frozen solution was subjected to lyophilization to acquire nanoparticles of γ-PGA-PAE [2.76 g, yield: 88.7%, moisture: 3.50%, PAE introduction rate: 57%, Z-Ave d. 80.2 nm (PDI 0.21)].

$^1$H NMR (500 MHz, DMSO-d$_6$) δ 0.9-1.3 (brs, 3.2H), 1.4-2.4 (brm, 7.1H), 2.6-2.8 (brm, 0.2H), 2.8-3.1 (brm, 2.3H), 3.9-4.5 (brm, 4.9H), 4.5-5.5 (brm, 0.3H), 6.9-7.5 (brm, 5.0H, a relative value when the protons of the phenyl group of the phenylalanyl group are assumed as 5.0H), 7.6-8.7 (brm, 2.7H).

[Example 80] Preparation of Nanoparticles of γ-PGA-PAE

In a 100-mL egg-plant shaped flask, γ-PGA-PAE (3.075 g, moisture: 2.21%) and DMSO (45 mL) were measured, stirred at room temperature, and completely dissolved. At an internal temperature of 18 to 30° C., Na$_2$CO$_3$ aqueous solution [acquired by diluting Na$_2$CO$_3$ (189 mg) with distilled water (6.0 mL), washing with distilled water (3.0 mL) after dropping, and further dropping this wash liquid] was added dropwise. After stirring for 30 minutes, an acquired solution was filtered with a syringe filter (Corning, 0.2 μm). After washing with DMSO wash liquid (6 mL), the wash liquid was washed/filtered through a syringe filter and mixed. This solution was defined as a solution A (0.5 mL was sampled for study).

In a 1-L plastic bottle (Corning, storage bottle made of PS, 430281), NaCl (25.13 g) and Otsuka distilled water (1000 mL) were measured and dissolved. This solution was filtered by a 0.2 μm filter. This solution was defined as a solution B.

The solution A (about 60 mL) and the solution B (about 70 mL) were mixed through a ⅛" tube at a flow rate of 10 mL/minute. The mixed solution was received by a 1-L plastic bottle (Corning, storage bottle made of PS, 430281). Distilled water (about 900 mL) was added to this mixed solution to prepare a solution for desalting. This solution was desalted [desalting conditions: SARTOCON (registered trademark) Slice Cassette 10 kDa (3051443901E-SG), TM 17-18 psi, about 12 to 16 g/minute, about 3 hours]. This solution was frozen in a freezer at −40° C. This frozen solution was subjected to lyophilization to acquire nanoparticles of γ-PGA-PAE [2.75 g, yield: 87.3%, moisture: 4.64%, PAE introduction rate: 56%, Z-Ave d. 98.5 nm (PDI 0.25)].

$^1$H NMR (500 MHz, DMSO-d$_6$) δ 0.9-1.3 (brs, 3.3H), 1.4-2.4 (brm, 7.1H), 2.6-2.8 (brm, 0.2H), 2.8-3.1 (brm, 2.3H), 3.9-4.5 (brm, 4.7H), 4.5-5.5 (brm, 0.2H), 6.9-7.5 (brm, 5.0H, a relative value when the protons of the phenyl group of the phenylalanyl group are assumed as 5.0H), 7.6-8.7 (brm, 2.5H).

[Example 81] Preparation of Nanoparticles of γ-PGA-PAE

In a 100-mL egg-plant shaped flask, γ-PGA-PAE (3.075 g, moisture: 2.21%) and DMSO (45 mL) were measured, stirred at room temperature, and completely dissolved. At an internal temperature of 18 to 30° C., Na$_2$CO$_3$ aqueous solution [acquired by diluting Na$_2$CO$_3$ (189 mg) with distilled water (6.0 mL), washing with distilled water (3.0 mL) after dropping, and further dropping this wash liquid] was added dropwise. After stirring for 30 minutes, an acquired solution was filtered with a syringe filter (Corning, 0.2 μm). After washing with DMSO wash liquid (6 mL), the wash liquid was washed/filtered through a syringe filter and mixed. This solution was defined as a solution A (0.5 mL was sampled for study).

In a 1-L plastic bottle (Corning, storage bottle made of PS, 430281), NaCl (17.53 g) and Otsuka distilled water (1000 mL) were measured and dissolved. This solution was filtered by a 0.2 μm filter. This solution was defined as a solution B.

The solution A (about 60 mL) and the solution B (about 70 mL) were mixed through a ⅛" tube at a flow rate of 10 mL/minute. The mixed solution was received by a 1-L plastic bottle (Corning, storage bottle made of PS, 430281). Distilled water (about 900 mL) was added to this mixed solution to prepare a solution for desalting. This solution was desalted [desalting conditions: SARTOCON (registered trademark) Slice Cassette 10 kDa (3051443901E-SG), TM 17-18 psi, about 12 to 16 g/minute, about 3 hours]. This solution was frozen in a freezer at −40° C. This frozen solution was subjected to lyophilization to acquire nanoparticles of γ-PGA-PAE [2.63 g, yield: 83.4%, moisture: 4.86%, PAE introduction rate: 57%, Z-Ave d. 261.5 nm (PDI 0.40)].

$^1$H NMR (500 MHz, DMSO-d$_6$) δ 0.9-1.3 (brs, 3.2H), 1.4-2.4 (brm, 7.0H), 2.6-2.8 (brm, 0.2H), 2.8-3.1 (brm, 2.2H), 3.9-4.5 (brm, 4.7H), 4.5-5.5 (brm, 0.2H), 6.9-7.5 (brm, 5.0H, a relative value when the protons of the phenyl group of the phenylalanyl group are assumed as 5.0H), 7.6-8.7 (brm, 2.4H).

[Example 82] Preparation of Nanoparticles of γ-PGA-PAE

In a 100-mL egg-plant shaped flask, γ-PGA-PAE (3.075 g, moisture: 2.21%) and DMSO (45 mL) were measured, stirred at room temperature, and completely dissolved. At an internal temperature of 18 to 30° C., Na$_2$CO$_3$ aqueous solution [acquired by diluting Na$_2$CO$_3$ (189 mg) with distilled water (6.0 mL), washing with distilled water (3.0 mL) after dropping, and further dropping this wash liquid] was added dropwise. After stirring for 30 minutes, an acquired solution was filtered with a syringe filter (Corning, 0.2 μm). After washing with DMSO wash liquid (6 mL), the wash liquid was washed/filtered through a syringe filter and mixed. This solution was defined as a solution A (0.5 mL of this solution was sampled and used for this study).

A portion of this solution A (25 μL) was quickly mixed into PBS aqueous solutions (25 μL) of various concentrations to acquire dispersion liquid. This dispersion liquid was used for measuring the nanoparticles of γ-PGA-PAE in terms of mean particle diameter [Z-Ave d. (nm)] and particle diameter dispersion index (PDI) by Zetasizer Nano ZS (Malvern). When the PBS aqueous solutions of various concentrations were used for preparation, the following results were acquired: ×1 PBS, 44 nm (PDI 0.24); ×2 PBS, 43 nm (PDI 0.23); ×3 PBS, 74 nm (PDI 0.23); ×3.1 PBS, 89 nm (PDI 0.25); and ×3.2 PBS, 138 nm (PDI 0.43).

[Example 83] Preparation of Nanoparticles of γ-PGA-PAE

In a 100-mL egg-plant shaped flask, γ-PGA-PAE (3.075 g, moisture: 2.21%) and DMSO (45 mL) were measured, stirred at room temperature, and completely dissolved. At an internal temperature of 18 to 30° C., NaHCO$_3$ aqueous solution [acquired by diluting NaHCO$_3$ (300 mg) with distilled water (6.0 mL), washing with distilled water (3.0 mL) after dropping, and further dropping this wash liquid] was added dropwise. After stirring for 30 minutes, an acquired solution was filtered with a syringe filter (Corning, 0.2 μm). After washing with DMSO wash liquid (6 mL), the wash liquid was washed/filtered through a syringe filter and mixed. This solution was defined as a solution A (0.5 mL of this solution was sampled and used for this study).

A portion of this solution A (25 μL) was quickly mixed into AcONa aqueous solutions (25 μL) of various concentrations to acquire dispersion liquid. This dispersion liquid was used for measuring the nanoparticles of γ-PGA-PAE in terms of mean particle diameter [Z-Ave d. (nm)] and particle diameter dispersion index (PDI) by Zetasizer Nano ZS (Malvern). When the AcONa aqueous solutions of various concentrations were used for preparation, the following results were acquired: 0.1 M AcONa, 38 nm (PDI 0.25); 0.2 M AcONa, 36 nm (PDI 0.23); 0.3 M AcONa, 39 nm (PDI 0.23); and 0.4 M AcONa, 68 nm (PDI 0.38).

[Example 84] Preparation of Nanoparticles of γ-PGA-PAE

In a 5-mL sample bottle, γ-PGA-PAE (60 mg, moisture: 2.21%) and EtOH (4 mL) were measured, stirred at room temperature, and suspended. At room temperature, NaHCO$_3$ aqueous solution [Na$_2$CO$_3$ (63 mg) was diluted with distilled water (3 mL) and 0.36 mL of this solution was used] was added dropwise. After stirring for 30 minutes, distilled water (1 mL) was added dropwise and an acquired solution was filtered with a syringe filter (Corning, 0.2 μm). This solution was defined as a solution A.

A portion of this solution A (50 μL) was quickly mixed into NaCl aqueous solutions (50 μL) of various concentrations to acquire dispersion liquid. This dispersion liquid was used for measuring the nanoparticles of γ-PGA-PAE in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.3 M NaCl, 35 nm (PDI 0.39); 0.4 M NaCl, 63 nm (PDI 0.48); 0.45 M NaCl, 206 nm (PDI 0.46); and 0.5 M NaCl, 415 nm (PDI 0.35).

[Example 85] Preparation of Nanoparticles of γ-PGA-Phe-OcPen

γ-PGA-Phe-OcPen (30 mg, Phe-OcPen introduction rate: 57%) and DMSO (2.4 mL) were measured and stirred at room temperature. NaOH aqueous solution (0.6 mL, equivalent to 0.051 mmol) was then added dropwise. The solution was stirred for 2 hours to acquire a DMSO aqueous solution (concentration: 10 mg/mL) of γ-PGA-Phe-OcPen (Na salt).

A portion of this solution (concentration: 10 mg/mL, 0.2 mL) was quickly mixed into NaCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-Phe-OcPen (10 mg/mL).

Subsequently, the nanoparticles of γ-PGA-Phe-OcPen were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.40 M NaCl, 39 nm (PDI 0.19); 0.50 M NaCl, 70 nm (PDI 0.18); 0.60 M NaCl, 124 nm (PDI 0.16); 0.70 M NaCl, 199 nm (PDI 0.25); 0.80 M NaCl, 314 nm (PDI 0.28); and 0.90 M NaCl, 670 nm (PDI 0.59).

[Example 86] Preparation of Nanoparticles of γ-PGA-Phe-OtBu

γ-PGA-Phe-OtBu (30 mg, Phe-OtBu introduction rate: 57%) and DMSO (2.4 mL) were measured and stirred at room temperature. An aqueous solution (0.6 mL) of NaHCO$_3$ (3.0 mg) was then added dropwise and stirred for 2 hours to acquire a DMSO aqueous solution (concentration: 10 mg/mL) of γ-PGA-Phe-OtBu (Na salt).

A portion of this solution (concentration: 10 mg/mL, 0.2 mL) was quickly mixed into NaCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-Phe-OtBu (10 mg/mL).

Subsequently, the nanoparticles of γ-PGA-Phe-OtBu were measured in terms of mean particle diameter [Z-Ave d. (nm)] and particle diameter dispersion index (PDI) by Zetasizer Nano ZS (Malvern). When the NaCl aqueous solutions of various concentrations were used, the following results were acquired: 0.20 M NaCl, 45 nm (PDI 0.25); 0.30 M NaCl, 97 nm (PDI 0.16); 0.40 M NaCl, 311 nm (PDI 0.27); 0.45 M NaCl, 685 nm (PDI 0.22); and 0.50 M NaCl, 1066 nm (PDI 0.37).

[Example 87] Preparation of Nanoparticles of γ-PGA-Phe-OtBu

γ-PGA-Phe-OtBu (30 mg, Phe-OtBu introduction rate: 57%) and DMSO (2.4 mL) were measured and stirred at room temperature. An aqueous solution (0.6 mL) of NaHCO$_3$ (1.5 mg) was then added dropwise and stirred for 2 hours to acquire a DMSO aqueous solution (concentration: 10 mg/mL) of γ-PGA-Phe-OtBu (Na salt).

A portion of this solution (concentration: 10 mg/mL, 0.2 mL) was quickly mixed into NaCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-Phe-OtBu (10 mg/mL).

Subsequently, the nanoparticles of γ-PGA-Phe-OtBu were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.20 M NaCl, 49 nm (PDI 0.46); 0.40 M NaCl, 80 nm (PDI 0.29); 0.50 M NaCl, 123 nm (PDI 0.28); 0.60 M NaCl, 202 nm (PDI 0.41); and 0.70 M NaCl, 414 nm (PDI 0.45).

[Example 88] Preparation of Nanoparticles of γ-PGA-Phe-OtBu

γ-PGA-Phe-OtBu (0.90 g, Phe-OtBu introduction rate: 57%) and DMSO (7.2 mL) were measured and stirred at room temperature. NaOH aqueous solution (1.8 mL, equivalent to 1.6 mmol) was added dropwise. The solution was stirred for 2 hours to acquire a DMSO aqueous solution (concentration: 100 mg/mL) of γ-PGA-Phe-OtBu (Na salt).

First, preliminary examination was conducted with NaCl aqueous solution. A portion of the DMSO aqueous solution (concentration: 100 mg/mL, 0.1 mL) of γ-PGA-Phe-OtBu (Na salt) was quickly mixed into NaCl aqueous solutions (0.1 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.1 mL) followed by desalting was performed twice. The acquired residue was dispersed in ×1 PBS (1.0 mL) to acquire a solution of nanoparticles of γ-PGA-Phe-OtBu (10 mg/mL). The nanoparticles were measured in terms of mean particle diameter [Z-Ave d. (nm)] and particle diameter dispersion index (PDI) by Zetasizer Nano ZS (Malvern). When the NaCl aqueous solutions of various concentrations were used, the following results were acquired: 0.20 M NaCl, 47 nm (PDI 0.24); 0.45 M NaCl, 64 nm (PDI 0.22); 0.50 M NaCl, 80 nm (PDI 0.23); and 0.55 M NaCl, 140 nm (PDI 0.42).

The scale was then increased. The DMSO aqueous solution (concentration: 100 mg/mL, 8.0 mL) of γ-PGA-Phe-OtBu (Na salt) described above was quickly mixed into 0.60 M NaCl aqueous solution (8.0 mL) to acquire dispersion liquid. The dispersion liquid was desalted and washed with water through centrifugal filtration (centrifugation conditions: 4500 rpm, 30 minutes, 5° C.). The acquired residue was dispersed in distilled water (25 mL) and subjected to lyophilization to acquire nanoparticles (849 mg) of γ-PGA-Phe-OtBu. The nanoparticles were measured in terms of mean particle diameter [Z-Ave d. (nm)] and particle diameter dispersion index (PDI) by Zetasizer Nano ZS (Malvern). The result was 105 nm (PDI 0.40).

[Example 89] Preparation of Nanoparticles of γ-PGA-Phe-OMe

γ-PGA-Phe-OMe (30 mg, Phe-OMe introduction rate: 53%) and DMSO (2.4 mL) were measured and stirred at room temperature. An aqueous solution (0.6 mL) of NaHCO$_3$ (3.0 mg) was added dropwise and stirred for 2 hours to acquire a DMSO aqueous solution (concentration: 10 mg/mL) of γ-PGA-Phe-OMe (Na salt).

A portion of this solution (concentration: 10 mg/mL, 0.2 mL) was quickly mixed into NaCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-Phe-OMe (10 mg/mL).

Subsequently, the nanoparticles of γ-PGA-Phe-OMe were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.20 M NaCl, 76 nm (PDI 0.11); 0.30 M NaCl, 154 nm (PDI 0.12); 0.35 M NaCl, 196 nm (PDI 0.14); 0.40 M NaCl, 273 nm (PDI 0.20); and 0.50 M NaCl, 468 nm (PDI 0.30).

[Example 90] Preparation of Nanoparticles of γ-PGA-Phe-OMe

γ-PGA-Phe-OMe (30 mg, Phe-OMe introduction rate: 53%) and DMSO (2.4 mL) were measured and stirred at room temperature. An aqueous solution (0.6 mL) of NaHCO$_3$ (1.5 mg) was added dropwise and stirred for 2 hours to acquire a DMSO aqueous solution (concentration: 10 mg/mL) of γ-PGA-Phe-OMe (Na salt).

A portion of this solution (concentration: 10 mg/mL, 0.2 mL) was quickly mixed into NaCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-Phe-OMe (10 mg/mL).

Subsequently, the nanoparticles of γ-PGA-Phe-OMe were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.15 M NaCl, 114 nm (PDI 0.05); 0.20 M NaCl, 173 nm (PDI 0.08); 0.25 M NaCl, 333 nm (PDI 0.26); 0.30 M NaCl, 778 nm (PDI 0.42); and 0.40 M NaCl, 2673 nm (PDI 0.17).

[Example 91] Preparation of Nanoparticles of γ-PGA-Phe-OMe

γ-PGA-Phe-OMe (0.90 g, Phe-OMe introduction rate: 53%) and DMSO (7.2 mL) were measured and stirred at room temperature. NaOH aqueous solution (1.8 mL, equivalent to 2.0 mmol) was then added dropwise. The solution was stirred for 2 hours to acquire a DMSO aqueous solution (concentration: 100 mg/mL) of γ-PGA-Phe-OMe (Na salt).

First, preliminary examination was conducted with NaCl aqueous solution. A portion of the DMSO aqueous solution (concentration: 100 mg/mL, 0.1 mL) of γ-PGA-Phe-OMe (Na salt) was quickly mixed into NaCl aqueous solutions (0.1 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.1 mL) followed by desalting was performed twice. The acquired residue was dispersed in ×1 PBS (1.0 mL) to acquire a solution of nanoparticles of γ-PGA-Phe-OMe (10 mg/mL). The nanoparticles were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.20 M NaCl, 65 nm (PDI 0.30); 0.45 M NaCl, 77 nm (PDI 0.29); 0.60 M NaCl, 98 nm (PDI 0.39); 0.65 M NaCl, 114 nm (PDI 0.44); 0.70 M NaCl, 135 nm (PDI 0.78); and 0.75 M NaCl, 170 nm (PDI 0.94).

The scale was then increased. The DMSO aqueous solution (concentration: 100 mg/mL, 8.0 mL) of γ-PGA-Phe-OMe (Na salt) described above was quickly mixed into 0.70 M NaCl aqueous solution (8.0 mL) to acquire dispersion liquid. The dispersion liquid was repeatedly desalted and washed with water through centrifugal filtration (centrifugation conditions: 4500 rpm, 30 minutes, 5° C.). The acquired residue was dispersed in distilled water (25 mL) and subjected to lyophilization to acquire nanoparticles (857 mg) of γ-PGA-Phe-OMe. The nanoparticles were measured in terms of mean particle diameter [Z-Ave d. (nm)] and particle diameter dispersion index (PDI) by Zetasizer Nano ZS (Malvern). The result was 145 nm (PDI 0.57).

[Example 92] Preparation of Nanoparticles of γ-PGA-p-F-Phe-OEt

γ-PGA-p-F-Phe-OEt (30 mg, p-F-Phe-OEt introduction rate: 56%) and DMSO (2.4 mL) were measured and stirred at room temperature. NaOH aqueous solution (0.6 mL, equivalent to 0.056 mmol) was then added dropwise and stirred for 2 hours to acquire a DMSO aqueous solution (concentration: 10 mg/mL) of γ-PGA-p-F-Phe-OEt (Na salt).

A portion of this solution (concentration: 10 mg/mL, 0.2 mL) was quickly mixed into NaCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-p-F-Phe-OEt (10 mg/mL).

Subsequently, the nanoparticles of γ-PGA-p-F-Phe-OEt were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.40 M NaCl, 28 nm (PDI 0.12); 0.50 M 55 nm (PDI 0.10); 0.70 M NaCl, 107 nm (PDI 0.22); 0.80 M NaCl, 244 nm (PDI 0.23); 0.90 M NaCl, 545 nm (PDI 0.30); 0.95 M NaCl, 782 nm (PDI 0.27); and 1.10 M NaCl, 897 nm (PDI 0.25).

[Example 93] Preparation of Nanoparticles of γ-PGA-p-Cl-Phe-OEt

γ-PGA-p-Cl-Phe-OEt (0.90 g, p-Cl-Phe-OEt introduction rate: 58%) and DMSO (7.2 mL) were measured and stirred at room temperature. NaOH aqueous solution (1.8 mL, equivalent to 1.5 mmol) was then added dropwise. The solution was stirred for 2 hours to acquire a DMSO aqueous solution (concentration: 100 mg/mL) of γ-PGA-p-Cl-Phe-OEt (Na salt).

First, preliminary examination was conducted with NaCl aqueous solution. A portion of the DMSO aqueous solution (concentration: 100 mg/mL, 0.1 mL) of γ-PGA-p-Cl-Phe-OEt (Na salt) was quickly mixed into NaCl aqueous solutions (0.1 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.1 mL) followed by desalting was performed twice. The acquired residue was dispersed in ×1 PBS (1.0 mL) to acquire a solution of nanoparticles of γ-PGA-p-Cl-Phe-OEt (10 mg/mL). The nanoparticles were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.20 M NaCl, 36 nm (PDI 0.26); 0.25 M NaCl, 76 nm (PDI 0.24); and 0.30 M NaCl, 492 nm (PDI 0.40).

The scale was then increased. The DMSO aqueous solution (concentration: 100 mg/mL, 8.0 mL) of γ-PGA-p-Cl-Phe-OEt (Na salt) described above was quickly mixed into 0.27 M NaCl aqueous solution (8.0 mL) to acquire dispersion liquid. The dispersion liquid was repeatedly desalted and washed with water through centrifugal filtration (centrifugation conditions: 4500 rpm, 30 minutes, 5° C.). The acquired residue was dispersed in distilled water (25 mL) and subjected to lyophilization to acquire nanoparticles (839 mg) of γ-PGA-p-Cl-Phe-OEt. The nanoparticles were measured in terms of mean particle diameter [Z-Ave d. (nm)] and particle diameter dispersion index (PDI) by Zetasizer Nano ZS (Malvern). The result was 67 nm (PDI 0.29).

[Example 94] Preparation of Nanoparticles of γ-PGA-p-Br-Phe-OEt

γ-PGA-p-Br-Phe-OEt (0.90 g, p-Br-Phe-OEt introduction rate: 56%) and DMSO (7.2 mL) were measured and stirred at room temperature. NaOH aqueous solution (1.8 mL, equivalent to 1.5 mmol) was then added dropwise. The solution was stirred for 2 hours to acquire a DMSO aqueous solution (concentration: 100 mg/mL) of γ-PGA-p-Br-Phe-OEt (Na salt).

First, preliminary examination was conducted with NaCl aqueous solution. A portion of the DMSO aqueous solution (concentration: 100 mg/mL, 0.1 mL) of γ-PGA-p-Br-Phe-OEt (Na salt) was quickly mixed into NaCl aqueous solutions (0.1 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.1 mL) followed by desalting was performed twice. The acquired residue was dispersed in ×1 PBS (1.0 mL) to acquire a solution of nanoparticles of γ-PGA-p-Br-Phe-OEt (10 mg/mL). The nanoparticles were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.30 M NaCl, 73 nm (PDI 0.19); 0.35 M NaCl, 131 nm (PDI 0.25); 0.40 M NaCl, 226 nm (PDI 0.27); and 0.45 M NaCl, 508 nm (PDI 0.40).

The scale was then increased. The DMSO aqueous solution (concentration: 100 mg/mL, 8.0 mL) of γ-PGA-p-Br-Phe-OEt (Na salt) described above was quickly mixed into 0.32 M NaCl aqueous solution (8.0 mL) to acquire dispersion liquid. The dispersion liquid was repeatedly desalted and washed with water through centrifugal filtration (centrifugation conditions: 4500 rpm, 30 minutes, 5° C.). The acquired residue was dispersed in distilled water (25 mL) and subjected to lyophilization to acquire nanoparticles (632 mg) of γ-PGA-p-Br-Phe-OEt. The nanoparticles were measured in terms of mean particle diameter [Z-Ave d. (nm)] and particle diameter dispersion index (PDI) by Zetasizer Nano ZS (Malvern). The result was 52 nm (PDI 0.27).

[Example 95] Preparation of Nanoparticles of γ-PGA-p-NO$_2$-Phe-OEt

γ-PGA-p-NO$_2$-Phe-OEt (30 mg, p-NO$_2$-Phe-OEt introduction rate: 58%) and DMSO (2.4 mL) were measured and stirred at room temperature. NaOH aqueous solution (0.6 mL, equivalent to 0.049 mmol) was then added dropwise and stirred for 2 hours to acquire a DMSO aqueous solution (concentration: 10 mg/mL) of γ-PGA-p-NO$_2$-Phe-OEt (Na salt).

A portion of this solution (concentration: 10 mg/mL, 0.2 mL) was quickly mixed into NaCl aqueous solutions (0.2 mL) of various concentrations to acquire dispersion liquid.

The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-p-NO$_2$-Phe-OEt (10 mg/mL).

Subsequently, the nanoparticles of γ-PGA-p-NO$_2$-Phe-OEt were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.30 M NaCl, 23 nm (PDI 0.32); 0.40 M NaCl, 32 nm (PDI 0.37); 0.45 M NaCl, 86 nm (PDI 0.26); and 0.50 M NaCl, 368 nm (PDI 0.31).

[Example 96] Preparation of Nanoparticles of γ-PGA-p-OiPr-Phe-OEt

γ-PGA-p-OiPr-Phe-OEt (30 mg, p-OiPr-Phe-OEt introduction rate: 57%) and DMSO (2.4 mL) were measured and stirred at room temperature. NaOH aqueous solution (0.6 mL, equivalent to 0.049 mmol) was then added dropwise and stirred for 2 hours to acquire a DMSO aqueous solution (concentration: 10 mg/mL) of γ-PGA-p-OiPr-Phe-OEt (Na salt).

A portion of this solution (concentration: 10 mg/mL, 0.2 mL) was quickly mixed into NaCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-p-OiPr-Phe-OEt (10 mg/mL).

Subsequently, the nanoparticles of γ-PGA-p-OiPr-Phe-OEt were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.20 M NaCl, 24 nm (PDI 0.31); 0.25 M NaCl, 23 nm (PDI 0.25); 0.30 M NaCl, 36 nm (PDI 0.37); 0.35 M NaCl, 42 nm (PDI 0.39); 0.40 M NaCl, 43 nm (PDI 0.29); and 0.50 M NaCl, 44 nm (PDI 0.30).

[Example 97] Preparation of Nanoparticles of γ-PGA-α-Phegly-OEt

γ-PGA-α-Phegly-OEt (30 mg, α-Phegly-OEt introduction rate: 59%) and DMSO (2.4 mL) were measured and stirred at room temperature. NaOH aqueous solution (0.6 mL, equivalent to 0.055 mmol) was then added dropwise and stirred for 2 hours to acquire a DMSO aqueous solution (concentration: 10 mg/mL) of γ-PGA-α-Phegly-OEt (Na salt).

A portion of this solution (concentration: 10 mg/mL, 0.2 mL) was quickly mixed into NaCl aqueous solutions (0.2 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.2 mL) followed by desalting was performed twice. The acquired residue was dispersed in ×1 PBS (0.2 mL) to acquire a solution of nanoparticles of γ-PGA-α-Phegly-OEt (10 mg/mL).

Subsequently, the nanoparticles of γ-PGA-α-Phegly-OEt were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.40 M NaCl, 32 nm (PDI 0.43); 0.45 M NaCl, 124 nm (PDI 0.81); and 0.50 M NaCl, 809 nm (PDI 0.52).

[Example 98] Preparation of Nanoparticles of αβ-DL-PolyAsp-D-PA

In a 5-mL sample bottle, αβ-DL-PolyAsp-D-PAE (50 mg, PAE introduction rate: 63%) and DMSO (0.5 mL) were measured and dissolved at room temperature. At room temperature, Na$_2$CO$_3$ aqueous solution was added dropwise [0.15 mL of solution acquired by dissolving Na$_2$CO$_3$ (63 mg) in distilled water (9 mL) was used]. After stirring for 30 minutes, an acquired solution was filtered with a syringe filter (Corning, 0.2 μm). After washing with DMSO wash liquid (0.5 mL), the wash liquid was washed/filtered through a syringe filter and mixed. This solution was defined as a solution A.

The solution A (50 μL) was quickly mixed into NaCl aqueous solutions (50 μL) of various concentrations to acquire dispersion liquid of nanoparticles of αβ-DL-PolyAsp-D-PAE. The nanoparticles were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.25 M NaCl, 554 nm (PDI 0.206); 0.20 M NaCl, 214 nm (PDI 0.064); 0.15 M NaCl, 132 nm (PDI 0.030), 0.10 M NaCl, 87 nm (PDI 0.090); and 0.05 M NaCl, 69 nm (PDI 0.628).

The solution A (500 μL) was quickly mixed into 0.20 M NaCl aqueous solution (500 μL) to acquire dispersion liquid (Z-Ave d., 72 nm, PDI 0.149). The liquid was desalted by using Amicon Ultra 0.5 (Millipore, 10 K) (centrifugation conditions: 4500 rpm, 15 minutes, 5° C.). The acquired residue was subjected to lyophilization to acquire nanoparticles of αβ-DL-PolyAsp-D-PAE (7 mg, PAE introduction rate: 70%).

[Example 99] Preparation of Nanoparticles of αβ-DL-PolyAsp-L-PAE

In a 5-mL sample bottle, αβ-DL-PolyAsp-L-PAE (50 mg, PAE introduction rate: 63%) and DMSO (0.5 mL) were measured and dissolved at room temperature. At room temperature, Na$_2$CO$_3$ aqueous solution was added dropwise [0.15 mL of solution acquired by dissolving Na$_2$CO$_3$ (63 mg) in distilled water (9 mL) was used]. After stirring for 30 minutes, an acquired solution was filtered with a syringe filter (Corning, 0.2 μm). After washing with DMSO wash liquid (0.5 mL), the wash liquid was washed/filtered through a syringe filter and mixed. This solution was defined as a solution A.

The solution A (50 μL) was quickly mixed into NaCl aqueous solutions (50 μL) of various concentrations to acquire dispersion liquid of nanoparticles of αβ-DL-PolyAsp-L-PAE. The nanoparticles were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.25 M NaCl, 418 nm (PDI 0.151); 0.20 M NaCl, 236 nm (PDI 0.199); 0.15 M NaCl, 126 nm (PDI 0.108), 0.10 M NaCl, 73 nm (PDI 0.090); and 0.05 M NaCl, 57 nm (PDI 0.140).

The solution A (500 µL) was quickly mixed into 0.20 M NaCl aqueous solution (500 µL) to acquire dispersion liquid (Z-Ave d., 66 nm, PDI 0.134). The liquid was desalted by using Amicon Ultra 0.5 (Millipore, 10 K) (centrifugation conditions: 4500 rpm, 15 minutes, 5° C.). The acquired residue was subjected to lyophilization to acquire nanoparticles of αβ-DL-PolyAsp-L-PAE (7 mg, PAE introduction rate: 71%).

As described in Examples, the present invention enables the acquisition of the free form of the graft copolymer of a poly(amino acid) or a salt thereof and a hydrophobic primary amine compound or a salt thereof in a short time at a high yield, and the ionized graft copolymer was able to be acquired with a small amount of solvent (the sum of the solutions A and B).

[Example 100] Measurement of Absolute Molecular Weight of γ-PGA

The absolute molecular weights of γ-PGAs [12.1 g, 65 kDa, D:L ratio (35:65)] synthesized in accordance with Examples 5 and 6 were measured by using GPC-Max (Viscotek) under SEC-HPLC conditions [TSKgelGMP-WXL, 300×7.8 mm I.D. (dual), 0.1 M NaNO$_3$, 0.8 mL/minute, 40° C.]. After each of the γ-PGAs (129 mg) was dissolved in NaHCO$_3$ (0.50, 0.75, 1.00 1.25, and 1.50 equivalents relative to the total amount of carboxyl groups of γ-PGA; 25 mL each), deaeration was conducted to acquire five γ-PGAs associated with Na. Each of the γ-PGAs was filtered through a 0.20 µm filter and used as a sample solution used with GPC-Max. From the molecular weights acquired form the five γ-PGAs associated with Na, the absolute molecular weight value of free-body γ-PGA was calculated. The absolute molecular weights of Examples 5 and 6 were both 62 kDa.

The relative molecular weights of Examples 5 and 6 are both 65 kDa and this indicates that correlation exists between the absolute molecular weight and the relative molecular weight of γ-PGA of the present invention.

[Example 101] Synthesis of γ-PGA-PAE

In a 500-mL four-necked flask, distilled water (150 mL) and NaHCO$_3$ (0.66 g) were measured at room temperature and dissolved. To this solution, β-PGA (0.95 g, 148 kDa) was added, stirred for 30 minutes under reduced pressure, and then ice-cooled. At ice temperature, WSC.HCl (1.41 g) was added and washed with distilled water (5 mL). After this solution was stirred for 5 minutes, L-phenylalanine ethyl ester hydrochloride (PAE.HCl) (1.18 g) was added and washed with distilled water (5 mL). The solution was stirred for 1 hour at ice temperature and then stirred for 20 hours at room temperature. The solution was heated to 80° C. and 2 M hydrochloric acid was added dropwise to adjust pH to 4.0. After stirring at 80° C. for 1 hour, the solution was cooled to room temperature and stirred for 2 hours. A precipitate was sucked and filtered and was washed with distilled water (18 mL) twice. The precipitate was dried under reduced pressure at room temperature to acquire γ-PGA-PAE (1.627 g, yield: about 84.9%, PAE introduction rate: 61%, moisture: 3.9%, 91 kDa).

[Example 102] Synthesis of γ-PGA-PAE

In a 2-L four-necked flask, distilled water (950 mL) and NaHCO$_3$ (4.00 g) were measured at room temperature and dissolved. To this solution, γ-PGA (5.81 g, 148 kDa) was added, stirred for 30 minutes under reduced pressure, and then ice-cooled. At ice temperature, WSC.HCl (8.61 g) was added and washed with distilled water (5 mL). After this solution was stirred for 5 minutes, L-phenylalanine ethyl ester hydrochloride (PAE.HCl) (11.4 g) was added and washed with distilled water (5 mL). The solution was stirred for 1 hour at ice temperature and then stirred for 20 hours at room temperature. The solution was heated to 80° C. and 2 M hydrochloric acid was added dropwise to adjust pH to 1.4. After stirring at 80° C. for 1 hour, the solution was cooled to room temperature and stirred for 2 hours. A precipitate was sucked and filtered and was washed with distilled water (18 mL) twice. The precipitate was dried under reduced pressure at room temperature to acquire γ-PGA-PAE (10.47 g, yield: about 92.3%, PAE introduction rate: 69.1%, moisture: 3.4%, 100 kDa).

[Example 103] Synthesis of γ-PGA-PAE

In a 500-mL four-necked flask, distilled water (150 mL) and NaHCO$_3$ (0.66 g) were measured at room temperature and dissolved. To this solution, γ-PGA (0.95 g, 148 kDa) was added, stirred for 30 minutes under reduced pressure, and then ice-cooled. At ice temperature, WSC.HCl (1.41 g) was added and washed with distilled water (5 mL). After this solution was stirred for 5 minutes, L-phenylalanine ethyl ester hydrochloride (PAE.HCl) (1.18 g) was added and washed with distilled water (5 mL). The solution was stirred for 1 hour at ice temperature and then stirred for 20 hours at room temperature. The solution was heated to 60° C. and 2 M hydrochloric acid was added dropwise to adjust pH to 4.0. After stirring at 60° C. for 1 hour, the solution was cooled to room temperature and stirred for 2 hours. A precipitate was sucked and filtered and was washed with distilled water (18 mL) twice. The precipitate was dried under reduced pressure at room temperature to acquire γ-PGA-PAE (1.541 g, yield: about 86.9%, PAE introduction rate: 60%, moisture: 2.4%, 160 kDa).

[Example 104] Synthesis of γ-PGA-PAE

In a 2-L four-necked flask, distilled water (950 mL) and NaHCO$_3$ (4.00 g) were measured at room temperature and dissolved. To this solution, γ-PGA (5.81 g, 148 kDa) was added, stirred for 30 minutes under reduced pressure, and then ice-cooled. At ice temperature, WSC.HCl (8.61 g) was added and washed with distilled water (5 mL). After this solution was stirred for 5 minutes, L-phenylalanine ethyl ester hydrochloride (PAE.HCl) (11.4 g) was added and washed with distilled water (5 mL). The solution was stirred for 1 hour at ice temperature and then stirred for 20 hours at room temperature. The solution was heated to 60° C. and 2 M hydrochloric acid was added dropwise to adjust pH to 1.4. After stirring at 60° C. for 1 hour, the solution was cooled to room temperature and stirred for 2 hours. A precipitate was sucked and filtered and was washed with distilled water (18 mL) twice. The precipitate was dried under reduced pressure at room temperature to acquire γ-PGA-PAE (10.30 g, yield: about 91.2%, PAE introduction rate: 69%, moisture: 3.6%, 211 kDa).

[Example 105] Synthesis of γ-PGA-PAE

In a 500-mL four-necked flask, distilled water (150 mL) and NaHCO$_3$ (0.66 g) were measured at room temperature and dissolved. To this solution, γ-PGA (0.95 g, 148 kDa) was added, stirred for 30 minutes under reduced pressure, and then ice-cooled. At ice temperature, WSC.HCl (1.41 g) was added and washed with distilled water (5 mL). After this solution was stirred for 5 minutes, L-phenylalanine ethyl ester hydrochloride (PAE.HCl) (1.18 g) was added and washed with distilled water (5 mL). The solution was stirred for 1 hour at ice temperature and then stirred for 20 hours at room temperature. The solution was heated to 40° C. and 2 M hydrochloric acid was added dropwise to adjust pH to 3.5. After stirring at 40° C. for 1 hour, the solution was cooled to room temperature and stirred for 2 hours. A precipitate was sucked and filtered and was washed with distilled water (18 mL) twice. The precipitate was dried under reduced pressure at room temperature to acquire γ-PGA-PAE (1.880 g, yield: about 91.3%, PAE introduction rate: 60%, moisture: 4.3%, 203 kDa).

[Example 106] Synthesis of γ-PGA-PAE

In a 500-mL four-necked flask, distilled water (150 mL) and NaHCO$_3$ (0.66 g) were measured at room temperature and dissolved. To this solution, γ-PGA (0.95 g, 148 kDa) was added, stirred for 30 minutes under reduced pressure, and then ice-cooled. At ice temperature, WSC.HCl (1.41 g) was added and washed with distilled water (5 mL). After this solution was stirred for 5 minutes, L-phenylalanine ethyl ester hydrochloride (PAE.HCl) (1.18 g) was added and washed with distilled water (5 mL). The solution was stirred for 1 hour at ice temperature and then stirred for 20 hours at room temperature. The solution was heated to 40° C. and 2 M hydrochloric acid was added dropwise to adjust pH to 2.5. After stirring at 40° C. for 1 hour, the solution was cooled to room temperature and stirred for 2 hours. A precipitate was sucked and filtered and was washed with distilled water (18 mL) twice. The precipitate was dried under reduced pressure at room temperature to acquire γ-PGA-PAE (1.622 g, yield: about 89.9%, PAE introduction rate: 61%, moisture: 3.0%, 220 kDa).

[Example 107] Synthesis of γ-PGA-PAE

In a 2-L four-necked flask, distilled water (950 mL) and NaHCO$_3$ (4.00 g) were measured at room temperature and dissolved. To this solution, γ-PGA (5.81 g, 148 kDa) was added, stirred for 30 minutes under reduced pressure, and then ice-cooled. At ice temperature, WSC.HCl (8.61 g) was added and washed with distilled water (5 mL). After this solution was stirred for 5 minutes, L-phenylalanine ethyl ester hydrochloride (PAE.HCl) (11.4 g) was added and washed with distilled water (5 mL). The solution was stirred for 1 hour at ice temperature and then stirred for 20 hours at room temperature. The solution was heated to 40° C. and 2 M hydrochloric acid was added dropwise to adjust pH to 1.4. After stirring at 40° C. for 1 hour, the solution was cooled to room temperature and stirred for 2 hours. A precipitate was sucked and filtered and was washed with distilled water (18 mL) twice. The precipitate was dried under reduced pressure at room temperature to acquire γ-PGA-PAE (10.26 g, yield: about 92.4%, PAE introduction rate: 69%, moisture: 3.1%, 235 kDa).

[Example 108] Synthesis of γ-PGA-PAE

In a 500-mL four-necked flask, distilled water (150 mL) and NaHCO$_3$ (0.63 g) were measured at room temperature and dissolved. To this solution, γ-PGA (0.91 g, 148 kDa) was added, stirred for 30 minutes under reduced pressure, and then ice-cooled. At ice temperature, WSC.HCl (1.35 g) was added and washed with distilled water (5 mL). After this solution was stirred for 5 minutes, L-phenylalanine ethyl ester hydrochloride (PAE.HCl) (1.13 g) was added and washed with distilled water (5 mL). The solution was stirred for 1 hour at ice temperature and then stirred for 20 hours at room temperature. At room temperature, 2 M hydrochloric acid (3.3 mL) was added dropwise to adjust pH to 4.0. The solution was stirred for 2 hours at room temperature. A precipitate was sucked and filtered and was washed with distilled water (18 mL) twice. The precipitate was dried under reduced pressure at room temperature to acquire γ-PGA-PAE (1.596 g, yield: about 87.1%, PAE introduction rate: 61%, moisture: 3.4%, 207 kDa).

[Example 109] Synthesis of γ-PGA-PAE

In a 500-mL four-necked flask, distilled water (150 mL) and NaHCO$_3$ (0.63 g) were measured at room temperature and dissolved. To this solution, γ-PGA (0.91 g, 148 kDa) was added, stirred for 30 minutes under reduced pressure, and then ice-cooled. At ice temperature, WSC.HCl (1.35 g) was added and washed with distilled water (5 mL). After this solution was stirred for 5 minutes, L-phenylalanine ethyl ester hydrochloride (PAE.HCl) (1.13 g) was added and washed with distilled water (5 mL). The solution was stirred for 1 hour at ice temperature and then stirred for 20 hours at room temperature. At room temperature, 2 M hydrochloric acid (3.6 mL) was added dropwise to adjust pH to 3.5. The solution was stirred for 2 hours at room temperature. A precipitate was sucked and filtered and was washed with distilled water (18 mL) twice. The precipitate was dried under reduced pressure at room temperature to acquire γ-PGA-PAE (1.621 g, yield: about 90.5%, PAE introduction rate: 61%, moisture: 3.5%, 208 kDa).

[Example 110] Synthesis of γ-PGA-PAE

In a 500-mL four-necked flask, distilled water (150 mL) and NaHCO$_3$ (0.63 g) were measured at room temperature and dissolved. To this solution, γ-PGA (0.91 g, 148 kDa) was added, stirred for 30 minutes under reduced pressure, and then ice-cooled. At ice temperature, WSC.HCl (1.35 g) was added and washed with distilled water (5 mL). After this solution was stirred for 5 minutes, L-phenylalanine ethyl ester hydrochloride (PAE.HCl) (1.13 g) was added and washed with distilled water (5 mL). The solution was stirred for 1 hour at ice temperature and then stirred for 20 hours at room temperature. At room temperature, 2 M hydrochloric acid (3.8 mL) was added dropwise to adjust pH to 3.0. The solution was stirred for 2 hours at room temperature. A precipitate was sucked and filtered and was washed with distilled water (18 mL) twice. The precipitate was dried under reduced pressure at room temperature to acquire γ-PGA-PAE (1.543 g, yield: about 90.4%, PAE introduction rate: 63%, moisture: 3.2%, 210 kDa).

[Example 111] Synthesis of γ-PGA-PAE

In a 500-mL four-necked flask, distilled water (150 mL) and NaHCO$_3$ (0.63 g) were measured at room temperature and dissolved. To this solution, γ-PGA (0.91 g, 148 kDa) was added, stirred for 30 minutes under reduced pressure, and then ice-cooled. At ice temperature, WSC.HCl (1.35 g) was added and washed with distilled water (5 mL). After this solution was stirred for 5 minutes, L-phenylalanine ethyl ester hydrochloride (PAE.HCl) (1.13 g) was added and washed with distilled water (5 mL). The solution was stirred for 1 hour at ice temperature and then stirred for 20 hours at room temperature. At room temperature, 2 M hydrochloric acid (4.4 mL) was added dropwise to adjust pH to 2.0. The solution was stirred for 2 hours at room temperature. A precipitate was sucked and filtered and was washed with distilled water (18 mL) twice. The precipitate was dried under reduced pressure at room temperature to acquire γ-PGA-PAE (1.397 g, yield: about 90.4%, PAE introduction rate: 61%, moisture: 3.1%, 205 kDa).

[Example 112] Synthesis of γ-PGA-PAE

In a 500-mL four-necked flask, distilled water (150 mL) and NaHCO$_3$ (0.66 g) were measured at room temperature and dissolved. To this solution, γ-PGA [0.95 g, 47 kDa, the absolute molecular weight was measured by GPC-Max (Viscotek)] was added, stirred for 30 minutes under reduced pressure, and then ice-cooled. At ice temperature, WSC.HCl (1.41 g) was added and washed with distilled water (5 mL). After this solution was stirred for 5 minutes, L-phenylalanine ethyl ester hydrochloride (PAE.HCl) (1.01 g) was added and washed with distilled water (5 mL). The solution was stirred for 1 hour at ice temperature and then stirred for 20 hours at room temperature. The solution was heated to 40° C. and 2 M hydrochloric acid was added dropwise to adjust pH to 3.5. After stirring at 40° C. for 1 hour, the solution was cooled to room temperature and stirred for 2 hours. A precipitate was sucked and filtered and was washed with distilled water (18 mL) twice. The precipitate was dried under reduced pressure at room temperature to acquire γ-PGA-PAE (1.50 g, yield: about 92%, PAE introduction rate: 54%, moisture: 3.8%, 78 kDa).

[Example 113] Synthesis of γ-PGA-PAE

In a 2-L four-necked flask, distilled water (950 mL) and NaHCO$_3$ (4.00 g) were measured at room temperature and dissolved. To this solution, γ-PGA (5.81 g, 148 kDa) was added, stirred for 30 minutes under reduced pressure, and then ice-cooled. At ice temperature, WSC.HCl (8.61 g) was added and washed with distilled water (5 mL). After this solution was stirred for 5 minutes, L-phenylalanine ethyl ester hydrochloride (PAE.HCl) (7.22 g) was added and washed with distilled water (5 mL). The solution was stirred for 1 hour at ice temperature and then stirred for 20 hours at room temperature. The solution was heated to 60° C. and 2 M hydrochloric acid was added dropwise to adjust pH to 3.0. After stirring at 60° C. for 1 hour, the solution was cooled to room temperature and stirred for 2 hours. A precipitate was sucked and filtered and was washed with distilled water (18 mL) twice. The precipitate was dried under reduced pressure at room temperature to acquire γ-PGA-PAE (9.18 g, yield: about 88.8%, PAE introduction rate: 58%, moisture: 3.4%, 132 kDa).

[Example 114] Synthesis of γ-PGA-PAE

In a 2-L four-necked flask, distilled water (950 mL) and NaHCO$_3$ (4.00 g) were measured at room temperature and dissolved. To this solution, γ-PGA (5.81 g, 148 kDa) was added, stirred for 30 minutes under reduced pressure, and then ice-cooled. At ice temperature, WSC.HCl (8.61 g) was added and washed with distilled water (5 mL). After this solution was stirred for 5 minutes, L-phenylalanine ethyl ester hydrochloride (PAE.HCl) (7.22 g) was added and washed with distilled water (5 mL). The solution was stirred for 1 hour at ice temperature and then stirred for 20 hours at room temperature. The solution was heated to 80° C. and 2 M hydrochloric acid was added dropwise to adjust pH to 3.0. After stirring at 80° C. for 1 hour, the solution was cooled to room temperature and stirred for 2 hours. A precipitate was sucked and filtered and was washed with distilled water (18 mL) twice. The precipitate was dried under reduced pressure at room temperature to acquire γ-PGA-PAE (9.77 g, yield: about 88.2%, PAE introduction rate: 57%, moisture: 3.6%, 86 kDa).

[Example 115] Synthesis of γ-PGA-PAE

In a 2-L four-necked flask, distilled water (950 mL) and NaHCO$_3$ (4.00 g) were measured at room temperature and dissolved. To this solution, γ-PGA (5.81 g, 148 kDa) was added, stirred for 30 minutes under reduced pressure, and then ice-cooled. At ice temperature, WSC.HCl (8.61 g) was added and washed with distilled water (5 mL). After this solution was stirred for 5 minutes, L-phenylalanine ethyl ester hydrochloride (PAE.HCl) (5.17 g) was added and washed with distilled water (5 mL). The solution was stirred for 1 hour at ice temperature and then stirred for 20 hours at room temperature. The solution was heated to 80° C. and 2 M hydrochloric acid was added dropwise to adjust pH to 3.0. After stirring at 80° C. for 1 hour, the solution was cooled to room temperature and stirred for 2 hours. A precipitate was sucked and filtered and was washed with distilled water (18 mL) twice. The precipitate was dried under reduced pressure at room temperature to acquire γ-PGA-PAE (8.25 g, yield: about 84.4%, PAE introduction rate: 44%, moisture: 4.3%, 55 kDa).

[Example 116] Synthesis of γ-PGA-PAE

In a 100-mL Scott bottle, distilled water (35 mL) and 1M NaOH (9.0 mL) were measured at room temperature. To this solution, γ-PGA [1.21 g, 47 kDa, the absolute molecular weight was measured by GPC-Max (Viscotek)] was added, dissolved with stirring for 15 minutes, and then ice-cooled. At ice temperature, WSC.HCl (1.80 g) was added and washed with distilled water (5 mL). After this solution was stirred for 5 minutes, L-phenylalanine ethyl ester hydrochloride (PAE.HCl) (1.30 g) was added and washed with distilled water (5 mL). The solution was stirred for 1 hour at ice temperature and then stirred for 20 hours at room temperature. The solution was heated to 40° C. and 2 M hydrochloric acid (1.7 mL) was added dropwise to adjust pH to 3.5. The solution was cooled to room temperature and stirred for 1 hour. A precipitate was sucked and filtered and was washed with distilled water (20 mL) twice. The precipitate was dried under reduced pressure at room temperature to acquire γ-PGA-PAE (2.1 g, yield: about 93%, PAE introduction rate: 62%, moisture: 3.3%).

[Examples 117-1 to 117-5] Preparation of γ-PGA-PAE Na Salt

γ-PGA-PAE (1.00 g, PAE introduction rate: 57%) and distilled water (10 mL) were measured. A 1 M NaOH aqueous solution was added dropwise with stirring at room temperature to adjust pH of each solution as described in Table 1. Desalting using Amicon Ultra 15 (Millipore, 10 K) was followed by washing with distilled water (5 mL). The desalting and the washing operation were repeated thrice and an acquired solution was frozen and subjected to lyophilization to acquire each of γ-PGA-PAEs described in Table 1.

TABLE 1

| Examples | pH | Na salt (%) | Yield (g) | PAE introduction rate (%) | Na (ppm) | Cl (ppm) |
|---|---|---|---|---|---|---|
| 117-1 | 3.0 | 0 | 0.785 | 58% | 35 | 100 |
| 117-2 | 4.9 | 10 | 0.909 | 57% | 10000 | 100 |
| 117-3 | 7.4 | 23 | 0.920 | 57% | 22000 | 100 |
| 117-4 | 9.0 | 26 | 0.923 | 59% | 25000 | 100 |
| 117-5 | 11 | 43 | 0.882 | 63% | 40000 | 100 |

[Examples 118-1 to 118-12] Preparation of γ-PGA-PAE Na Salt

γ-PGA-PAE (0.8 g, PAE introduction rate: 57%) and distilled water (8 mL) were measured. A 1.74 M $Na_2CO_3$ aqueous solution was added dropwise in each amount described in Table 2 with stirring at room temperature. Desalting using Amicon Ultra 15 (Millipore, 10 K) was followed by washing with distilled water (3 mL). The ultrafiltration and the washing operation were repeated thrice and an acquired solution was frozen and subjected to lyophilization to acquire each of γ-PGA-PAEs described in Table 2.

TABLE 2

| Examples | $Na_2CO_3$ aqueous solution (mL) | Na salt (%) | Yield (g) | PAE introduction rate (%) | Na (ppm) | Cl (ppm) |
|---|---|---|---|---|---|---|
| 118-1 | 0.1 | 7 | 0.766 | 57 | 6500 | 180 |
| 118-2 | 0.2 | 16 | 0.663 | 57 | 16000 | 100 |
| 118-3 | 0.3 | 23 | 0.728 | 59 | 22000 | 200 |
| 118-4 | 0.4 | 22 | 0.747 | 58 | 21000 | 200 |
| 118-5 | 0.5 | 22 | 0.767 | 58 | 21000 | 100 |
| 118-6 | 0.6 | 25 | 0.735 | 59 | 24000 | 150 |
| 118-7 | 0.7 | 27 | 0.793 | 59 | 26000 | 100 |
| 118-8 | 0.8 | 28 | 0.768 | 59 | 27000 | 100 |
| 118-9 | 1.0 | 30 | 0.774 | 60 | 29000 | 100 |
| 118-10 | 1.2 | 31 | 0.770 | 61 | 29000 | 100 |
| 118-11 | 1.4 | 30 | 0.782 | 62 | 28000 | 100 |
| 118-12 | 1.6 | 34 | 0.790 | 63 | 32000 | 100 |

[Example 119] Preparation of Nanoparticles of γ-PGA-(Bn) Cys-OEt

γ-PGA-(Bn)Cys-OEt (100 mg, introduction rate: 60%, Example 42), DMSO (5.0 mL), and 100 mg/mL $Na_2CO_3$ aqueous solution (0.084 mL) were measured and dissolved with stirring for 2 hours at room temperature to acquire a DMSO aqueous solution (concentration: 20 mg/mL) of γ-PGA-(Bn) Cys-OEt. An acquired solution was filtered with a syringe filter (Corning, 0.2 μm) and this solution was defined as a solution A.

A portion of this solution A (concentration: 20 mg/mL, 0.05 mL) was quickly mixed into NaCl aqueous solutions (0.05 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.10 mL) followed by desalting was performed twice. The acquired residue was dispersed in 1×PBS (pH 7.4, 0.10 mL) to acquire a solution of nanoparticles of γ-PGA-(Bn)Cys-OEt (10 mg/mL). The nanoparticles of γ-PGA-(Bn)Cys-OEt were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.00 M NaCl, 33 nm (PDI 0.18); 0.10 M NaCl, 102 nm (PDI 0.08); and 0.20 M NaCl, 211 nm (PDI 0.17).

NaCl (29.2 g) was dissolved in Otsuka distilled water (5 mL) and filtered with a syringe filter (0.2 μm). This solution was defined as a solution B. A portion of the solution A (concentration: 20 mg/mL, 3.0 mL) was mixed into a portion of the solution B [0.10 M NaCl aqueous solution (3.0 mL)] to acquire dispersion liquid. The liquid was desalted by using Amicon Ultra 15 (Millipore, 10 K) (centrifugation conditions: 4500 rpm, 30 minutes, 5° C.). An operation of dispersing an acquired residue in distilled water (6.0 mL) followed by desalting was performed five times. Distilled water (10 mL) was added to the acquired residue to acquire a dispersion liquid C. A portion of the dispersion liquid C (0.05 mL) was dispersed in 1×PBS (1.0 mL) to acquire the dispersion liquid of nanoparticles (87 nm, PDI 0.09). The dispersion liquid C (4 mL) was frozen in a freezer at −30° C. This frozen liquid was subjected to lyophilization to acquire nanoparticles of γ-PGA-(Bn)Cys-OEt (15 mg).

[Example 120] Preparation of Nanoparticles of γ-PGA-Trp-OEt

γ-PGA-Trp-OEt (100 mg, introduction rate: 56%, Example 43), DMSO (5.0 mL), and 100 mg/mL $Na_2CO_3$ aqueous solution (0.128 mL) were measured and dissolved with stirring for 2 hours at room temperature to acquire a DMSO aqueous solution (concentration: 20 mg/mL) of γ-PGA-Trp-OEt. An acquired solution was filtered with a syringe filter (Corning, 0.2 μm) and this solution was defined as a solution A.

A portion of this solution A (concentration: 20 mg/mL, 0.05 mL) was quickly mixed into NaCl aqueous solutions (0.05 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.10 mL) followed by desalting was performed twice. The acquired residue was dispersed in 1×PBS (pH 7.4, 0.10 mL) to acquire a solution of nanoparticles of γ-PGA-Trp-OEt (10 mg/mL). The the nanoparticles of γ-PGA-Trp-OEt were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.00 M NaCl, 55 nm (PDI 0.12); 0.05 M NaCl, 92 nm (PDI 0.10); and 0.10 M NaCl, 153 nm (PDI 0.07).

NaCl (14.6 mg) was dissolved in Otsuka distilled water (5 mL) and filtered with a syringe filter (0.2 μm). This solution was defined as a solution B. A portion of the solution A (concentration: 20 mg/mL, 3.0 mL) was mixed into a portion of the solution B [0.05 M NaCl aqueous solution (3.0 mL)] to acquire dispersion liquid. The liquid was desalted by using Amicon Ultra 15 (Millipore, 10 K) (centrifugation conditions: 4500 rpm, 30 minutes, 5° C.). An operation of dispersing an acquired residue in distilled water (6.0 mL) followed by desalting was performed five times. Distilled water (10 mL) was added to the acquired residue to acquire a dispersion liquid C. A portion of the dispersion liquid C (0.05 mL) was dispersed in 1×PBS (1.0 mL) to acquire the dispersion liquid of nanoparticles (95 nm, PDI 0.13). The dispersion liquid C (4 mL) was frozen in a freezer at −30° C. This frozen solution was subjected to lyophilization to acquire nanoparticles of γ-PGA-Trp-OEt (16 mg).

[Example 121] Preparation of Nanoparticles of γ-PGA-PAE

γ-PGA-PAE (200 mg, introduction rate: 62%, Example 116), DMSO (10.0 mL), and 100 mg/mL $Na_2CO_3$ aqueous solution (0.178 mL) were measured and dissolved with stirring for 2 hours at room temperature to acquire a DMSO aqueous solution (concentration: 20 mg/mL) of γ-PGA-PAE. An acquired solution was filtered with a syringe filter (Corning, 0.2 μm) and this solution was defined as a solution A.

A portion of this solution A (concentration: 20 mg/mL, 0.05 mL) was quickly mixed into NaCl aqueous solutions (0.05 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.10 mL) followed by desalting was performed twice. The acquired residue was dispersed in 1×PBS (pH 7.4, 0.10 mL) to acquire a solution of nanoparticles of γ-PGA-PAE (10 mg/mL). The nanoparticles of γ-PGA-PAE were measured in terms of mean particle diameter [Z-Ave d. (nm)] and particle diameter dispersion index (PDI) by Zetasizer Nano ZS (Malvern). When the NaCl aqueous solutions of various concentrations were used for preparation, the following results were acquired: 0.00 M NaCl, 56 nm (PDI 0.13); 0.05 M NaCl, 73 nm (PDI 0.12); 0.06 M NaCl, 80 nm (PDI 0.10); 0.08 M NaCl, 91 nm (PDI 0.10); and 0.10 M NaCl, 124 nm (PDI 0.10).

NaCl (32.7 mg) was dissolved in Otsuka distilled water (7.0 mL) and filtered with a syringe filter (0.2 μm). This solution was defined as a solution B. A portion of the solution A (concentration: 20 mg/mL, 4.5 mL) was mixed into a portion of the solution B [0.08 M NaCl aqueous solution (4.5 mL)] to acquire dispersion liquid. The liquid was desalted by using Amicon Ultra 15 (Millipore, 10 K) (centrifugation conditions: 4500 rpm, 30 minutes, 5° C.). An operation of dispersing an acquired residue in distilled water (10.0 mL) followed by desalting was performed five times. Distilled water (15 mL) was added to the acquired residue to acquire a dispersion liquid C. A portion of the dispersion liquid C (0.05 mL) was dispersed in 1×PBS (1.0 mL) to acquire the dispersion liquid of nanoparticles (75 nm, PDI 0.11). The dispersion liquid C (6.0 mL) was frozen in a freezer at −30° C. This frozen solution was subjected to lyophilization to acquire nanoparticles of γ-PGA-PAE (31 mg, PAE introduction rate: 59%, moisture: 3.4%).

Production of Vaccine

[Example 122] Preparation of Liquid Mixture of Nanoparticles of γ-PGA-PAE and HA Antigen The nanoparticles of γ-PGA-PAE (84.3 mg, PAE introduction rate: 57%, Example 77), 10×PBS (pH 7.4, 0.744 mL), and Otsuka distilled water (6.698 mL) were measured and stirred for 1 hour to acquire a dispersion liquid of nanoparticles of γ-PGA-PAE (concentration: 10 mg/mL). A portion of the acquired solution (2.0 mL) was diluted with 1×PBS (8.0 mL) to acquire a dispersion liquid of nanoparticles of γ-PGA-PAE (2 mg/mL) (79 nm, PDI 0.27).

The acquired dispersion liquid (0.75 mL) was sequentially mixed with 10×PBS (pH 7.4, 0.225 mL), distilled water (1.975 mL), and a commercially available HA antigen [Denka Seiken, Influenza HA Vaccine "SEIKEN": active ingredients include the following three strains (A/California/7/2009 (H1N1) pdm09 strain; A/Texas/50/2012 (H3N2) strain; B/Massachusetts/2/2012 strain), the strains have HA contents (equivalents) of 30 μg or more/mL per strain, HA antigen: 1.5 μg or more; 0.05 mL at 30 μg or more/mL] to prepare the HA vaccine (3.0 mL).

[Example 123] Preparation of Liquid Mixture of Nanoparticles of γ-PGA-PAE and HA Antigen The dispersion liquid acquired as described above (0.75 mL) was sequentially mixed with 10×PBS (pH 7.4, 0.225 mL), distilled water (2.02 mL), and a commercially available HA antigen [Denka Seiken, Influenza HA Vaccine "SEIKEN": active ingredients include the following three strains (A/California/7/2009 (H1N1) pdm09 strain; A/Texas/50/2012 (H3N2) strain; B/Massachusetts/2/2012 strain), the strains have HA contents (equivalents) of 30 μg or more/mL per strain, HA antigen: 0.15 μg or more; 0.005 mL at 30 μg or more/mL] to prepare the HA vaccine (3.0 mL).

[Example 124] Preparation of Liquid Mixture of Nanoparticles of γ-PGA-PAE and HA Antigen The dispersion liquid of nanoparticles of γ-PGA-PAE (1 mL, 20 mg/mL, PAE introduction rate: 57%, dispersed in Example 78) was diluted with 1×PBS (9.0 mL) to acquire a dispersion liquid of nanoparticles of γ-PGA-PAE (2 mg/mL) (78 nm, PDI 0.22).

The acquired dispersion liquid (0.75 mL) was sequentially mixed with 10×PBS (pH 7.4, 0.225 mL), distilled water (1.975 mL), and a commercially available HA antigen [Denka Seiken, Influenza HA Vaccine "SEIKEN": active ingredients include the following three strains (A/California/7/2009 (H1N1) pdm09 strain; A/Texas/50/2012 (H3N2) strain; B/Massachusetts/2/2012 strain), the strains have HA contents (equivalents) of 30 μg or more/mL per strain, HA antigen: 1.5 μg or more; 0.05 mL at 30 μg or more/mL] to prepare the HA vaccine (3.0 mL).

[Example 125] Preparation of Liquid Mixture of Nanoparticles of γ-PGA-PAE and HA Antigen The dispersion liquid acquired as described above (0.75 mL) was sequentially mixed with 10×PBS (pH 7.4, 0.225 mL), distilled water (2.02 mL), and a commercially available HA antigen [Denka Seiken, Influenza HA Vaccine "SEIKEN": active ingredients include the following three strains (A/California/7/2009 (H1N1) pdm09 strain; A/Texas/50/2012 (H3N2) strain; B/Massachusetts/2/2012 strain), the strains have HA contents (equivalents) of 30 μg or more/mL per strain, HA antigen: 0.15 μg or more; 0.005 mL at 30 μg or more/mL] to prepare the HA vaccine (3.0 mL).

[Example 126] Preparation of Liquid Mixture of Nanoparticles of γ-PGA-PAE and HA Antigen γ-PGA-PAE (150 mg, introduction rate: 60%, Example 105), DMSO (5.45 mL), and $Na_2CO_3$ aqueous solution (5.2 mg/0.55 mL) were measured and dissolved with stirring for 2 hours at room temperature to acquire a DMSO aqueous solution (concentration: 25 mg/mL) of γ-PGA-PAE. An acquired solution was filtered with a syringe filter (Corning, 0.2 μm) and this solution was defined as a solution A.

A portion of this solution A (concentration: 25 mg/mL, 0.10 mL) was quickly mixed into 0.05 M NaCl aqueous solution (0.10 mL) to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.20 mL) followed by desalting was performed twice. The acquired residue was dispersed in 1×PBS (0.25 mL) to acquire a solution of nanoparticles of γ-PGA-PAE (10 mg/mL). The nanoparticles of γ-PGA-PAE were measured in terms of mean particle diameter [Z-Ave d. (nm)] and particle diameter dispersion index (PDI) by Zetasizer Nano ZS (Malvern). The results were 0.05 M NaCl, 185 nm (PDI 0.10).

NaCl (11.7 mg) was dissolved in Otsuka distilled water (4.0 mL) and filtered with a syringe filter (0.2 μm). This solution was defined as a solution B. A portion of the solution A (concentration: 25 mg/mL, 2.6 mL) was mixed into a portion of the solution B [0.05 M NaCl aqueous solution (2.6 mL)] to acquire dispersion liquid. The liquid was desalted by using Amicon Ultra 15 (Millipore, 10 K) (centrifugation conditions: 4500 rpm, 30 minutes, 5° C.). An operation of dispersing an acquired residue in distilled water (10 mL) followed by desalting was performed five times. Distilled water (12 mL) was added to the acquired residue to acquire a dispersion liquid C. A portion of the dispersion liquid C (0.05 mL) was dispersed in 1×PBS (1.0 mL) to acquire the dispersion liquid of nanoparticles (197 nm, PDI 0.10). The dispersion liquid C (3.0 mL) was frozen in a freezer at −30° C. This frozen solution was subjected to lyophilization to acquire nanoparticles of γ-PGA-PAE (6 mg, PAE introduction rate: 57%, moisture: 2.2%). The dispersion liquid C (0.765 mL) was sequentially mixed with 10×PBS (pH 7.4, 0.30 mL), distilled water (1.885 mL), and a commercially available HA antigen [Denka Seiken, Influenza HA Vaccine "SEIKEN": active ingredients include the following three strains (A/California/7/2009 (H1N1) pdm09 strain; A/Texas/50/2012 (H3N2) strain; B/Massachusetts/2/2012 strain), the strains have HA contents (equivalents) of 30 μg or more/mL per strain, HA antigen: 1.5 μg or more; 0.05 mL at 30 μg or more/mL] to prepare the HA vaccine (3.0 mL).

[Example 127] Preparation of Liquid Mixture of Nanoparticles of γ-PGA-PAE and HA Antigen The dispersion liquid C acquired as described above (0.765 mL) was sequentially mixed with 10×PBS (pH 7.4, 0.30 mL), distilled water (1.930 mL), and a commercially available HA antigen [Denka Seiken, Influenza HA Vaccine "SEIKEN": active ingredients include the following three strains (A/California/7/2009 (H1N1) pdm09 strain; A/Texas/50/2012 (H3N2) strain; B/Massachusetts/2/2012 strain), the strains have HA contents (equivalents) of 30 μg or more/mL per strain, HA antigen: 0.15 μg for more; 0.005 mL at 30 μg or more/mL] to prepare the HA vaccine (3.0 mL).

[Example 128] Preparation of Liquid Mixture of Nanoparticles of γ-PGA-PAE and HA Antigen γ-PGA-PAE (150 mg, PAE introduction rate: 54%, Example 112), DMSO (4.45 mL), and Na₂CO₃ aqueous solution (6.0 mg/0.55 mL) were measured and dissolved with stirring for 2 hours at room temperature to acquire a DMSO aqueous solution (concentration: 30 mg/mL) of γ-PGA-PAE. An acquired solution was filtered with a syringe filter (Corning, 0.2 μm) and this solution was defined as a solution A.

A portion of this solution A (concentration: 30 mg/mL, 0.10 mL) was quickly mixed into distilled water (0.10 mL) to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.20 mL) followed by desalting was performed twice. The acquired residue was dispersed in 1×PBS (0.30 mL) to acquire a solution of nanoparticles of γ-PGA-PAE (10 mg/mL). The nanoparticles of γ-PGA-PAE were measured in terms of mean particle diameter [Z-Ave d. (nm)] and particle diameter dispersion index (PDI) by Zetasizer Nano ZS (Malvern). The results were 0.00 M NaCl, 199 nm (PDI 0.11).

Otsuka distilled water (4.0 mL) was filtered with a syringe filter (0.2 μm). This solution was defined as a solution B. A portion of the solution A (concentration: 30 mg/mL, 2.2 mL) was mixed into a portion of the solution B [distilled water (2.2 mL)] to acquire dispersion liquid. The liquid was desalted by using Amicon Ultra 15 (Millipore, 10 K) (centrifugation conditions: 4500 rpm, 30 minutes, 5° C.). An operation of dispersing an acquired residue in distilled water (10 mL) followed by desalting was performed five times. Distilled water (12 mL) was added to the acquired residue to acquire a dispersion liquid C. A portion of the dispersion liquid C (0.05 mL) was dispersed in 1×PBS (1.0 mL) to acquire the dispersion liquid of nanoparticles (138 nm, PDI 0.11). A portion of the dispersion liquid C (3.0 mL) was frozen in a freezer at −30° C. This frozen solution was subjected to lyophilization to acquire nanoparticles of γ-PGA-PAE (12 mg, PAE introduction rate: 53%, moisture: 3.8%). A portion of the dispersion liquid C (0.39 mL) was sequentially mixed with 10×PBS (pH 7.4, 0.30 mL), distilled water (2.26 mL), and a commercially available HA antigen [Denka Seiken, Influenza HA Vaccine "SEMEN", 1.5 μg or more; 0.05 mL at 30 μg or more/mL] to prepare the HA vaccine (3.0 mL).

[Example 129] Preparation of Liquid Mixture of Nanoparticles of γ-PGA-PAE and HA Antigen The dispersion liquid C acquired as described above (0.39 mL) was sequentially mixed with 10×PBS (pH 7.4, 0.30 mL), distilled water (2.305 mL), and a commercially available HA antigen [Denka Seiken, Influenza HA Vaccine "SEIKEN": active ingredients include the following three strains (A/California/7/2009 (HINT) pdm09 strain; A/Texas/50/2012 (H3N2) strain; B/Massachusetts/2/2012 strain), the strains have HA contents (equivalents) of 30 μg or more/mL per strain, HA antigen: 1.5 μg or more; 0.005 mL at 30 μg or more/mL] to prepare the HA vaccine (3.0 mL).

[Example 130] Preparation of Liquid Mixture of Nanoparticles of γ-PGA-PAE and HA Antigen A portion of the dispersion liquid C of nanoparticles of γ-PGA-PAE acquired in Example 121 (0.301 mL) was sequentially mixed with 10×PBS (pH 7.4, 0.30 mL), distilled water (2.394 mL), and a commercially available HA antigen [Denka Seiken, Influenza HA Vaccine "SEIKEN": active ingredients include the following three strains (A/California/7/2009 (H1N1) pdm09 strain; A/Texas/50/2012 (H3N2) strain; B/Massachusetts/2/2012 strain), the strains have HA contents (equivalents) of 30 μg or more/mL per strain, 0.15 μg or more; 0.005 mL at 30 μg or more/mL] to prepare the HA vaccine (3.0 mL).

[Example 131] Preparation of Liquid Mixture of Nanoparticles of γ-PGA-D-PAE and HA Antigen γ-PGA-PAE (250 mg, PAE introduction rate: 56%, Example 11), DMSO (5.25 mL), and Na$_2$CO$_3$ aqueous solution (23.3 mg/mL; 1.0 mL) were measured and dissolved with stirring for 2 hours at room temperature to acquire a DMSO aqueous solution (concentration: 40 mg/mL) of γ-PGA-PAE. An acquired solution was filtered with a syringe filter (Corning, 0.2 μm) and this solution was defined as a solution A.

A portion of this solution A (concentration: 40 mg/mL, 0.10 mL) was quickly mixed into NaCl aqueous solutions (0.10 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.20 mL) followed by desalting was performed twice. The acquired residue was dispersed in 1×PBS (0.4 mL) to acquire a solution of nanoparticles of γ-PGA-PAE (10 mg/mL). The nanoparticles of γ-PGA-PAE were measured in terms of mean particle diameter [Z-Ave d. (nm)] and particle diameter dispersion index (PDI) by Zetasizer Nano ZS (Malvern). The results were 0.05 M NaCl, 173 nm (PDI 0.10); 0.10 M NaCl, 293 nm (PDI 0.26); and 0.15 M NaCl, 385 nm (PDI 0.39).

NaCl (14.6 mg) was dissolved in Otsuka distilled water (5.0 mL) and filtered with a syringe filter (0.2 μm). This solution was defined as a solution B. A portion of the solution A (concentration: 40 mg/mL, 3.0 mL) was mixed into a portion of the solution B [distilled water (3.0 mL)] to acquire dispersion liquid. The liquid was desalted by using Amicon Ultra 15 (Millipore, 10 K) (centrifugation conditions: 4500 rpm, 30 minutes, 5° C.). An operation of dispersing an acquired residue in distilled water (10 mL) followed by desalting was performed five times. Distilled water (23 mL) was added to the acquired residue to acquire a dispersion liquid C. A portion of the dispersion liquid C (0.05 mL) was dispersed in 1×PBS (1.0 mL) to acquire the dispersion liquid of nanoparticles (128 nm, PDI 0.07). A portion of the dispersion liquid C (3.0 mL) was frozen in a freezer at −30° C. This frozen solution was subjected to lyophilization to acquire nanoparticles of γ-PGA-PAE (11 mg, PAE introduction rate: 55%, moisture: 3.0%). A portion of the dispersion liquid C (0.422 mL) was sequentially mixed with 10×PBS (pH 7.4, 0.30 mL), distilled water (2.273 mL), and a commercially available HA antigen [Denka Seiken, Influenza HA Vaccine "SEIKEN": active ingredients include the following three strains (A/California/7/2009 (H1N1) pdm09 strain; A/Texas/50/2012 (H3N2) strain; B/Massachusetts/2/2012 strain), the strains have HA contents (equivalents) of 30 μg or more/mL per strain, HA antigen: 1.5 μg or more; 0.005 mL at 30 μg or more/mL] to prepare the HA vaccine (3.0 mL).

[Example 132] Preparation of Liquid Mixture of Nanoparticles of α-D-PGA-L-PAE and HA Antigen α-PGA-PAE (150 mg, PAE introduction rate: 69%, Example 21), DMSO (11.9 mL), and Na$_2$CO$_3$ aqueous solution (6.4 mg/0.6 mL) were measured and dissolved with stirring for 2 hours at room temperature to acquire a DMSO aqueous solution (concentration: 12 mg/mL) of α-PGA-PAE. An acquired solution was filtered with a syringe filter (Corning, 0.2 μm) and this solution was defined as a solution A.

A portion of this solution A (concentration: 12 mg/mL, 0.10 mL) was quickly mixed into NaCl aqueous solutions (0.10 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.20 mL) followed by desalting was performed twice. The acquired residue was dispersed in 1×PBS (0.12 mL) to acquire a solution of nanoparticles of α-PGA-PAE (10 mg/mL). The nanoparticles of α-PGA-PAE were measured in terms of mean particle diameter [Z-Ave d. (nm)] and particle diameter dispersion index (PDI) by Zetasizer Nano ZS (Malvern). The results were 0.05 M NaCl, 155 nm (PDI 0.16); and 0.06 M NaCl, 178 nm (PDI 0.18).

NaCl (24.5 mg) was dissolved in Otsuka distilled water (7.0 mL) and filtered with a syringe filter (0.2 μm). This solution was defined as a solution B. A portion of the solution A (concentration: 12 mg/mL, 5.0 mL) was mixed into a portion of the solution B [0.06 M NaCl (5.0 mL)] to acquire dispersion liquid. The liquid was desalted by using Amicon Ultra 15 (Millipore, 10 K) (centrifugation conditions: 4500 rpm, 30 minutes, 5° C.). An operation of dispersing an acquired residue in distilled water (10 mL) followed by desalting was performed five times. Distilled water (11 mL) was added to the acquired residue to acquire a dispersion liquid C. A portion of the dispersion liquid C (0.05 mL) was dispersed in 1×PBS (1.0 mL) to acquire the dispersion liquid of nanoparticles (129 nm, PDI 0.22). A portion of the dispersion liquid C (3.0 mL) was frozen in a freezer at −30° C. This frozen solution was subjected to lyophilization to acquire nanoparticles of α-PGA-PAE (13 mg, PAE introduction rate: 66%, moisture: 1.7%). A portion of the dispersion liquid C (0.352 mL) was sequentially mixed with 10×PBS (pH 7.4, 0.30 mL), distilled water (2.343 mL), and a commercially available HA antigen [Denka Seiken, Influenza HA Vaccine "SEIKEN": active ingredients include the following three strains (A/California/7/2009 (H1N1) pdm09 strain; A/Texas/50/2012 (H3N2) strain; B/Massachusetts/2/2012 strain), the strains have HA contents (equivalents) of 30 μg or more/mL per strain, HA antigen: 0.15 μg or more; 0.005 mL at 30 μg/mL or more] to prepare the HA vaccine (3.0 mL).

[Example 133] Preparation of Liquid Mixture of Nanoparticles of α-L-PGA-L-PAE and HA Antigen α-PGA-PAE (60 mg, PAE introduction rate: 69%, Example 19), DMSO (9.4 mL), and Na$_2$CO$_3$ aqueous solution (6.3 mg/0.6 mL) were measured and dissolved with stirring for 2 hours at room temperature to acquire a DMSO aqueous solution (concentration: 6 mg/mL) of α-PGA-PAE. An acquired solution was filtered with a syringe filter (Corning, 0.2 μm) and this solution was defined as a solution A.

A portion of this solution A (concentration: 6 mg/mL, 0.10 mL) was quickly mixed into NaCl aqueous solutions (0.10 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.20 mL) followed by desalting was performed twice. The acquired residue was dispersed in 1×PBS (0.06 mL) to acquire a solution of nanoparticles of α-PGA-PAE (10 mg/mL). The nanoparticles of α-PGA-PAE were measured in terms of mean particle diameter [Z-Ave d. (nm)] and particle diameter dispersion index (PDI) by Zetasizer Nano ZS (Malvern). The results were 0.10 M NaCl, 86 nm (PDI 0.13); 0.12 M NaCl, 119 nm (PDI 0.15); 0.14 M NaCl, 173 nm (PDI 0.16); and 0.15 M NaCl, 374 nm (PDI 0.30).

NaCl (98.2 mg) was dissolved in Otsuka distilled water (12.0 mL) and filtered with a syringe filter (0.2 µm). This solution was defined as a solution B. A portion of the solution A (concentration: 6 mg/mL, 9.0 mL) was mixed into a portion of the solution B [0.14 M NaCl (9.0 mL)] to acquire dispersion liquid. The liquid was desalted by using Amicon Ultra 15 (Millipore, 10 K) (centrifugation conditions: 4500 rpm, 30 minutes, 5° C.). An operation of dispersing an acquired residue in distilled water (20 mL) followed by desalting was performed five times. Distilled water (9 mL) was added to the acquired residue to acquire a dispersion liquid C. A portion of the dispersion liquid C (0.05 mL) was dispersed in 1×PBS (1.0 mL) to acquire the dispersion liquid of nanoparticles (183 nm, PDI 0.18). A portion of the dispersion liquid C (3.0 mL) was frozen in a freezer at −30° C. This frozen solution was subjected to lyophilization to acquire nanoparticles of α-PGA-PAE (6 mg, PAE introduction rate: 57%, moisture: 2.4%). A portion of the dispersion liquid C (0.769 mL) was sequentially mixed with 10×PBS (pH 7.4, 0.30 mL), distilled water (1.926 mL), and a commercially available HA antigen [Denka Seiken, Influenza HA Vaccine "SEIKEN": active ingredients include the following three strains (A/California/7/2009 (H1N1) pdm09 strain; A/Texas/50/2012 (H3N2) strain; B/Massachusetts/2/2012 strain), the strains have HA contents (equivalents) of 30 µg or more/mL per strain, HA antigen: 0.15 µg or more; 0.005 mL at 30 µg or more/mL) to prepare the HA vaccine (3.0 mL).

[Example 134] Preparation of Liquid Mixture of Nanoparticles of αβ-DL-Poly Asp-L-PAE and HA Antigen αβ-DL-Poly Asp-L-PAE (100 mg, PAE introduction rate: 62%, Example 23), DMSO (9.6 mL), and Na$_2$CO$_3$ aqueous solution (14.1 mg/0.4 mL) were measured and dissolved with stirring for 2 hours at room temperature to acquire a DMSO aqueous solution (concentration: 10 mg/mL) of αβ-DL-Poly Asp-L-PAE. An acquired solution was filtered with a syringe filter (Corning, 0.2 µm) and this solution was defined as a solution A.

A portion of this solution A (concentration: 10 mg/mL, 0.05 mL) was quickly mixed into NaCl aqueous solutions (0.05 mL) of various concentrations to acquire dispersion liquid. The liquid was desalted by using Amicon Ultra 0.5 (Millipore, 10 K) (centrifugation conditions: 4500 rpm, 30 minutes, 5° C.). An operation of dispersing an acquired residue in distilled water (0.10 mL) followed by desalting was performed twice. The acquired residue was dispersed in 1×PBS (0.05 mL) to acquire a solution of nanoparticles of αβ-DL-Poly Asp-L-PAE (10 mg/mL). The nanoparticles of αβ-DL-Poly Asp-L-PAE were measured in terms of mean particle diameter [Z-Ave d. (nm)] and particle diameter dispersion index (PDI) by Zetasizer Nano ZS (Malvern). The results were 0.05 M NaCl, 86 nm (PDI 0.13); 0.10 M NaCl, 111 nm (PDI 0.10); 0.15 M NaCl, 155 nm (PDI 0.04); 0.18 M NaCl, 192 nm (PDI 0.20); and 0.20 M NaCl, 220 nm (PDI 0.06).

NaCl (105.2 mg) was dissolved in Otsuka distilled water (10.0 mL) and filtered with a syringe filter (0.2 µm). This solution was defined as a solution B. A portion of the solution A (concentration: 10 mg/mL, 7.0 mL) was mixed into a portion of the solution B [0.18 M NaCl (7.0 mL)] to acquire dispersion liquid. The liquid was desalted by using Amicon Ultra 15 (Millipore, 10 K) (centrifugation conditions: 4500 rpm, 30 minutes, 5° C.). An operation of dispersing an acquired residue in distilled water (20 mL) followed by desalting was performed five times. Distilled water (12 mL) was added to the acquired residue to acquire a dispersion liquid C. A portion of the dispersion liquid C (0.05 mL) was dispersed in 1×PBS (1.0 mL) to acquire the dispersion liquid of nanoparticles (225 nm, PDI 0.03). A portion of the dispersion liquid C (3.0 mL) was frozen in a freezer at −30° C. This frozen solution was subjected to lyophilization to acquire nanoparticles of αβ-DL-Poly Asp-L-PAE (14 mg, PAE introduction rate: 60%, moisture: 4.5%). A portion of the dispersion liquid C (0.337 mL) was sequentially mixed with 10×PBS (pH 7.4, 0.30 mL), distilled water (2.358 mL), and a commercially available HA antigen [Denka Seiken, Influenza HA Vaccine "SEIKEN": active ingredients include the following three strains (A/California/7/2009 (H1N1) pdm09 strain; A/Texas/50/2012 (H3N2) strain; B/Massachusetts/2/2012 strain), the strains have HA contents (equivalents) of 30 µg or more/mL per strain, HA antigen: 0.15 ng or more; 0.005 mL at 30 ng or more/mL) to prepare the HA vaccine (3.0 mL).

[Example 135] Cellular Immunity Induction Experiment Using Liquid Mixture of HA Antigen and Nanoparticles of γ-PGA-PAE A. Materials Materials were 0.05 tween 20-containing phosphate buffer solution (PBS-T), skim milk (Wako Pure Chemical Industries, 198-10605), BSA (Sigma, A7030), HRP-labeled anti-mouse IgG antibody (Abcam, Ab7068), TMB substrate solution (Sigma, T0440-100 mL), TMB stop solution (CST, 7002L), wells (96-well flat-bottom plate, Nunc, 112372), HA antigens [commercially available from Denka Seiken, Influenza HA Vaccine "SEIKEN": active ingredients include the following three strains (A/California/7/2009 (H1N1) pdm09 strain; A/Texas/50/2012 (H3N2) strain; B/Massachusetts/2/2012 strain), the strains have HA contents (equivalents) of 30 ng or more/mL per strain], aluminum hydroxide gel (sterilized) [Alum: 2.0 mg/mL, volume: 1.0 mL, pH 7.045, physiological saline (0.85% NaCl)], and various γ-PGA-PAE NPs prepared in the methods of Examples described above. Various vaccine solutions were PBS (200 µL) solutions of HA antigens (0.1 ng or 0.01 µg) and nanoparticles of γ-PGA-PAE (equivalent to 100 µg). Mice (BALB/c female mice, 7 week-old, Charles River Laboratories Japan, Inc.) were used.

B. Method

After about 1 week of acclimation of the mice (BALB/c female mice, 7 week-old), 200 µL of a test substance was subcutaneously administered to the mice by using a 1-mL syringe twice at an interval of 4 weeks. Serums were collected after 2 weeks from the last immunization. For collecting the serums, whole blood taken from the heart under pentobarbital anesthesia was allowed to stand overnight at normal temperature and then centrifuged (3000 rpm, 20 minutes) and each of the serums was divided into two and frozen at −80° C. An antibody titer was evaluated by using the frozen serum.

Preparation of Test Substance (1) Preparation of Test Substance 1

In a sterile cryogenic vial (Corning), Otsuka distilled water (4.5 mL) and ×10 PBS (pH 7.4, 0.50 mL) were measured and sufficiently stirred. This solution was filtered with a syringe filter (0.2 μm) to acquire a solution A. A PBS preparation solution (blank solution without HA) was acquired by measuring 3.0 mL from this solution A.

(2) Preparation of Test Substance 2

In a sterile cryogenic vial (Corning), Otsuka distilled water [2650 μL filtered with a syringe filter (0.2 μm)] and ×10 PBS [pH 7.4; 300 μL filtered with a syringe filter (0.2 μm)] were measured and sufficiently stirred. This solution was mixed with a commercially available HA antigen [Denka Seiken, Influenza HA Vaccine "SEIKEN": active ingredients include the following three strains (A/California/7/2009 (H1N1) pdm09 strain; A/Texas/50/2012 (H3N2) strain; B/Massachusetts/2/2012 strain), the strains have HA contents (equivalents) of 30 μg or more/mL per strain: equivalent to 1.5 μg or more of HA content (equivalent) of each strain, i.e., 0.05 mL was used at 30 μg or more/mL] to prepare HA vaccine (3.0 mL) (description of "or more" is based on an attached document). This vaccine has HA concentration of 0.5 μg/mL or more.

(3) Preparation of Test Substance 3

In a sterile cryogenic vial (Corning), Otsuka distilled water [2695 μL filtered with a syringe filter (0.2 μm)] and ×10 PBS [pH 7.4; 300 μL filtered with a syringe filter (0.2 μm)] were measured and sufficiently stirred. This solution was mixed with a commercially available HA antigen [Denka Seiken, Influenza HA Vaccine "SEIKEN": active ingredients include the following three strains (A/California/7/2009 (H1N1) pdm09 strain; A/Texas/50/2012 (H3N2) strain; B/Massachusetts/2/2012 strain), the strains have HA contents (equivalents) of 30 μg or more/mL per strain: equivalent to 0.15 μg more of HA content (equivalent) of each strain, i.e., 0.005 mL was used at 30 μg or more/mL] to prepare HA vaccine (3.0 mL) (description of "or more" is based on an attached document). This vaccine has HA concentration of 0.05 μg/mL or more.

(4) Preparation of Test Substance 4

In a sterile cryogenic vial (Corning), 0.375 mL of aluminum hydroxide gel (Alum) (sterilized) [Alum: 2.0 mg/mL, volume: 1.0 mL, pH 7.045, physiological saline (0.85% NaCl)] was measured, and Otsuka distilled water (0.973 mL) and ×10 PBS (pH 7.4, 0.15 mL) were then measured and sufficiently stirred. This solution was sequentially mixed with a commercially available HA antigen [Denka Seiken, Influenza HA Vaccine "SEIKEN": active ingredients include the following three strains (A/California/7/2009 (H1N1) pdm09 strain; A/Texas/50/2012 (H3N2) strain; B/Massachusetts/2/2012 strain), the strains have HA contents (equivalents) of 30 μg or more/mL per strain: equivalent to 0.075 μg or more of HA content (equivalent) of each strain, i.e., 0.0025 mL was used at 30 μg or more/mL] to prepare control HA vaccine (1.5 mL) (description of "or more" is based on an attached document). This vaccine has HA concentration of 0.05 μg/mL or more.

(5) Preparation of Test Substance 5

For Example 127 using nanoparticles of γ-PGA-PAE instead of Alum, HA vaccine was prepared (3.0 mL) in the same way as Test Substance 4. This vaccine has HA concentration of 0.05 μg/mL or more.

(6) Preparation of Test Substance 6

For Example 129 using nanoparticles of γ-PGA-PAE instead of Alum, HA vaccine was prepared (3.0 mL) in the same way as Test Substance 4. This vaccine has HA concentration of 0.05 μg/mL or more.

(7) Preparation of Test Substance 7

For γ-PGA-PAE of Example 130 using nanoparticles of γ-PGA-PAE instead of Alum, HA vaccine was prepared (3.0 mL) in the same way as Test Substance 4. This vaccine has HA concentration of 0.05 μg/mL or more.

(8) Preparation of Test Substance 8

For Example 129 using nanoparticles of γ-PGA-PAE instead of Alum, HA vaccine was prepared (3.0 mL) in the same way as Test Substance 4. This vaccine has HA concentration of 0.05 μg/mL or more.

C. Evaluation method

A titer of monoclonal antibody (mAb) to HA protein was evaluated as an evaluation item.

The HA antigen (containing 0.025 μg or more; 100 μL of coating buffer) is added to a well, refrigerated overnight, and then washed with PBS-T by a microplate washer six times. After block buffer (200 μL) was added to this well and allowed to act at room temperature for 2 hours, the well was washed in the same way with PBS-T six times. After [test substance solution (such as serum/blank, see Table 3), 100 μL] was added to this well and allowed to act at room temperature for 2 hours, the well was washed in the same way with PBS-T six times. After an anti-mouse IgG antibody (100 μL) was added to this wall and allowed to act at room temperature for 2 hours, the well was washed in the same way with PBS-T six times. After the TMB substrate solution (100 μL) was added to the well and allowed to act at room temperature for 10 minutes, the TMB stop solution (100 μL) was added. The acquired solution was measured by a plate reader in terms of absorbance at 450 nm.

TABLE 3

| Group | Administered substance | Details | HA content (μg/mL) | Antibody titer [average] |
|---|---|---|---|---|
| 1 | Test substance 1 | PBS (blank) | 0 | 13.0 |
| 2 | Test substance 2 | HA (x10) | 0.5 or more | 26.9 |
| 3 | Test substance 3 | HA (x1) | 0.05 or more | 20.5 |
| 4 | Test substance 4 | HA (x1) - Alum | 0.05 or more | 25.7 |
| 5 | Test substance 5 | HA (x1) - γ-PGA-PAE Nanoparticles (Example 127) | 0.05 or more | 26.7 |
| 6 | Test substance 6 | HA (x1) - γ-PGA-PAE Nanoparticles (Example 129) | 0.05 or more | 26.9 |
| 7 | Test substance 7 | HA (x1) + γ-PGA-PAE Nanoparticles (Example 130) | 0.05 or more | 27.3 |
| 8 | Test substance 8 | HA (x1) + γ-PGA-PAE Nanoparticles (Example 125) | 0.05 or more | 27.8 |

D. Results

These results (see Table 3 and FIG. 1) showed that the nanoparticles of γ-PGA-PAE produced and prepared in the present invention have extremely excellent performance as an adjuvant.

[Example 136] Physical Properties of γ-PGA-PAE Na Salt

The following table describes the relative molecular weight, the values of x, y, z in monomer units, and the total number (n) of monomer units in the graft copolymer of the γ-PGA-PAE Na salt synthesized as described above.

The relative molecular weight in the table was determined by a molecular weight measurement method using SEC-HPLC measurement: TSKgel α-M 300×7.8 mm I.D. (dual), 5 mM NaNO$_3$ DMSO:H$_2$O (9:1), 0.8 mL/minute, 40° C., RI detector, standard: pullulan (Shodex).

The values of x, y, and z in the table are determined by using the following experiment method and the following calculation equations represented by (Eq.1) and (Eq. 2). By way of example, the calculation equations for γ-PGA-PAE (Na salt) are shown:

x: calculated from Eq. 2 after determination of [y] and [z] described below;
y: calculated from atomic absorption spectrometry or quantification of Na ions by LCMS;
z: calculated by $^1$H-NMR as an introduction rate of PAE; molecular weight of γ-PGA-PAE (Na salt): calculated by a relative molecular weight determination method using SEC-HPLC or an absolute molecular weight determination method using viscometer, DLS detector, SLS detector, and the like by GPC-Max (Viscotek) etc.; and n: the number of glutamic acid monomers in the graft copolymer (Glu number).

[Math. 4]

$$\text{Molecular weight of γ-PGA-PAE (Na salt)} = [\text{Molecular weight of hydrogen of N terminal}] + [(\text{Molecular weight of -Glu-OH—})\times([n]\times[x])] + [(\text{Molecular weight of -Glu-Ona-})\times([n]\times[y])] + [(\text{Molecular weight of -Glu-Phe-OEt-})\times([n]\times[z])] + [\text{Molecular weight of hydroxyl group (or sodium salt thereof) of C terminal}] = [1.007947\times1] + [(12.0111\times5+1.007947)\times7+15.99943\times3+14.00675\times1+22.98977\times0)\times([n]\times[x])] + [(12.0111\times5+1.007947\times6+15.99943\times3+14.00675\times1+22.98977\times1)\times([n]\times[y])] + [(12.0111\times16+1.007947\times20+15.99943\times4+14.00675\times2+22.98977\times0)\times([n]\times[z])] + [15.99943\times1+(1.007947\times1 \text{ or } 22.98977\times1)]$$ (Eq. 1)

[Math. 5]

$$[x]+[y]+[z]=1$$ (Eq. 2)

The number of glutamic acid monomers in the graft copolymer (Glu number) was calculated from acquired experiment results by using the equations implemented as a spreadsheet of Excel 2010 (Microsoft). The results are described in the following table.

The total number (n) of monomer units in the graft copolymer in the table is the number derived from the number of glutamic acid monomers in the graft copolymer (Glu number).

TABLE 4

| Examples | Relative molecular weight (kDa) | x | y | z | n |
|---|---|---|---|---|---|
| 117-1 | 181 | 0.42 | 0.00 | 0.56 | 787 |
| 117-2 | 140 | 0.33 | 0.10 | 0.57 | 602 |
| 117-3 | 157 | 0.20 | 0.23 | 0.57 | 669 |
| 117-4 | 108 | 0.15 | 0.26 | 0.59 | 452 |
| 117-5 | 61 | 0.15 | 0.43 | 0.63*[1] | 244 |
| 118-1 | 153 | 0.36 | 0.06 | 0.57 | 663 |
| 118-2 | 145 | 0.26 | 0.16 | 0.57 | 622 |
| 118-3 | 146 | 0.18 | 0.23 | 0.59 | 616 |
| 118-4 | 163 | 0.20 | 0.22 | 0.58 | 690 |
| 118-5 | 152 | 0.20 | 0.22 | 0.58 | 646 |
| 118-6 | 119 | 0.16 | 0.25 | 0.59 | 500 |
| 118-7 | 103 | 0.14 | 0.27 | 0.59 | 431 |
| 118-8 | 97 | 0.12 | 0.28 | 0.59 | 403 |
| 118-9 | 80 | 0.10 | 0.30 | 0.59 | 335 |
| 118-10 | 69 | 0.09 | 0.31 | 0.61 | 283 |
| 118-11 | 76 | 0.09 | 0.30 | 0.62 | 311 |
| 118-12 | 60 | 0.03 | 0.34 | 0.63 | 241 |

*[1] Ethyl ester of the PAE side chain was hydrolyzed by 21%.

[Example 137] Calculation (Calculated Value) of Hydrophobic Parameter K (Clog P)

Clog P values are calculated for the graft copolymers (γ-PGA-PAE) and the ionized graft copolymers produced in accordance with Examples described above by ChemDraw Ultra (12.0.2.1076), Cambridgesoft. The results are described in the following table.

TABLE 5

| Examples | Clog P |
|---|---|
| 1 | −100 |
| 2 | −264 |
| 3 | −236 |
| 4 | −38 |
| 5 | 31 |
| 6 | −127 |
| 7 | −48 |
| 8 | −2 |
| 10 | −16 |
| 11 | −106 |
| 12 | −105 |
| 17 | −1271 |
| 25 | 185 |
| 26 | −61 |
| 27 | 360 |
| 28 | −127 |
| 29 | 273 |
| 30 | 54 |
| 31 | −355 |
| 32 | −532 |
| 33 | −1675 |
| 34 | −206 |
| 35 | −233 |
| 36 | 252 |
| 37 | 195 |
| 39 | 277 |
| 40 | −158 |
| 41 | −483 |
| 42 | −519 |
| 43 | 600 |
| 44 | −238 |
| 45 | −163 |
| 46 | −220 |
| 47 | −215 |
| 48 | −292 |
| 49 | −158 |
| 50 | −216 |
| 51 | −276 |
| 52 | −307 |
| 117-1 | −174 |
| 117-2 | −181 |
| 117-3 | −251 |
| 117-4 | −170 |
| 117-5 | −101 |
| 118-1 | −177 |
| 118-2 | −206 |
| 118-3 | −212 |
| 118-4 | −243 |
| 118-5 | −228 |
| 118-6 | −183 |
| 118-7 | −162 |

TABLE 5-continued

| Examples | Clog P |
|---|---|
| 118-8 | −152 |
| 118-9 | −131 |
| 118-10 | −106 |
| 118-11 | −110 |
| 118-12 | −87 |

[Example 138] Measurement (Actual Measurement Value) of Hydrophobic Parameter K (log Pow)

γ-PGA-PAE [37 mg, n=403, x:y:z(12:28:59)] synthesized in accordance with Example 118-8 was suspended and stirred in 1-octanol (Wako Special Grade, 20 mL) and distilled water (20 mL) and allowed to stand overnight. The solution was filtered by a 0.2-μm filter. Each of organic and water layers was sampled 5 mL by a transfer pipette and moderately stirred for 1 hour and then allowed to stand still. Each of the organic and water layers was sampled 2 mL by a transfer pipette into a 25 mL measuring flask. To each of the solutions, 2 M sodium hydroxide aqueous solution (10 mL) was added for hydrolysis at outside temperature of 50° C. for 2 hours. Each of the solutions was neutralized by adding 2 M hydrochloric acid aqueous solution (10 mL) and then diluted in the measuring flask. Phenylalanine in the sample (A) from the water layer and the sample (B) from the organic layer was quantitatively analyzed by HPLC (Sunniest RP-AQUA 100×2.0 mm i.d. 3 μm, UV 220 nm, 60° C., 0.4 mL/minute; mobile phase A: 0.1% TFA aq.; mobile phase B: 0.1% TFA/MeCN; Program 0-5 minutes 5% B, 5-15 minutes 5-35% B, 15-18 minutes 35% B, 18-23 minutes, 75% B; 23.01 minutes 5% B, Cycle: 30 minutes).

As a result, the phenylalanine content of (A) was (A) 0.012875 mg and the phenylalanine content of (B) was 0.003700 mg. This results in log Pow=$\log_{10}$(0.003700/0.012875)=$\log_{10}$(0.2874)=−0.542.

INDUSTRIAL APPLICABILITY

The present invention enables the acquisition of a free form of the graft copolymer of a poly(amino acid) or a salt thereof and a hydrophobic primary amine compound or a salt thereof in a short time at a high yield, and the ionized graft copolymer may be acquired with a small amount of solvent.

The acquired free form of the graft copolymer is hardly deliquesced and therefore easily handled as a row material and makes quality control easy since the state of the N terminal important for determination of polymer structure may be known.

When nanoparticles are formed from the free form of the graft copolymer, the hydrophobicity of the graft copolymer may be balanced by adjusting an ion species and an ionization amount to produce nanoparticles suitable for a purpose.

Although concentration may be increased in the step of producing nanoparticles of the ionized graft copolymer of the present invention, the aggregation of acquired nanoparticles is suppressed and the reproducibility of forming/acquiring nanoparticles suitable for a purpose is increased by adjusting an ionization amount.

The invention claimed is:

1. A production method of a graft copolymer of a poly (amino acid) selected from the group consisting of poly(α-glutamic acid) or a salt thereof, and poly(aspartic acid) or a salt thereof, and a hydrophobic primary amine compound represented by Formula (I): A-$NH_2$ or a salt thereof, wherein A denotes a hydrophobic moiety, the method comprising the steps of:
   (1) acquiring a graft copolymer by condensation of the poly(amino acid) or a salt thereof with the hydrophobic primary amine compound represented by Formula (I) or a salt thereof; and
   (2) isolating the graft copolymer by allowing an acid to act on the graft copolymer acquired at step (1) at a temperature of 40 to 70° C.

2. The production method according to claim 1, wherein the hydrophobic primary amine compound is an α-amino acid derivative.

3. The production method according to claim 2, wherein the α-amino acid derivative is a phenylalanine derivative.

4. The production method according to claim 3, wherein the phenylalanine derivative is phenylalanine ethyl ester.

5. A production method of a graft copolymer of poly(γ-glutamic acid) or a salt thereof, and a hydrophobic primary amine compound represented by Formula (I): A-$NH_2$ or a salt thereof, wherein A denotes a hydrophobic moiety, the method comprising the steps of:
   (1) acquiring a graft copolymer by condensation of the poly(γ-glutamic acid) or salt thereof with the hydrophobic primary amine compound represented by Formula (I) or salt thereof, and
   (2) isolating the graft copolymer by allowing an acid to act on the graft copolymer acquired at step (1).

6. The production method according to claim 5, wherein at step (2), the acid is allowed to act on the graft copolymer at a temperature of 0 to 80° C.

7. A production method of nanoparticles containing an ionized graft copolymer of a poly(amino acid) selected from the group consisting of poly(γ-glutamic acid), poly(α-glutamic acid), and poly(aspartic acid) or a salt thereof and a hydrophobic primary amine compound represented by Formula (I): A-$NH_2$ or a salt there, wherein A denotes a hydrophobic moiety, the method comprising the steps of
   (1) condensing a poly(amino acid) selected from the group consisting of poly(γ-glutamic acid), poly(α-glutamic acid), and poly(aspartic acid) or a salt thereof and a hydrophobic primary amine compound represented by Formula (I): A-$NH_2$ or a salt thereof, wherein A denotes a hydrophobic moiety;
   (2) isolating a graft copolymer by allowing an acid to act on a condensate acquired at step (1);
   (3) ionizing the graft copolymer by allowing a hydroxide of alkali metal, a carbonate of alkali metal, a hydrogencarbonate of alkali metal, a phosphate of alkali metal, a monohydrogen phosphate of alkali metal, a dihydrogen phosphate of alkali metal, an organic acid salt of alkali metal, or an acidic amino-acid salt of alkali metal to act on the graft copolymer isolated at step (2); and
   (4) forming nanoparticles of the ionized graft copolymer acquired at step (3).

* * * * *

UNITED STATES PATENT AND TRADEMARK OFFICE
CERTIFICATE OF CORRECTION

PATENT NO. : 9,815,938 B2
APPLICATION NO. : 14/392185
DATED : November 14, 2017
INVENTOR(S) : Mitsuhisa Yamano, Toshiaki Nagata and Hideki Saitoh It is certified that error appears in the above-identified patent and that said Letters Patent is hereby corrected as shown below:

In the Claims

Claim 7, Column 88, Line 42, after "or a salt" and before ", wherein A" please replace "there" with --thereof--

Signed and Sealed this
Nineteenth Day of December, 2017

Joseph Matal
*Performing the Functions and Duties of the*
*Under Secretary of Commerce for Intellectual Property and*
*Director of the United States Patent and Trademark Office*